(12) United States Patent
Foster et al.

(10) Patent No.: US 11,944,688 B2
(45) Date of Patent: *Apr. 2, 2024

(54) BIOLOGICALLY ACTIVE COMPOUNDS

(71) Applicant: SUTURA THERAPEUTICS LTD, Providenciales (TC)

(72) Inventors: Keith Foster, Surrey (GB); Wouter Eilers, Reading (GB); Adam James Reginald Gadd, Reading (GB)

(73) Assignee: SUTURA THERAPEUTICS LTD, Birkenhead (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/088,933

(22) Filed: Dec. 27, 2022

(65) Prior Publication Data

US 2023/0158166 A1    May 25, 2023

Related U.S. Application Data

(63) Continuation of application No. 16/061,548, filed as application No. PCT/GB2016/054028 on Dec. 21, 2016, now Pat. No. 11,541,124.

(30) Foreign Application Priority Data

Dec. 21, 2015 (GB) ...................... 1522548

(51) Int. Cl.
| | | |
|---|---|---|
| *A61K 47/64* | (2017.01) | |
| *A61K 47/65* | (2017.01) | |
| *A61K 48/00* | (2006.01) | |
| *A61P 21/00* | (2006.01) | |
| *C07C 13/00* | (2006.01) | |
| *C07K 1/107* | (2006.01) | |
| *C07K 7/02* | (2006.01) | |
| *C07K 19/00* | (2006.01) | |

(52) U.S. Cl.
CPC .............. *A61K 47/65* (2017.08); *A61K 47/64* (2017.08); *A61K 48/005* (2013.01); *A61K 48/0075* (2013.01); *A61P 21/00* (2018.01); *C07C 13/00* (2013.01); *C07K 7/02* (2013.01); *C07K 19/00* (2013.01)

(58) Field of Classification Search
CPC ...... A61K 47/65; A61K 47/64; A61K 48/005; A61K 48/0075; A61P 21/00; C07C 13/00; C07K 7/02; C07K 19/00
See application file for complete search history.

(56) References Cited

U.S. PATENT DOCUMENTS

2022/0062431 A1    3/2022 Foster et al.

FOREIGN PATENT DOCUMENTS

| CN | 101790385 A | 7/2010 |
|---|---|---|
| CN | 103121959 A | 5/2013 |
| CN | 103626850 A | 3/2014 |
| CN | 103998458 A | 8/2014 |
| JP | 2012-506703 B2 | 3/2012 |
| JP | 2014-515762 B2 | 7/2014 |
| JP | 2018521970 A | 8/2018 |
| WO | WO-1989003849 A1 | 5/1989 |
| WO | 2009/008725 A2 | 1/2009 |
| WO | WO-2009054725 A3 | 10/2009 |
| WO | WO-2009149214 A2 | 12/2009 |
| WO | 2010/048586 A1 | 4/2010 |
| WO | WO-2010123369 A1 | 10/2010 |
| WO | 2011/008260 A2 | 1/2011 |
| WO | 2011/111874 A1 | 9/2011 |
| WO | WO-2011131693 A2 | 10/2011 |
| WO | 2012/150960 A1 | 11/2012 |

(Continued)

OTHER PUBLICATIONS

Aartsma-Rus, et al., "Therapeutic antisense-induced exon skipping in cultured muscle cells from six different DMD patients". Human Molecular Genetics (Apr. 15, 2003); 12(8): 907-914.

Agrawal, et al., "Site-specific excision from RNA by RNase H and mixed-phosphate-backbone oligodeoxynucleotides". Proceedings of the National Academy of Sciences (Feb. 1, 1990): 87(4): 1401-1405.

Alter, et al., "Systemic delivery of morpholino oligonucleotide restores dystrophin expression bodywide and improves dystrophic pathology". Nature Medicine (Feb. 2006): 12(2): 175-177.

Andaloussi, et al., "Use of cell-penetrating-peptides in oligonucleotide splice switching therapy", Current Gene Therapy (Jun. 1, 2012); 12(3): 161-178.

(Continued)

*Primary Examiner* — Julie Ha
*Assistant Examiner* — Kristina M Hellman
(74) *Attorney, Agent, or Firm* — Duane Morris LLP; Thomas J. Kowalski

(57) ABSTRACT

The invention relates to improvements in drug delivery and more particularly to the use of Cell Penetrating Agents (CPA's) or Cell Penetrating Peptides (CPP's) which have been stabilized by, for example: i) stapling two amino acids to form Stapled CPP's (StaP's) or ii) stitching three or more amino acids to form stitched CPP's (StiP's). These stabilized CPP's are conjugated to a drug or Biologically Active Compound (BAC) directly or via a Bi-Functional Linker (BFL) so that the BAC can be carried though a cell membrane by the CPP. The resulting molecules are referred to as Drug Carrying Cell Penetrating Molecules (DCCPM's). The preferred BAC is an electrically low charge carrying oligonucleotide such as a phosphorodiamidate morpholino oligonucleotide (PMO). The invention also relates to a method of facilitating the uptake of a BAC into a cell, the use of a DCCPM in the treatment of a disease requiring alteration of an endogenous or exogenous gene, a method of improving the bioavailability of a drug or BAC, a method of introducing a drug or BAC to a site which is refractory to the drug or BAC in its native state, a method of treating a subject comprising administering the DCCPM's of the invention and to a pharmaceutical composition comprising the DCCPM and one or more pharmaceutically acceptable excipients.

26 Claims, 44 Drawing Sheets

Specification includes a Sequence Listing.

(56) References Cited

FOREIGN PATENT DOCUMENTS

| WO | 2013/030569 A3 | 3/2013 |
|---|---|---|
| WO | 2013/150338 A1 | 10/2013 |
| WO | WO-2014053622 A1 | 4/2014 |
| WO | WO-2014064258 A1 | 5/2014 |
| WO | 2014/161284 A1 | 10/2014 |
| WO | WO-2016187425 A1 | 11/2016 |
| WO | WO-2017011820 A2 | 1/2017 |
| WO | WO-2017109494 A1 | 6/2017 |
| WO | WO-2019002875 A1 | 1/2019 |

OTHER PUBLICATIONS

Balraju, et al., "Synthesis of conformationally constrained cyclic peptides using an Intramolecular Sonogashira coupling." The Journal of Organic Chemistry (Nov. 11, 2005); 70(23): 9626-9628.

Bendifallah, et al., "Evaluation of cell-penetrating peptides (CPPs) as vehicles for intracellular delivery of antisense peptide nucleic acid (PNA)". Bioconjugate Chemistry (May 17, 2006); 17(3): 750-758.

Betts and Wood, "Cell penetrating peptide delivery of splice directing oligonucleotides as a treatment for Duchenne muscular dystrophy". Current Pharmaceutical Design (May 1, 2013); 19(16): 2948-2462.

Betts, et al., "Pip6-PMO, a new generation of peptide-oligonucleotide conjugates with improved cardiac exon skipping activity for DMD treatment", Molecular Therapy-Nucleic Acids (Aug. 1, 2012); 1:e38, 13 pages.

Bracken, et al., "Synthesis and Nuclear Magnetic Resonance Structure Determination of an. alpha.-Helical, Bicyclic, Lactam-Bridged Hexapeptide". Journal of the American Chemical Society (Jul. 1994); 116(14): 6431-6432.

Campbell, et al., "Oligodeoxynucleoside phosphorothioate stability in subcellular extracts, culture media, sera and cerebrospinal fluid". Journal of Biochemical and Biophysical Methods (Mar. 1, 1990); 20(3): 259-267.

Cantel, et al., "Synthesis and conformational analysis of a cyclic peptide obtained via i to i+ 4 intramolecular side-chain to side-chain azide-alkyne 1, 3-dipolar cycloaddition". The Journal of Organic Chemistry (Aug. 1, 2008): 73(15); 5663-5674.

Chang, et al., "Stapled a-helical peptide drug development: A potent dual inhibitor of MDM2 and MDMX for p53-dependent cancer therapy". Proceedings of the National Academy of Sciences (Sep. 3, 2013); 110(36): E3445-E3454.

Chiriboga, et al., "Results from a phase 1 study of nusinersen (ISIS-SMNRx) in children with spinal muscular atrophy". Neurology (Mar. 8, 2016); 86(10): 890-897.

Chu, Qian, I., "Targeted ß-catenin Ubiquitination and Degradation Using Bifunctional Stapled Peptides II. Studies on Cell Penetration by Stapled Peptides". Doctoral Dissertation, Harvard University, Nov. 2013, pp. 1-153, 169 pages.

Cirak, et al., "Exon skipping and dystrophin restoration in patients with Duchenne muscular dystrophy after systemic phosphorodiamidate morpholino oligomer treatment: an open-label, phase 2, dose-escalation study". The Lancet (Aug. 13, 2011); 378(9791): 595-605. Epub Jul. 23, 2011.

Derossi, D. et al. (Apr. 8, 1994) "The Third Helix of the Antennapedia Homeodomain Translocates through Biological Membranes" J Biol Chem, 269(14):10444-10450.

Dirin, et al., "Influence of diverse chemical modifications on the ADME characteristics and toxicology of antisense oligonucleotides". Expert Opinion on Biological Therapy (Jun. 1, 2013); 13(6): 875-888. Epub Mar. 2, 2013.

Ferlini, et al., "T.I.2 Exon skipping and PRO044 in Duchenne muscular dystrophy: Extending the program", Abstracts / Neuromuscular Disorders (2013); 23: Abstract T.I.2, p. 847.

Gautam, et al., "CPPsite: a curated database of cell penetrating peptides". Database. (Jan. 1, 2012); Article IDS bas015, pp. 1-7.

Goemans, et al., "A randomized placebo-controlled phase 3 trial of an antisense oligonucleotide, drisapersen, in Duchenne muscular dystrophy". Neuromuscular Disorders (Jan. 1, 2018); 28(1): 4-15, 12 pages. Epub Dec. 6, 2017.

Goemans, et al., "Long-term efficacy, safety, and pharmacokinetics of drisapersen in Duchenne muscular dystrophy: results from an open-label extension study". PLoS One (Sep. 2, 2016): 11(9): e0161955, 20 pages.

Goemans, et al., "P.7.1 A prospective natural history study of the progression of physical impairment, activity limitation, and quality of life in Duchenne muscular dystrophy", Neuromuscular Disorders (2013); 23(9-10): 773.

Heald, et al., "Safety and pharmacokinetic profiles of phosphorodiamidate morpholino oligomers with activity against ebola virus and marburg virus: results of two single-ascending-dose studies", Antimicrobial Agents and Chemotherapy (Nov. 2014); 58(11): 6639-6647.

Heemskerk, et al., "In vivo comparison of 2'-O-methyl phosphorothioate and morpholino antisense oligonucleotides for Duchenne muscular dystrophy exon skipping". The Journal of Gene Medicine: A Cross-Disciplinary Journal for Research on the Science of Gene Transfer and Its Clinical Applications (Mar. 2009): 11(3): 257-266.

Hirose, et al., "Transient focal membrane deformation induced by arginine-rich peptides leads to their direct penetration into cells". Molecular Therapy (May 1, 2012); 20(5): 984-993.

Hoffman, et al., "Dystrophin: the protein product of the Duchenne muscular dystrophy locus". Cell (Dec. 24, 1987); 51(6): 919-928.

International Preliminary Report on Patentability in International Application No. PCT/GB2016/054028 dated Jun. 26, 2018, 9 pages.

International Preliminary Report on Patentability in International Application No. PCT/GB2018/051818 dated Oct. 1, 2019, 19 pages.

International Search Report and Written Opinion in International Application No. PCT/GB2016/054028 dated Mar. 24, 2017, 13 pages.

International Search Report and Written Opinion in International Application No. PCT/GB2018/051818 dated Nov. 2, 2018, 16 pages.

Ivanova, et al., "Improved cell-penetrating peptide-PNA conjugates for splicing redirection in HeLa cells and exon skipping in mdx mouse muscle". Nucleic Acids Research (Nov. 1, 2008); 36(20): 6418-6428. Epub Oct. 8, 2008.

Iversen, et al., "Discovery and early development of AVI-7537 and AVI-7288 for the treatment of Ebola virus and Marburg virus infections". Viruses (Nov. 2012); 4(11): 2806-2830.

Jearawiriyapaisarn, et al., "Long-term improvement in mdx cardiomyopathy after therapy with peptide-conjugated morpholino oligomers", Cardiovascular Research (Feb. 1, 2010); 85(3): 444-453. Epub Oct. 8, 2009.

Jearawiriyapaisarn, et al., "Sustained dystrophin expression induced by peptide-conjugated morpholino oligomers in the muscles of mdx mice". Molecular Therapy (Sep. 1, 2008); 16(9): 1624-1629. Epub Jun. 10, 2008.

Kinali, et al., "Local restoration of dystrophin expression with the morpholino oligomer AVI-4658 in Duchenne muscular dystrophy: a single-blind, placebo-controlled, dose-escalation, proof-of-concept study". The Lancet Neurology (Oct. 1, 2009); 8(10): 918-928.

Kreutz, et al., "Antibody-antigen-adjuvant conjugates enable co-delivery of antigen and adjuvant to dendritic cells in cis but only have partial targeting specificity". PLoS One (Jul. 10, 2012); 7(7): e40208, 12 pages. Epub Jul. 10, 2012.

Lau, et al., "Peptide stapling techniques based on different macrocyclisation chemistries". Chemical Society Reviews (Sep. 8, 2015); 44(1): 91-102. Epub Sep. 8, 2014.

Lautrette, et al., "Nitrogen arylation for macrocyclization of unprotected peptides". Journal of the American Chemical Society (Jul. 13, 2016); 138(27): 8340-8343. Epub Jun. 30, 2016.

Lehto, et al., Cellular trafficking determines the exon skipping activity of Pip6a-PMO in mdx skeletal and cardiac muscle cells. Nucleic Acids Research (Mar. 1, 2014); 42(5): 3207-32017. Epub Dec. 23, 2013.

(56) References Cited

OTHER PUBLICATIONS

Lu, et al., "Systemic delivery of antisense oligoribonucleotide restores dystrophin expression in body-wide skeletal muscles". Proceedings of the National Academy of Sciences (Jan. 4, 2005); 102(1): 198-203.
Melacini, et al., "Multiconformational NMR analysis of sandostatin (octreotide): Equilibrium between ß-sheet and partially helical structures". Biochemistry (Feb. 11, 1997); 36(6): 1233-1241.
Mendell, et al., Eteplirsen for the treatment of Duchenne muscular dystrophy. Annals of Neurology (Nov. 2013); 74(5): 637-647. Epub Sep. 10, 2013.
Mendell, et al., "Evidence-based path to newborn screening for Duchenne muscular dystrophy". Annals of Neurology (Mar. 2012); 71(3): 304-313.
Mier, et al., "Peptide-PNA conjugates: Targeted transport of antisense therapeutics into tumors". Angewandte Chemie International Edition (Apr. 29, 2003); 42(17): 1968-1971.
Ming Yang, Molecular Recognition in Pharmaceutical Research, Peking Union Medical College Press (Mar. 1999); pp. 88-90, and Machine translation, 9 pages.
Monaco, et al., "An explanation for the phenotypic differences between patients bearing partial deletions of the DMD locus". Genomics (Jan. 1, 1988): 2(1): 90-95.
Moulton, et al., "Morpholinos and their peptide conjugates: therapeutic promise and challenge for Duchenne muscular dystrophy". Biochimica et Biophysica Acta (BBA)—Biomembranes (Dec. 1, 2010); 1798(12): 2296-2303. Epub Feb. 17, 2010.
Nakase, et al., "Interaction of arginine-rich peptides with membrane-associated proteoglycans is crucial for induction of actin organization and macropinocytosis". Biochemistry (Jan. 16, 2007); 46(2): 492-501.
Sazani, et al., "Safety pharmacology and genotoxicity evaluation of AVI-4658", International Journal of Toxicology (Mar. 2010); 29(2): 143-156. Epub Jan. 28, 2010.
Sazani, et al., "Repeat-dose toxicology evaluation in cynomolgus monkeys of AVI-4658, a phosphorodiamidate morpholino oligomer (PMO) drug for the treatment of duchenne muscular dystrophy". International Journal of Toxicology (May 2011); 30(3): 313-321. Epub May 3, 2011.
Shibahara, et al., "Inhibition of human immunodeficiency virus (HIV-1) replication by synthetic oligo-RNA derivatives". Nucleic Acids Research (Jan. 11, 1989); 17(1): 239-252.
Tereshko, et al., "Correlating structure and stability of DNA duplexes with incorporated 2'-O-modified RNA analogues". Biochemistry (Jul. 28, 1998); 37(30): 10626-10634.
TÜNNEMANN, et al., "Live-cell analysis of cell penetration ability and toxicity of oligo-arginines". Journal of Peptide Science: An Official Publication of the European Peptide Society (Apr. 2008); 14(4): 469-476.
U.S. Appl. No. 16/626,476 for Compounds Comprising Stapled or Stitched Peptides for Improved Drug Delivery filed Jun. 28, 2018.
Van Deutekom, et al., "Local dystrophin restoration with antisense oligonucleotide PRO051". New England Journal of Medicine (Dec. 27, 2007); 357(26): 2677-2686.
Venkatesan and Kim, "Peptide conjugates of oligonucleotides: synthesis and applications". Chemical Reviews (Sep. 13, 2006); 106(9): 3712-3761.
Vitiello, et al., "In vivo delivery of naked antisense oligos in aged mdx mice: analysis of dystrophin restoration in skeletal and cardiac muscle". Neuromuscular Disorders (Aug. 1, 2008); 18(8): 597-605. Epub Jul. 3, 2008.
Wang and Chou, "A thiol-ene coupling approach to native peptide stapling and macrocyclization". Angewandte Chemie International Edition (Sep. 7, 2015); 54(37): 10931-10934. Epub Jul. 17, 2015.
Warren, et al., "Advanced antisense therapies for postexposure protection against lethal filovirus infections". Nature Medicine (Sep. 2010); 16(9): 991-994. Epub Aug. 22, 2010.
Williams and Chaput, "Synthesis of peptide-oligonucleotide conjugates using a heterobifunctional crosslinker". In: Current Protocols in Nucleic acid Chemistry (Sep. 2010); 42(1): Unit 4.41, pp. 4.41.1-4.41.20, ISBN: 978-0-471-14270-6.
Wu, B., et al., "Dose-dependent restoration of dystrophin expression in cardiac muscle of dystrophic mice by systemically delivered morpholino". Gene Therapy (Jan. 2010); 17(1): 132-140.
Wu, B., et al., "Effective rescue of dystrophin improves cardiac function in dystrophin-deficient mice by a modified morpholino oligomer". Proceedings of the National Academy of Sciences (Sep. 30, 2008); 105(39): 14814-148149. Epub Sep. 19, 2008.
Wu, et al., "One-year treatment of morpholino antisense oligomer improves skeletal and cardiac muscle functions in dystrophio mdx mice". Molecular Therapy (Mar. 1, 2011); 19(3): 576-583. Epub Dec. 21, 2010.
Xiaoliang Wang, Applied Molecular Pharmacology, Peking Union Medical College Press (Sep. 2015); pp. 533-535, and Machine translation, 8 pages.
Helinski et al., Stitched a-helical peptides via bis ring-closing metathesis. J Am Chem Soc. Sep. 3, 2014;136 (35):12314-22. doi: 10.1021/ja505141j. Epub Aug. 21, 2014. Erratum in: J Am Chem Soc. Jul. 15, 2015;137(27):8858.
Kozlov et al., Efficient strategies for the conjugation of oligonucleotides to antibodies enabling highly sensitive protein detection. Biopolymers. Apr. 5, 2004;73(5):621-30.
Chu, Qian. "Towards Understanding Cell Penetration by Stapled Peptides." Med. Chem. Conunun., 2015, 6, pp. 111-119.
Margus H, Padari K, Pooga M. "Cell-penetrating peptides as versatile vehicles for oligonucleotide delivery." Mol Ther. Mar. 2012; 20( 3):525-33; Epub Jan. 10, 2012.
Munyendo WL, Lv H, Benza-Ingoula H, et al. "Cell penetrating peptides in the delivery of biopharmaceuticals." Biomolecules. 2012; 2(2): 187-202. Published Mar. 30, 2012.
SMCC, PubChem accessed Aug. 28, 2021 at URL: pubchem.ncbi.nlm.nih.gov/compound/125175, pp. 1-25 (2021).
DSG, PubChem accessed Aug. 28, 2021 at URL: pubchem.ncbi.nlm.nih.gov/compound/4432628, pp. 1-15 (2021).
Moulton et al., "Morpholinos and their peptide conjugates: Therapeutic promise and challenge for Duchenne muscular dystrophy," Biochimica et Biophysica Acta 1798: 2296-2303 (2010).
Archavala-Gomeza et al., "Comparative Analysis of Antisense Oligonucleotide Sequences for Targeted Skipping of Exon 51 During Dystrophin Pre-mRNA Splicing in Human Muscle," Human Gene Therapy 18:798-810 (2007).
Moulton et al., "Cellular Uptake of Antisense Morpholino Oligomers Conjugated to Arginine-Rich Peptides," Bioconjugate Chem. 15: 290-299 (2004).
Kim et al., Synthesis of all-hydrocarbon stapled a-helical peptides by ring-closing olefin metathesis, Nature Protocols 6: 761-771 ( 2011).
Lebleu et al., "Cell penetrating peptide conjugates of steric block oligonucleotides," Advanced Drug Delivery Reviews 60:517-529 ( 2008).
Walensky et al., Hydrocarbon-Stapled Peptides: Principles, Practice, and Progress, J. Med. Chem. 57:6275-6288 (epub Feb. 2014).
Notice of Reasons for Refusal dated Apr. 10, 2023 in Japanese Application No. 2023-014917.

Non-Cyclised peptide          RCM i,i+4

RCM i,i+4          Reduced RCM i,i+4

Compound VI

Compound VII

PMO*  PMO-CP8M*

1 μmol/kg

PMO*  PMO-CP8M*

7.6 μmol/kg

PMO  PMO-CP8M 10.9 μmol/kg

… (US 11,944,688 B2)

BIOLOGICALLY ACTIVE COMPOUNDS

RELATED APPLICATION

This application is a continuation of U.S. application Ser. No. 16/061,548 filed Jun. 12, 2018, which issued as U.S. Pat. No. 11,541,124, which is a national stage filing under 35 U.S.C. § 371 of International Patent Application Serial No. PCT/GB2016/054028, filed Dec. 21, 2016, which claims the benefit of priority to UK Application No. 1522548.5 filed Dec. 21, 2015, the contents of which is incorporated herein by reference in its entirety.

SEQUENCE STATEMENT

This application contains a Sequence Listing which has been submitted in XML format via EFS-Web and is hereby incorporated by reference in its entirety. Said XML copy, created on Dec. 16, 2022, is named Y9899_01002 SL.xml and is 418,510 bytes in size.

FIELD OF THE INVENTION

The present invention relates to improvements in drug delivery.

More particularly it relates to the use of Cell Penetrating Agents (CPA's), and more particularly still to the use of Cell Penetrating Peptides (CPP's) which have been stabilized by, for example: i) stapling two amino acids to form Stapled CPP's (StaP's) or ii) stitching three or more amino acids to form stitched CPP's (StiP's).

These stabilized CPP's are conjugated to a drug or Biologically Active Compound (BAC) directly or via a Bi-Functional Linker (BFL) so that the BAC can be carried though a cell membrane by the CPP. The resulting molecules are referred to as Drug Carrying Cell Penetrating Molecules (DCCPM's).

The preferred BAC's delivered in this manner are oligonucleotides (ON's), more preferably still electrically low charge carrying oligonucleotides (charge −3 to +3 at pH 7.5) and most preferably electrically neutral oligonucleotides (charge −1 to +1 at pH 7.5), such as, but not limited to, polynucleic acids (PNAs), phosphorodiamidate morpholino oligonucleotides (PMO's) or modified derivatives thereof.

The preferred BFL may be PEGylated, comprising poly ethylene glycol (PEG) groups including modifications such as an amine group, or incorporate a spacer, such as 13-Ala. These modifications can improve solubilisation or provide appropriate spacing between functional moieties.

The invention also relates to a method of facilitating the uptake of a BAC into a cell, the use of a DCCPM in the treatment of a disease requiring alteration of an endogenous or exogenous gene, a method of improving the bioavailability of a drug or BAC, a method of introducing a drug or BAC to a site which is refractory to the drug or BAC in its native state, a method of treating a subject comprising administering the DCCPM's of the invention and to a pharmaceutical composition comprising the DCCPM and one or more pharmaceutically acceptable excipients.

Still further aspects will be apparent from the detailed description.

BACKGROUND TO THE INVENTION n the treatment of all diseases it is desirable to deliver a drug or BAC into the body, and more preferably into a cell, at a target site, in a manner that ensures a maximal effect with minimal toxicity. This can be challenging.

An example of drugs or BACs which are delivered in a targeted manner are oligonucleotides (ON's), which term includes ON analogues.

ON's can target essential DNA, RNA and protein sequences and can modulate gene expression in a number of ways that includes steric blocking to suppress (i) RNA splicing, (ii) protein translation or (iii) other nucleic acid: nucleic acid or nucleic acid:protein interactions.

Specifically, the hybridisation of ON's to specific RNA sequence motifs prevents correct assembly of the spliceosome, so that it is unable to recognise the target exon(s) in the pre-mRNA and hence excludes these exon in the mature gene transcript. Exclusion of an in-frame exon can lead to a truncated yet functional gene product; exclusion of an out of frame exon results in a frame-shift of the transcript, potentially leading to a premature stop codon and a reduction in the target gene expression level.

Additionally, ON's can be designed to target 5' translation initiation start sites of viral gene transcript(s) to prevent binding of the translational machinery. Using antisense oligonucleotides (ASO) to suppress viral translation is a well-established technology[1] and has progressed into clinical trials for viral haemorrhagic fevers such as Marburg and Ebola[2,3].

Also, ON's can be designed to form aptamers such that the secondary and tertiary structures can bind proteins or other cellular targets thus impacting on specific gene expression levels or other cellular processes (e.g. post-translational modifications).

An advantage of steric blocking based suppression over that of siRNA/RNAi based RNase H-induction of the RNA Induced Silencing Complex is the reduced likelihood of off target side effects.

Modifications of an ON to produce a negatively charged backbone improve stability[4-7], but these backbone chemistries e.g. 2'O-Methyl Phosphothioate analogues, elicit membrane toxicity issues, cause thrombocytopaenia and injection site problems upon clinical translation[8], such that efficacy is prevented by toxicity issues, even when administration protocols become increasingly intermittent[9].

Indeed WO2013/150338 and WO 2014/053622 both disclose delivering negatively charged ON's of small size (typically smaller than 1.5 KDa) by complexing them with positively charged linear or stapled peptides of equal or greater than 15 amino acids and in the range of 15-27 amino acids.

JACS, Vol 136, 2014, GJ Hilnski et al, describe stapled and stitched peptides that are able to penetrate cells. Reference is made to the possibility that these peptides could be used to deliver an oligonucleotide, presumably in the same manner as disclosed in the international applications disclosed above, i.e. by complexation. There is nothing to suggest creating new entities of much larger size (greater than 1.5 KDa, through 2.5 KDa, 5 KDa, 7.5 KDa, 10 KDa, 12.5 KDa or more) by covalently linking a BAC with a CPA, optionally via a BFL and indeed, the prior methodology requires the respective components to have opposite charges to facilitate complexing.

The use of electrically low charge carrying oligonucleotides (charge −3 to +3 at pH 7.5) and most preferably electrically neutral oligonucleotides (charge −1 to +1 at pH 7.5), such as, but not limited to, polynucleic acids (PNAs), phosphorodiamidate morpholino oligonucleotides (PMO's), (covalently) conjugated directly or indirectly, using a BFL, was not apparent and indeed, limiting the charge on the ON further allows the use of smaller peptides (less than 15 amino acids in length, through 14, 13, 12, 11, 10, 9, 8, 7, 6 to as few as 4 or 5) as carriers.

The use of uncharged ON backbones, such as phosphorodiamidate morpholino oligonucleotides (PMOs), represent attractive BAC's as they have an impeccable safety record in a preclinical and clinical setting.[2,10-13]

However, their ability to penetrate cells and access their targets is compromised due to their uncharged nature[14].

Overcoming the problem of facilitating their entry into cells is therefore desirable.

Over the last 20 years much research has been dedicated to developing CPA's that facilitate delivery of drugs and BAC's to the biological site of action.

The approach has generally been to use charged peptides as non-covalent complexes to facilitate cell entry of a BAC. Conjugation has also been tried.

WO2014/064258 is an example of the existing conjugating art. A negatively charged ON is coupled to a targeting peptide via a linker. The targeting peptide is a receptor targeting moiety, and not a stapled or stitched peptide, and indeed considerable doubt exists as to whether DNA or RNA molecules can gain cell entry using a receptor targeting moiety as once a negatively charged ON is bound to such a moiety, non-covalent interactions alter its conformation[15].

WO89/03849 discloses oligonucleotide-polyamide conjugates. There is no disclosure of the use of stitched or stapled peptides. The methodology described uses oligonucleotides as a scaffold for the chain extension of peptides and not as a conjugate for delivery, per se.

WO2011/131693 describes nucleic acid constructs which contain a nucleic acid specific for a given target gene and a selective inhibitor of a neurotransmitter transporter. There is no disclosure of the use of stitched or stapled peptides as a delivery agent.

A peptide capable of effecting peptide-mediated cell delivery may also be referred to as a Cell Delivery Peptide (CDP). Examples include: poly arginine, penetratin (based upon an antennapedia homeodomain), or PMO internalization peptides (PIPs).

However, since their first description[16] and given that many CPPs contain multiple arginines, β-alanine and 6-aminohexanoic acid residues, (e.g. poly-Arg12, TAT, Penetratin, Pip6a) [database maintained at crdd.osdd.net/raghava/cpp-site/][17], it is surprising that no CPP-delivered drug has progressed through all phases of clinical trials. In part, this may be because the common arginine-rich core, which makes most CPP's effective, also causes membrane deformities[18] and in higher mammals this manifests as prohibitive toxic side effects, such as tubular degeneration of the kidney[19].

At a physiological pH, and based on pKa of amino acid R groups, a formal charge (FC) can be calculated based on the formula:

$$FC = V - N - \frac{B}{2}$$

Where, V=valence electrons of the neutral atom in isolation; N=the number of non-bonding valence electrons on the defined atom; B=the total number of electrons shared in bonds.

Indeed, based on this, the CPPs typically used to date harbour many positively charged residues. It has been shown that there is a correlation between this positive charge and membrane toxicity[20].

Therefore, CPPs with a lower amount of positively charged residues within the amino acid sequence, whilst retaining the ability to cross a biological membrane, will be more clinically relevant.

The Applicant has overcome this major impediment by utilising stabilized CPA's. By linking a drug or BAC to a stabilized CPA, including stitched and stapled peptides, they have surprisingly obtained enhanced cellular uptake dynamics, 10-20 fold better than current state of the art for CPA's[21,22].

They have illustrated this by delivering an ON targeted to repair a gene producing dystrophin. Targeting specific genes with ON is of course in itself known, as illustrated by, for example, WO2009/054725 and WO2010/123369. These publications however use a negatively charged backbone and deliver the cargo directly or using complexation.

One way to prepare stapled and stitched peptides, two linked amino acids (stapled) or three or more linked amino acids (stitched), is to incorporate amino acids into the peptide that are modified to bear e.g. an olefin (alkene) group (which may be incorporated at defined relative positions during solid-phase peptide synthesis). For example, on-resin ring-closing metathesis is then used to close one (stapled [denoted as StaP herein]) or two or more (stitched [denoted as StiP herein]) all-hydrocarbon cross-links that induce the peptide to adopt a stabilised structure, typically, but not essentially an alpha helix. For StaP's, it is preferred to use either one or both enantiomers of the un-natural amino acids, termed the S5 (S-pentenylalanine) or R5 (R-pentenylalanine), or the S8 (S-octenylalanine) or R8 (R-octenylalanine), depending on the stereo-chemical configuration. For StiP's, a further un-natural olefin-bearing α, α-di-substituted amino acid (B5 or B8) is utilised. Cross linking strategies are however not restricted to ring-closing metathesis of un-natural olefin-bearing a, α-di-substituted amino acids. Other cross-linking chemistry's may be used to stabilize the peptide, such as ring-closing metathesis between O-allylserine analogues (S-OAS or R-OAS).

The cellular entry dynamics of existing CPAs and the StiP's and StaP's differ. Traditional CPPs enter cells via energy-independent direct plasma membrane translocation or via energy-dependent, clathrin and caveolin-mediated endocytosis; whereas the StiP's and StaP's utilised in the invention enter via an energy dependent, but clathrin and caveolin independent mechanism[21,23]. Given that StiP's and StaP's uptake is abrogated with reduced cellular decoration of heparin sulphate[21] a macropinocytotic entry mechanism is infered[24], suggesting this altered entry mechanism enables enhanced cellular uptake and bio-distribution compared to the state of the art.

Relative to their unmodified peptide precursors, StaP's and StiP's generally exhibit robust cellular uptake, significant resistance to proteolytic degradation, and in vivo stability that can support a half-life of more than 12 hours in non-human primates[25]. It is likely that this increase in drug-likeness stems from the highly rigidified structure and the burial of the backbone amide bonds in the core of e.g. the α-helix. This structural rigidity also decreases the likelihood that StiP's and StaP's will be immunogenic, as the design of major histocompatibility complexes is such that peptides must adopt an extended conformation to be presented. The potential reduced or lack of membrane toxicity and immunogenicity enhances the clinical translatability of compounds when conjugated to drugs and BAC's such as ON's.

The BAC and CPP can be covalently conjugated directly, or covalently conjugated via a BFL. Many functional groups may be used for conjugation reactions.

ONs can be used to induce a steric block to any gene in humans, animals and lower order organisms and thus can be applied to natural disease (including genetic and age-related diseases) or acquired diseases in humans and animals.

For example, viral haemorrhagic fevers (VHFs) are animal-borne illnesses in which a prolonged inflammatory cytokine response leads to the gradual destruction of veins and arteries. Causes of VHF include Ebola and Marburg viruses and several Arena viruses; these diseases are presently considered untreatable. Viral haemorrhagic fevers are characterized by high fever and bleeding disorders, and can cause death by shock and organ failure. ASOs can be designed to target 5' translation initiation start sites of viral gene transcript(s) to prevent binding of the translational machinery. Using ASO to suppress viral translation is a well-established technology[1] and has progressed into clinical trials for viral haemorrhagic fevers such as Marburg and Ebola[2,3]. One PMO, AVI-7537 was evaluated for human use in the West African Ebola outbreak in 2014-15.

Some tissues are particularly refractory to naked PMO transfection, e.g. heart, which may reflect differential vesicle-mediated PMO uptake mechanisms[23]. In fact, direct intra-cardiac injection of naked PMO does not even lead to efficient transfection[26], and refractory tissues tend to require repeat administration or high dose strategies[27-29]. However, whilst CPP conjugation improves PMO bio-distribution and serum stability[30-32], toxicity is still a major roadblock for pipeline development[19].

For effective clinical translation of steric blocking ASOs, CPPs need to effectively deliver the BAC to either the cytoplasm or nucleoplasm whilst limiting any toxicity associated with cell entry.

Thus, providing DCCPM's which are able to deliver a drug or BAC more efficiently or to a target site, or with lower toxicity and immunogenicity would be highly desirable.

BRIEF SUMMARY OF THE DISCLOSURE

In accordance with a first aspect of the present invention there is provided a drug carrying cell penetrating molecule (DCCPM) comprising:
i. a biologically active compound (BAC), and
ii. a cell penetrating agent (CPA), which BAC and CPA are linked directly or via a bi-functional linker (BFL), and wherein the CPA is a stabilized peptide (CPP) which has a conformation imposed upon it by stapling to form a stapled peptide (StaP) or stitching to form a stitched peptide (StiP).

A stapled peptide (StaP) may be formed by, for example, stapling two conformationally adjacent amino acids together, and a stitched peptide (StiP) may be formed by, for example, stitching at least three conformationally adjacent amino acids to form a stitched peptide (StiP).

The stapling or stitching results in the formation of a cross link or bridge between two conformationally adjacent amino acids of the peptide.

In a preferred embodiment the cross link or bridge comprises two components, a hydrocarbon bridge and a terminal methyl group. The hydrocarbon bridge may be composed of a double hydrocarbon bond or a single hydrocarbon bond.

The CPP preferably comprises at least two un-natural amino acids bearing all-hydrocarbon tethers (e.g. α-methyl, α-pentenyl glycine).

The preferred stapled or stitched CPPs incorporate one or more of: a (S)-pentenylalanine (S5) or its enantiomer (R5), a S-octenylalanine (S8) or its enantiomer (R8) or combinations thereof (e.g R-octenylalanine/S-pentenylalanine (R8/S5) or S-octenylalanine/R-pentenylalanine (S8/R5).

The preferred unnatural amino acids incorporated into the CPPs and reacted to form a cross link or bridge between them are illustrated in Table 1 and some exemplary and preferred resulting CPPs are illustrated in Table 2.

TABLE 1

Unnatural Amino Acids

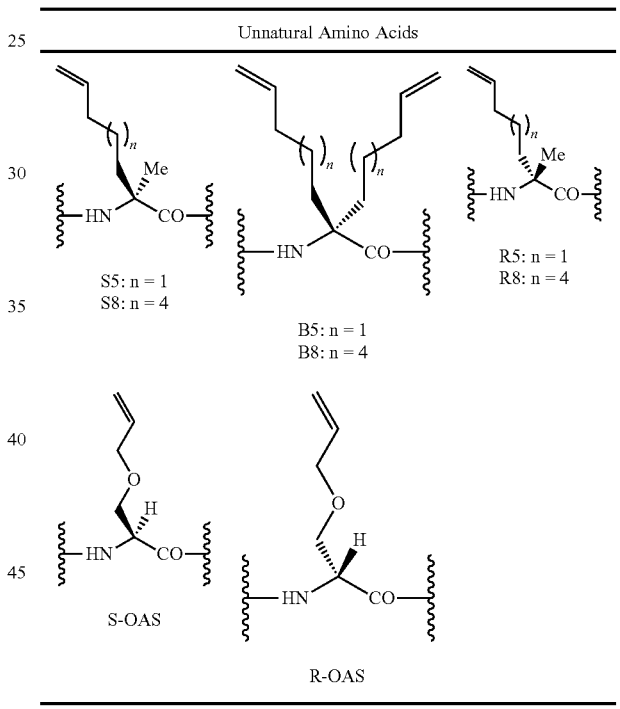

TABLE 2

| SEQ ID NO: | Peptide Sequence | Length | Peptide Type |
|---|---|---|---|
| 3 | TRQARRNRRRWRRAAAA | 18 | Non RCM |
| 4 | TRQARRNRRRWRERQR | 17 | Non RCM |
| 5 | RQIKIWFQNRRMKWKK | 16 | Non RCM |
| 6 | RRRRRRRWRRR | 12 | Non RCM |
| 7 | LSQETFSDLWKLLPEN | 16 | Non RCM |
| 8 | NQLKRSFFALRDQI | 14 | Non RCM |

TABLE 2-continued

| SEQ ID NO: | Peptide Sequence | Length | Peptide Type |
|---|---|---|---|
| 8 | NQLKRSFFALRDQI | 14 | Non RCM |
| 9 | TILKASVDYIRKLQREQQRAKEL | 23 | Non RCM |
| 6 | RRRRRRRWRRR | 12 | Non RCM |
| 10 | RRRRRRRRRRR | 12 | Non RCM |
| 11 | YGRKKRRQRRRP | 12 | Non RCM |
| 12 | RKFKRLFQ | 8 | Non RCM |
| 13 | NELKRSFFALRDQI | 14 | Non RCM |
| 14 | NQL-R8-RS-FFAL-S5-DQI | 14 | Non RCM |
| 15 | KNHTHQQDI | 9 | Non RCM |
| 16 | NELKRSFFALRDQIPSLQGEKASRAQILDKATEYIQYNLRRK | 42 | Non RCM |
| 17 | KATEYIQYNLRRKNHTHQQDIDDL | 24 | Non RCM |
| 18 | ASTLFETFYLGGLLG | 15 | Non RCM |
| 19 | RRGSRPSGA-S5-RRR-S5-R | 15 | Non RCM |
| 20 | FNINDRIKELGTLI | 14 | Non RCM |
| 21 | DHIKDSFHSLRDSVPSLQGEKASRAQILDKATEYIQYNLRRK | 42 | Non RCM |
| 22 | EYIQYNLRKNHTHQQDIDDLKRQNALLEQQVRALGG | 36 | Non RCM |
| 23 | SSLFERFYNLVTPAGG | 16 | Non RCM |
| 24 | NSSFADFFHTVPYNLL | 16 | Non RCM |
| 25 | TRQARRN-S5-RRR-S5-RR | 14 | Non RCM |
| 26 | RRGSRPSGA-S5-RRR-S5-RAAAA | 19 | i, i + 4 Staple |
| 27 | S5-RRQ-S5-RRDRQRRRRR | 15 | i, i + 4 Staple |
| 28 | TRQ-S5-RRQ-S5-RRRWRERQR | 17 | i, i + 4 Staple |
| 29 | SEELV-S5-EAH-S5-LCTLLENAIQDTVREQ | 26 | i, i + 4 Staple |
| 30 | SEELVAEAH-S5-LCT-S5-LENAIQDTVREQ | 26 | i, i + 4 Staple |
| 31 | SEELVAEAHNLCTLLE-S5-AIQ-S5-TVREQ | 26 | i, i + 4 Staple |
| 32 | DRRQRRR-S5-RQR-S5-RRR | 15 | i, i + 4 Staple |
| 33 | S5-RRQ-S5-RRRRQRRRRR | 15 | i, i + 4 Staple |
| 34 | S-S5-ELV-S5-EAHNLCTLLENAIQDTVREQ | 26 | i, i + 4 Staple |
| 35 | SEELVAEA-S5-NLC-S5-LLENAIQDTVREQ | 26 | i, i + 4 Staple |
| 36 | SEELVAEAHNLC-S5-LLE-S5-AIQDTVREQ | 26 | i, i + 4 Staple |
| 37 | SEELVAEAHNLCTLLENAI-S5-DTV-S5-EQ | 26 | i, i + 4 Staple |
| 38 | FS-S5-LWK-S5-L | 8 | i, i + 4 Staple |
| 39 | FM-S5-YWK-S5-L | 8 | i, i + 4 Staple |
| 40 | QTFS-S5-LWK-S5-L | 10 | i, i + 4 Staple |
| 41 | PPKKFR-S5-LFF-S5-S | 12 | i, i + 4 Staple |
| 42 | KK-pff-R-S5-LFF-S5-S | 10 | i, i + 4 Staple |
| 43 | RK-pff-S5-RLF-S5-SY | 10 | i, i + 4 Staple |

TABLE 2-continued

| SEQ ID NO: | Peptide Sequence | Length | Peptide Type |
|---|---|---|---|
| 44 | RKF-S5-RLF-S5-SY | 10 | i, i + 4 Staple |
| 45 | R-pff-K-S5-RLF-S5-SY | 10 | i, i + 4 Staple |
| 46 | AM-S5-YWK-S5-L | 8 | i, i + 4 Staple |
| 47 | QTFSD-R5-WK-S5-L | 10 | i, i + 4 Staple |
| 48 | KKFR-S5-LFF-S5-S | 10 | i, i + 4 Staple |
| 49 | RRLFR-S5-NLFL-S5-T | 12 | i, i + 4 Staple |
| 50 | RR-pff-S5-RLF-S5-SY | 10 | i, i + 4 Staple |
| 51 | RKA-S5-RLF-S5-SY | 10 | i, i + 4 Staple |
| 43 | RK-pff-S5-RLF-S5-SY | 10 | i, i + 4 Staple |
| 52 | S5-RLF-S5-SY | 7 | i, i + 4 Staple |
| 53 | KQKRKFS-S5-FFK-S5-L | 13 | i, i + 4 Staple |
| 54 | KQKRK-pff-S-S5-FFK-S5-L | 13 | i, i + 4 Staple |
| 54 | KQKRK-pff-S-S5-FFK-S5-L | 13 | i, i + 4 Staple |
| 55 | KF-S5-RLF-S5 | 7 | i, i + 4 Staple |
| 56 | S5-RLF-S5 | 5 | i, i + 4 Staple |
| 57 | RKF-S5-RLF-S5 | 8 | i, i + 4 Staple |
| 58 | KQKRKFS-S5-FFK-S5-LV | 13 | i, i + 4 Staple |
| 59 | KQ-pff-RKKS-S5-FFK-S5-L | 13 | i, i + 4 Staple |
| 60 | RK-pff-S5-RLF-S5 | 8 | i, i + 4 Staple |
| 61 | F-S5-RLF-S5 | 6 | i, i + 4 Staple |
| 62 | KTYRGAFQ-S5-LFQ-S5-VRE | 16 | i, i + 4 Staple |
| 63 | STALR-S5-LIE-S5-LVNITQNQKAPL | 22 | i, i + 4 Staple |
| 64 | STALRELI-S5-ELV-S5-ITQNQKAPL | 22 | i, i + 4 Staple |
| 65 | STALRELIEEL-S5-NIT-S5-NQKAPL | 22 | i, i + 4 Staple |
| 66 | NELK-S5-SFF-S5-LRDQIPELENNEKAP | 24 | i, i + 4 Staple |
| 67 | LENRQ-S5-KLE-S5-ANRHLL | 16 | i, i + 4 Staple |
| 68 | IL-S5-ASV-S5-YIRKLQREQ | 16 | i, i + 4 Staple |
| 69 | FNI-S5-DRI-S5-ELGTLI | 14 | i, i + 4 Staple |
| 70 | KN-S5-THQ-S5-DI | 9 | i, i + 4 Staple |
| 71 | STALRELIEE LV-S5-ITQ-S5-QKAPL | 21 | i, i + 4 Staple |
| 72 | NELK-S5-SFF-S5-LRDQI | 14 | i, i + 4 Staple |
| 73 | LENRQKKLE-S5-ANR-S5-LL | 16 | i, i + 4 Staple |
| 74 | ILKAS-S5-DYI-S5-KLQREQ | 16 | i, i + 4 Staple |
| 75 | DHIK-S5-SFH-S5-LRDSV | 14 | i, i + 4 Staple |
| 76 | DHIKDSF-S5-SLR-S5-SV | 14 | i, i + 4 Staple |
| 77 | S5-YIQ-S5-NLRRKNHTHQQDIDDLLKRQNALLEQQVRALGG | 38 | i, i + 4 Staple |
| 78 | TYRGAAQ-S5-AAQ-S5-VREV | 16 | i, i + 4 Staple |
| 79 | TY-S5-GAF-S5-NLFQSVREV | 16 | i, i + 4 Staple |

TABLE 2-continued

| SEQ ID NO: | Peptide Sequence | Length | Peptide Type |
|---|---|---|---|
| 80 | A-S5-SVF-S5-NYFHSVPYFEL | 17 | i, i + 4 Staple |
| 81 | GAF-S5-NLF-S5-SV | 10 | i, i + 4 Staple |
| 82 | S5-GAF-S5-NLF-R5-SV | 11 | i, i + 4 Staple |
| 83 | SYRGAFQ-S5-LFQ-S5-VREV | 16 | i, i + 4 Staple |
| 84 | SSVFY-S5-YFH-S5-VPYFEL | 16 | i, i + 4 Staple |
| 85 | A-S5-TLF-S5-TFYLGGLLG | 15 | i, i + 4 Staple |
| 86 | S5-GAF-S5-NLFQSV | 11 | i, i + 4 Staple |
| 87 | A-S5-SSF-S5-DFFHTVPYNLL | 17 | i, i + 4 Staple |
| 88 | ERLRRRI-S5-LCR-S5-HHST | 16 | i, i + 4 Staple |
| 89 | ERLRRRI-S5-NLCR-S5-HHST | 17 | i, i + 4 Staple |
| 90 | ERLRRRL-S5-LCR-S5-HHST | 16 | i, i + 4 Staple |
| 91 | ERLRRRF-S5-LCR-S5-HHST | 16 | i, i + 4 Staple |
| 92 | ERFRRRI-S5-LCR-S5-HHST | 16 | i, i + 4 Staple |
| 93 | ERLARRI-S5-LCR-S5-HHST | 16 | i, i + 4 Staple |
| 94 | ENPESILD-S5-HVQ-S5-VM | 15 | i, i + 4 Staple |
| 95 | PE-S5-ILD-S5-HVQRVM | 13 | i, i + 4 Staple |
| 96 | ERLRRRI-S5-FCR-S5-HHST | 16 | i, i + 4 Staple |
| 97 | ERLRRRNL-S5-LCR-S5-HHST | 17 | i, i + 4 Staple |
| 98 | ERNLRRRI-S5-LCR-S5-HHST | 17 | i, i + 4 Staple |
| 99 | ERWRRRI-S5-LCR-S5-HHST | 16 | i, i + 4 Staple |
| 100 | RELRREI-S5-LCR-S5-HHST | 16 | i, i + 4 Staple |
| 101 | ENPE-S5-ILD-S5-HVQRVM | 15 | i, i + 4 Staple |
| 102 | NPE-S5-ILD-S5-HVQRVM | 14 | i, i + 4 Staple |
| 103 | WPE-S5-ILD-S5-HVQRVM | 14 | i, i + 4 Staple |
| 104 | PE-S5-ILD-S5-HVRRVMR | 14 | i, i + 4 Staple |
| 105 | RPE-S5-ILD-S5-HVRRVMR | 15 | i, i + 4 Staple |
| 106 | TRQA-R8-RNRRRR-S5-RR | 14 | i, i + 7 Staple |
| 107 | RRGSRPSGA-R8-RRRRRA-S5 | 17 | i, i + 7 Staple |
| 108 | RRGSRPSGA-R8-RRRRRA-S5-AA | 19 | i, i + 7 Staple |
| 109 | TRQARRN-R8-RRRWRE-S5-QR | 17 | i, i + 7 Staple |
| 110 | RRRR-R5-RRRWRR-S8 | 12 | i, i + 7 Staple |
| 111 | KPE-S5-ILD-S5-HVQRVM | 14 | i, i + 7 Staple |
| 112 | WPE-S5-ILD-S5-HVRRVMR | 15 | i, i + 7 Staple |
| 113 | RRRR-R8-RQRRRR-S5-RR | 14 | i, i + 7 Staple |
| 114 | RRGSRPSGA-R8-RRRRRR-S5 | 17 | i, i + 7 Staple |
| 115 | R8-RRQRRR-S5-RQRRRRR | 15 | i, i + 7 Staple |
| 109 | TRQARRN-R5-RRRWRE-S8-QR | 17 | i, i + 7 Staple |
| 116 | RRRR-R5-RRRRRR-S8 | 12 | i, i + 7 Staple |

TABLE 2-continued

| SEQ ID NO: | Peptide Sequence | Length | Peptide Type |
|---|---|---|---|
| 117 | YGRK-R5-RRQRRR-S8 | 12 | i, i + 7 Staple |
| 118 | S-R8-ELVAEA-S5-NLCTLLENAIQDTVREQ | 25 | i, i + 7 Staple |
| 119 | SEELVAEAH-R8-LCTLLE-S5-AIQDTVREQ | 26 | i, i + 7 Staple |
| 120 | SEELVAEAHNLCT-R8-LENAIQ-S5-TVREQ | 26 | i, i + 7 Staple |
| 121 | RQIKIW-R5-QNRRMK-S8-KK | 16 | i, i + 7 Staple |
| 110 | RRRR-R5-RRRWRR-S8 | 12 | i, i + 7 Staple |
| 118 | S-R8-ELVAEA-S5-NLCTLLENAIQDTVREQ | 26 | i, i + 7 Staple |
| 122 | SE-R8-LVAEAH-S5-LCTLLENAIQDTVREQ | 26 | i, i + 7 Staple |
| 123 | SEELVAEAHNLC-R8-LLENAI-S5-DTVREQ | 26 | i, i + 7 Staple |
| 124 | SEELVAEAHNLCTLLE-R8-AIQDT V-S5-EQ | 26 | i, i + 7 Staple |
| 125 | LSQETF-R8-DLWKLL-S5-EN | 16 | i, i + 7 Staple |
| 126 | ILR-R8-AVSHMK-S5-LRGT | 15 | i, i + 7 Staple |
| 126 | ILR-R8-AVSHMK-S5-LRGT | 15 | i, i + 7 Staple |
| 127 | NEL-R8-RS FRSL-S5-DSI | 14 | i, i + 7 Staple |
| 128 | NEL-R8-RS FRAL-S5-DQI | 14 | i, i + 7 Staple |
| 129 | NEL-R8-RS FFAL-S5-DSI | 14 | i, i + 7 Staple |
| 130 | NEL-R8-RS FFAL-S5-DQI | 14 | i, i + 7 Staple |
| 131 | IL-R8-MA-VSHM-S5-SLRGT | 15 | i, i + 7 Staple |
| 132 | NEL-R8-RS FRAL-S5-DSI | 14 | i, i + 7 Staple |
| 133 | NEL-R8-RS FFSL-S5-DQI | 14 | i, i + 7 Staple |
| 134 | WNEL-R8-RSFRSL-S5-DQI | 15 | i, i + 7 Staple |
| 135 | NQR-R8-LSFFAL-S5-DQI | 14 | i, i + 7 Staple |
| 14 | NQL-R8- RSFFAL-S5-DQI | 14 | i, i + 7 Staple |
| 135 | NQR-R8- LSFFAL-S5-DQI | 14 | i, i + 7 Staple |
| 136 | NQL-R8- LSFFAR-S5-DQI | 14 | i, i + 7 Staple |
| 137 | NKL-R8-RS FFAL-S5-DQI | 14 | i, i + 7 Staple |
| 130 | NEL-R8-RS FFAL-S5-DQI | 14 | i, i + 7 Staple |
| 138 | NELK-R8-SFFALR-S5-QIPELENNEKAP | 24 | i, i + 7 Staple |
| 139 | AHL-R8- LCLEKL-S5-GLV | 14 | i, i + 7 Staple |
| 194 | NQL-R8-RSFFAL-S5-DQI (D-amino acids) | 14 | i, i + 7 Staple |
| 191 | IQD-S5-LAFFSR-R8-LQN (D-amino acids) | 14 | i, i + 7 Staple |
| 140 | NKL-R8-RS-FKAL-S5-KQI | 14 | i, i + 7 Staple |
| 141 | NELK-R8-S-FFALR-S5-QI | 14 | i, i + 7 Staple |
| 142 | NQL-R8-RS-FFAL-S5-DQIPELENNEKAP | 24 | i, i + 7 Staple |
| 14 | NQL-R8-RSFFAL-S5-DQI | 14 | i, i + 7 Staple |
| 192 | AHL-R8-LCLEKL-S5-GLV-(K-(PEG)1- | 15 | i, i + 7 Staple |
| 143 | KV-R8-ILK KAT-S5-YILS | 14 | i, i + 7 Staple |
| 144 | R8-KR RAHA-S5-AERARR | 14 | i, i + 7 Staple |
| 191 | IQD-S5-LAFFSR-R8-LQN (D-amino acids) | 14 | i, i + 7 Staple |

TABLE 2-continued

| SEQ ID NO: | Peptide Sequence | Length | Peptide Type |
|---|---|---|---|
| 194 | NQL-R8-RSFFAL-S5-DQI (D-amino acids) | 14 | i, i + 7 Staple |
| 14 | NQL-R8-RS-FFAL-S5-DQI | 14 | i, i + 7 Staple |
| 14 | NQL-R8-RSFFAL-S5-DQI | 14 | i, i + 7 Staple |
| 145 | EENAKRR-R8-HNALER-S5-RR | 17 | i, i + 7 Staple |
| 193 | NQL-R8-FSRFAL-S5-DQI (D-amino acids) | 14 | i, i + 7 Staple |
| 146 | NQL-R8-LS-S5-DQI | 10 | i, i + 7 Staple |
| 147 | NQL-R8-FS-S5-DQI | 10 | i, i + 7 Staple |
| 148 | TILKASVDYI RKL-R8-REQQRA-S5-EL | 23 | i, i + 7 Staple |
| 149 | FNI-R8-DRI-S5-TLI | 11 | i, i + 7 Staple |
| 150 | RNI-R8-DRI-S5-TRI | 11 | i, i + 7 Staple |
| 151 | KATEYIQYNLRRKN-R8-THQQDI-S5-DL | 24 | i, i + 7 Staple |
| 152 | NEL-R8-RSFFAL-S5-DQIDQIPAAKRVKLD | 26 | i, i + 7 Staple |
| 14 | NQL-R8-RSFFAL-S5-DQI | 14 | i, i + 7 Staple |
| 153 | RNI-R8-DRIKEL-S5-TLI | 14 | i, i + 7 Staple |
| 154 | FNIN-R8-RIKELG-S5-LI | 14 | i, i + 7 Staple |
| 155 | FNI-R8-DRIKEL-S5-TRI | 14 | i, i + 7 Staple |
| 156 | NQL-R8-RS FRAL-S5-DQI | 15 | i, i + 7 Staple |
| 157 | NEL-R8-RSFFAL-S5-DQIDQIPKKKRKV | 24 | i, i + 7 Staple |
| 158 | ENPE-R8-ILDEHV-S5-RVM | 15 | i, i + 7 Staple |
| 164 | S8-RQARRN-B5-RRRWRE-S8-QR | 16 | i, i + 4, i + 11 Stitch Reduced |
| 163 | TRQ-S5-RRN-B5-RRRWRE-S8-QR | 17 | i, i + 4, i + 11 Stitch |
| 159 | TRQ-S5-RRA-B5-RRRWRE-S8-QR | 17 | i, i + 4, i + 11 Stitch |
| 160 | S5-RRN-B5-RRRWRE-S8 | 12 | i, i + 4, i + 11 Stitch |
| 161 | EYIQ-R5-NLRRKNH-S8-HQQDIDDLKRQNALLEQQVRALGG | 37 | i, i + 4, i + 11 Stitch |
| 165 | S8-RQARRQ-B5-RRRWRE-S8-QR | 17 | i, i + 4, i + 11 Stitch Reduced |
| 162 | TRQ-S5-Q-B5-RRRWRE-S8-QR | 15 | i, i + 4, i + 11 Stitch |
| 163 | TRQ-S5-RRN-B5-RRRWRE-S8-QR | 17 | i, i + 4, i + 11 Stitch Reduced |
| 164 | R8-RQARRN-B5-RRRWRE-S8-QR | 17 | i, i + 4, i + 11 Stitch Reduced |
| 165 | R8-RQARRQ-B5-RRRWRE-S8-QR | 17 | i, i + 4, i + 11 Stitch |
| 166 | S5-RRN-B5-RRRWRR-S8 | 12 | i, i + 4, i + 11 Stitch |
| 167 | RRA-B5-RRRWRR-S8 | 11 | i, i + 4, i + 11 Stitch |
| 169 | S5-RRR-B5-RRRRRR-S8 | 12 | i, i + 4, i + 11 Stitch |
| 168 | S5-KIW-B5-QNRRNLK-S8 | 13 | i, i + 4, i + 11 Stitch |
| 169 | S5-RRR-B5-RRRRRR-S8 | 12 | i, i + 4, i + 11 Stitch |
| 170 | S5-GRK-B5-RRQRRR-S8 | 12 | i, i + 4, i + 11 Stitch |
| 171 | S5-RRQ-B5-RRRWRR-S8 | 12 | i, i + 4, i + 11 Stitch |

TABLE 2-continued

| SEQ ID NO: | Peptide Sequence | Length | Peptide Type |
|---|---|---|---|
| 174 | S5-RRR-B5-RRRWRR-S8 | 12 | i, i + 4, i + 11 Stitch |
| 172 | RQ-S5-KIW-B5-QNRRMK-S8-KK | 16 | i, i + 4, i + 11 Stitch |
| 173 | S5-KIW-B5-QNRRAK-S8 | 12 | i, i + 4, i + 11 Stitch |
| 174 | S5-RRR-B5-RRRWRR-S8 | 12 | i, i + 4, i + 11 Stitch |
| 175 | L-S5-ILQ-B5-AVQVIL-S8-LEQQVRER | 21 | i, i + 4, i + 11 Stitch |
| 176 | LLILQQAV-S5-VIL-B5-LEQQVR-S8-R | 21 | i, i + 4, i + 11 Stitch |
| 182 | S5-DFS-B5-YWK-R5-L | 10 | i, i + 4, i + 11 Stitch |
| 177 | LS-S5-ETF-B8-DLWKLL-S8-EN | 16 | i, i + 4, i + 11 Stitch |
| 178 | LSQ-S5-TFS-B8-LWKLLA-S8-N | 16 | i, i + 4, i + 11 Stitch |
| 179 | L-S5-ILQ- B5-AVQ-R5-ILGLEQQVRER | 21 | i, i + 4, i + 11 Stitch |
| 180 | LLILQQAV-S5-VIL-B5-LEQ-R5-VRER | 21 | i, i + 4, i + 11 Stitch |
| 181 | LLIL-S5-QAV-B5-VIL-R5-LEQQVRER | 21 | i, i + 4, i + 11 Stitch |
| 182 | R5-DFS-B5-YWK-S5-L | 10 | i, i + 4, i + 11 Stitch |
| 183 | LS-S5-ETA-B8-DLWKLL-S8-EN | 16 | i, i + 4, i + 11 Stitch |
| 184 | EDIIRNIA-S5-HLA-B5-VGDWNLD-S8-SI | 23 | i, i + 4, i + 11 Stitch |
| 185 | NIA-S5-HLA-B5-VGDWNLD- S8-SI (isomer 2) | 18 | i, i + 4, i + 11 Stitch |
| 186 | S5-HLA-B5-VGDWNLD-S8 (isomer 1) | 13 | i, i + 4, i + 11 Stitch |
| 187 | NVKRR-R8-HNVLER-S5-RRNEL-R8-RSFFAL-S5-DQI | 29 | i, i + 4, i + 11 Stitch |
| 188 | S5-YIQ-B5-NLRRKNH-S8-HQQDIDDLLKRQNALLEQQVRALGG | 38 | i, i + 4, i + 11 Stitch |
| 185 | NIA-S5-HLA-B5-VGDWNLD-S8-SI | 18 | i, i + 4, i + 11 Stitch |
| 189 | NIA-S5-HLA-B5-VGDWNLD-S8 | 16 | i, i + 4, i + 11 Stitch |
| 186 | S5-HLA-B5-VGDWNLD-S8 | 13 | i, i + 4, i + 11 Stitch |
| 190 | EYIQYNLR-S5-KNH-B5-HQQDID-S8-LKRQNALLEQQVRALGG | 37 | i, i + 4, i + 11 Stitch |

S5 = a-methyl, a-alkenylglycine with 5 carbon chain
S8 = a-methyl, a-alkenylglycine with 8 carbon chain
B5 = a-methyl, a-alkenylglycine with two 5 carbon chain Alternative CPPs and their method of manufacture are disclosed in Chu et al, 2014 and associated supplementary information, and are incorporated by reference[21].

The exemplified stabilized peptide comprises two or more olefin bearing side chains that are covalently formed, typically by means of a ring-closing metathesis.

The stabilized conformation typically comprises at least one alpha helix. It may however, in the alternative, comprise at least one turn (for example, but not limited to, α, β, γ, δ or π), several turns to form a beta sheet, or a combination of one or more of: an alpha helix, turn, or beta sheet.

The formal charge of a CPP is calculated at physiological pH (about 7.5) and is based on the pKa of amino acid R groups. These values ($pK_x$) are represented in Table 3.

TABLE 3

| Name | 3-Letter Symbol | 1-Letter Symbol | Molecular Weight | Molecular Formula | Residue Formula | Residue Weight (—H2O) | pKa1 | pKb2 | pKx3 | pI4 |
|---|---|---|---|---|---|---|---|---|---|---|
| Alganine | Ala | A | 89.10 | $C_3H_7NO_2$ | $C_3H_5NO$ | 71.08 | 2.34 | 9.69 | — | 6.00 |
| Arginine | Arg | R | 174.20 | $C_6H_{14}N_4O_2$ | $C_6H_{12}N_4O$ | 156.19 | 2.17 | 9.04 | 12.48 | 10.76 |
| Asparagine | Asn | N | 132.12 | $C_4H_8N_2O_3$ | $C_4H_6N_2O_2$ | 114.11 | 2.02 | 8.80 | — | 5.41 |
| Aspartic Acid | Asp | D | 133.11 | $C_4H_7NO_4$ | $C_4H_5NO_3$ | 115.09 | 1.88 | 9.60 | 3.65 | 2.77 |
| Cysteine | Cys | C | 121.16 | $C_3H_7NO_2S$ | $C_3H_5NOS$ | 103.15 | 1.96 | 10.28 | 8.18 | 5.07 |
| Glutamic acid | Glu | E | 147.13 | $C_5H_9NO_4$ | $C_5H_7NO_3$ | 129.12 | 2.19 | 9.67 | 4.25 | 3.22 |
| Glutamine | Gln | Q | 146.15 | $C_5H_{10}N_2O_3$ | $C_5H_8N_2O_2$ | 128.13 | 2.17 | 9.13 | — | 5.65 |

TABLE 3-continued

| Name | 3-Letter Symbol | 1-Letter Symbol | Molecular Weight | Molecular Formula | Residue Formula | Residue Weight (—H2O) | pKa1 | pKb2 | pKx3 | pI4 |
|---|---|---|---|---|---|---|---|---|---|---|
| Glycine | Gly | G | 75.07 | $C_2H_5NO_2$ | $C_2H_3NO$ | 57.05 | 2.34 | 9.60 | — | 5.97 |
| Histidine | His | H | 155.16 | $C_6H_9N_3O_2$ | $C_6H_7N_3O$ | 137.14 | 1.82 | 9.17 | 6.00 | 7.59 |
| Hydroxyproline | Hyp | O | 131.13 | $C_5H_9NO_3$ | $C_5H_7NO_2$ | 113.11 | 1.82 | 9.65 | — | — |
| Isoleucine | Ile | I | 131.18 | $C_6H_{13}NO_2$ | $C_6H_{11}NO$ | 113.16 | 2.36 | 9.60 | — | 6.02 |
| Leucine | Leu | L | 131.18 | $C_6H_{13}NO_2$ | $C_6H_{11}NO$ | 113.16 | 2.36 | 9.60 | — | 5.98 |
| Lysine | Lys | K | 146.19 | $C_6H_{14}N_2O_2$ | $C_6H_{12}N_2O$ | 128.18 | 2.18 | 8.95 | 10.53 | 9.74 |
| Methionine | Met | M | 149.21 | $C_5H_{11}NO_2S$ | $C_5H_{11}NOS$ | 131.20 | 2.28 | 9.21 | — | 5.74 |
| Phenylalanine | Phe | F | 165.19 | $C_9H_{11}NO_2$ | $C_9H_9NO$ | 147.18 | 1.83 | 9.13 | — | 5.48 |
| Proline | Pro | P | 115.13 | $C_5H_9NO_2$ | $C_5H_7NO$ | 97.12 | 1.99 | 10.60 | — | 6.30 |
| Pyroglutamatic | Glp | U | 139.11 | $C_5H_7NO_3$ | $C_5H_5NO_2$ | 121.09 | — | — | — | 5.68 |
| Serine | Ser | S | 105.09 | $C_3H_7NO_3$ | $C_3H_5NO_2$ | 87.08 | 2.21 | 9.15 | — | 5.68 |
| Threonine | Thr | T | 119.12 | $C_4H_9NO_3$ | $C_4H_7NO_2$ | 101.11 | 2.09 | 9.10 | — | 5.60 |
| Tryptophan | Trp | W | 204.23 | $C_{11}H_{12}N_2O_2$ | $C_{11}H_{10}N_2O$ | 186.22 | 2.83 | 9.39 | — | 5.89 |
| Tyrosine | Tyr | Y | 181.19 | $C_9H_{11}NO_3$ | $C_9H_9NO_2$ | 163.18 | 2.20 | 9.11 | 10.07 | 5.66 |
| Valine | Val | V | 117.15 | $C_5H_{11}NO_2$ | $C_5H_9NO$ | 99.13 | 2.32 | 9.62 | — | 5.96 |

1$pK_a$ is the negative of the logarithm of the dissociated constant for the-COOH group
2$pK_b$ is the negative of the logarithm of the dissociated constant for the-$NH_3^+$ group
3$pK_x$ is the negative of the logarithm of the dissociated constant for any other group in the molecule
4pI is the pH at the isoelectric point
References: D. R. Lide, *Handbook of Chemistry and Physics*, *72nd Edition*, CRC Press, Boca Raton, FL, 1991.

CPPs typically used to date harbour many positively charged residues. Reducing the amount of positively charged residues within the amino acid sequence, whilst retaining the ability to cross a biological membrane, will be more clinically relevant.

Accordingly, it is possible to reduce the charge on the peptide sequences illustrated in Table 2.

The preferred BAC is an oligonucleotide (ON), more preferably still an anti-sense oligonucleotide (AON). Different anti-sense oligonucleotide chemistries are illustrated in Table 4, with the use of low charge or neutral charged chemistries, such as, phosphorodiamidate morpholino oligonucleotides (PMOs) being preferred.

TABLE 4

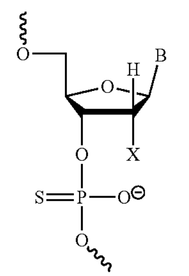

Phosphorothioate (PS)

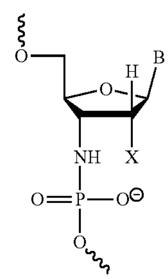

N'3 Phosphoramidite (NP)

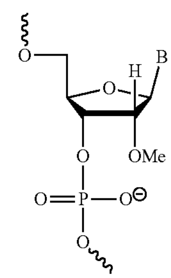

2'-O-Methyl (2' O-Me)

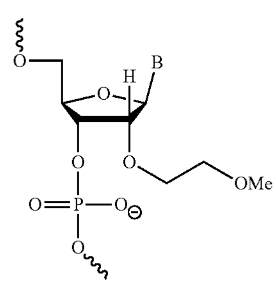

2'-O-Methoxyethyl (MOE)

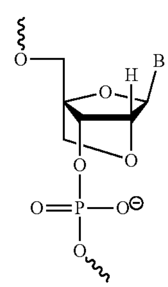

Locked Nucleic Acid (LNA)

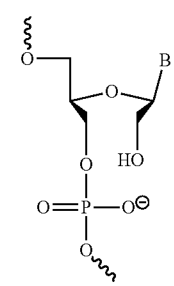

Unlocked Nucleic Acid (UNA)

TABLE 4-continued

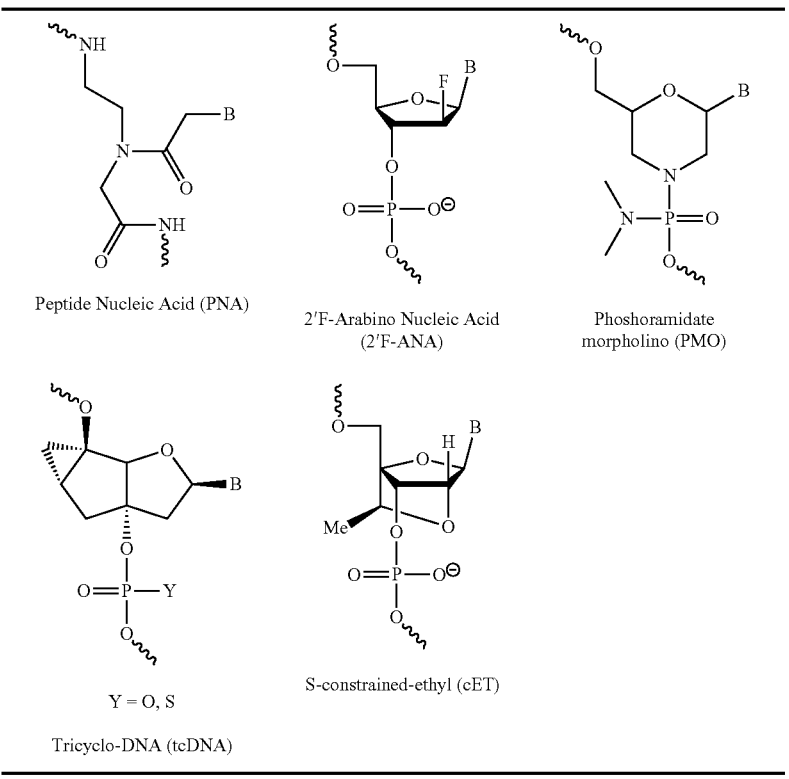

Peptide Nucleic Acid (PNA)

2'F-Arabino Nucleic Acid (2'F-ANA)

Phoshoramidate morpholino (PMO)

Tricyclo-DNA (tcDNA)
Y = O, S

S-constrained-ethyl (cET)

The BAC may target and alter the expression of an endogenous or exogenous gene. Endogenous gene targets include but are not limited to genes associated with neuromuscular disease, metabolic disease, cancer, age-related degenerative diseases, and exogenous gene targets include those of an acquired disease e.g. viral infections.

Whilst the BAC may be linked to the CPP directly the Applicant has found the use of a BFL desirable. Exemplary, non-limiting BFL chemistries are illustrated in Table 5.

TABLE 5

| Entry | Linker (L) | Linker acronym is present | Z | $Y_3$ |
|---|---|---|---|---|
| 1 | | SMCC | | or not present |
| 2 | | AMAS | | or not present |

TABLE 5-continued

| Entry | Linker (L) | Linker acronym is present | Z | $Y_3$ |
|---|---|---|---|---|
| 3 | (structure) | BMPS | L–S–CH(NH$_2$)–C(O)–Y | Z–NH–CH$_2$CH$_2$–(O–)$_n$–C(O)– or not present |
| 4 | (structure) | GMPS | L–S–CH(NH$_2$)–C(O)–Y | Z–NH–CH$_2$CH$_2$–(O–)$_n$–C(O)– or not present |
| 5 | (structure) | DMVS | L–S–CH(NH$_2$)–C(O)–Y | Z–NH–CH$_2$CH$_2$–(O–)$_n$–C(O)– or not present |
| 6 | (structure) | EMCS | L–S–CH(NH$_2$)–C(O)–Y | Z–NH–CH$_2$CH$_2$–(O–)$_n$–C(O)– or not present |
| 7 | (structure) | LC-SMCC | L–S–CH(NH$_2$)–C(O)–Y | Z–NH–CH$_2$CH$_2$–(O–)$_n$–C(O)– or not present |
| 8 | (structure) | SM(PEG)$_n$ | L–S–CH(NH$_2$)–C(O)–Y | Z–NH–CH$_2$CH$_2$–(O–)$_n$–C(O)– or not present |
| 9 | (structure) | DSG | Not present | Z–NH–CH$_2$CH$_2$–(O–)$_n$–C(O)– or not present |
| 10 | (structure) | DSCDS | Not present | Z–NH–CH$_2$CH$_2$–(O–)$_n$–C(O)– or not present |

TABLE 5-continued

| Entry | Linker (L) | Linker acronym is present | Z | Y3 |
|---|---|---|---|---|
| 11 |  | HNA | Not present | 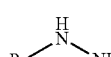<br>or not present |

By way of a footnote to Table 5, the following should be noted:

FIG. 5A highlights general structure of a DCCPM where the following are preferred, but not limited to the following defined atoms or groups.

In a preferred embodiment illustrated in FIG. 5C, where Y1=Nitrogen, Y2=Hydrogen, Y3=spacer such as (PEG)n n=5, but not limited to those identified in Table 5, Z=a sulfur containing moiety e.g. Cysteine and L=BFL such as SMCC Other embodiments may utilize variations over the structure shown in FIG. 5A. For example if another embodiment does not require a thiol for conjugation of the BFL to the CPA as illustrated in FIG. 5D, then Z=Y3 where Y3 is a spacer in Table 5. For a BFL that does not require a sulphur for conjugation of the BAC and CPA e.g. not limited to entries 9-11 in Table 5 Z=a covalent bond between L and Y3

Other embodiments may not require the use of a spacer, a BFL and as such a thiol group for the formation of a DCCPM depicted in FIG. 7 then the following apply. If no spacer is utilized then Y3 can represent a covalent bond between Y1 and the BAC in which case Z and L=Y1 where Y1 is a N terminus of the CPA.

These chemistries may be further expanded and Table 6 exemplifies modifications to amino acids via which functional groups can be introduced to provide desirable properties to the DCCPM. These will include, but are not limited to, an acetyl, a cholesterol, a fatty acid, a polyethylene glycol, a polysaccharide, an aminoglycan, a glycolipid, a polyphenol, a nuclear localising signal, a nuclear export signal, an antibody, and a targeting molecule.

TABLE 6

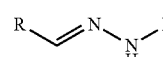

TABLE 6-continued

A preferred linker chemistry utilises an amine to sulphydryl cross linker containing N-hydroxysuccinimide esters and malemide reactive groups separated by a cyclohexane spacer namely succinimidyl 4-(N-maleimidomethyl) cyclohexane-1-carboxylate (SMCC) to form a covalent bond between the BFL and the CPP.

A schematic intermediate compound using SMCC as the BFL and the resultant DCCPM is depicted in FIG. 5b.

In a particularly preferred embodiment the linker may incorporate polyethylene glycol in single or multiple units $(PEG)_n$, where n=1 to 10 PEG molecules.

Hereafter, where the CPP comprises the sequence RKF-S5-RLF-S5 (SEQ ID NO: 57) and the BFL is a PEGylated SMCC, the resultant compound is termed CP8M.

Where the CPP comprises the sequence RKF-S5-RLF-S5 (SEQ ID NO: 57) and the BFL is a PEGylated hydrazynal nicotinic acid (HNA), the resultant compound is termed HP8M.

Where the CPP comprises the sequence RKF-S5-RLF-S5 (SEQ ID NO: 57) and the BFL is SMCC, the resultant compound is termed CBM.

Thus a CPA, such as Compound III (FIG. 5b) may be covalently linked to a BFL, if required, preferentially incorporating (PEG)$_n$ where n=1-10.

Covalent linkage to the CPP may be via, for example, but not limited to, a β-ala or any other suitable moiety.

In the preferred embodiment, the (PEG)$_n$ is linked using a sulphur containing molecule e.g. cysteine, to enable covalent coupling as a PEGylated (SMCC). This in turn is covalently linked to a functional group on the BAC, in the preferred embodiment a primary amine, (Compound I), thus generating a DCCPM (Compound V).

According to a second aspect of the invention there is provided a method for facilitating the uptake of a biologically active compound (BAC) into a cell by the conjugation of the biologically active compound, directly or via a bi-functional linker (BFL), to a cell penetrating agent (CPA) which is a stabilized peptide which has a conformation imposed upon it by stapling to form a stapled peptide (StaP) or stitching to form a stitched peptide (StiP), to form a drug carrying cell penetrating molecule (DCCPM) and presenting said DCCPM to said cell in a suitable vehicle.

Where HNA has been incorporated into the terminal end of the CPP, to form a DCCPM in which the BAC is an ON, the ON has been modified to incorporate 4 formyl benzioic acid to facilitate covalent conjugation.

According to a third aspect of the present invention there is provided a DCCPM of the first aspect of the invention for use in the treatment of a disease requiring alteration of the expression of an endogenous or exogenous gene.

The DCCPM may be used in the treatment of a, for example, neuromuscular disease, metabolic disease, cancer, age-related degenerative disease or to treat an acquired viral infection.

In one embodiment the DCCPM is used in the treatment of a muscular dystrophy e.g. Duchenne muscular dystrophy (DMD) although the skilled person will readily appreciate that the invention can be used to target a wide range of genes.

In the case of DMD the DCCPM may comprise an AON targeting exon 51 of the dystrophin gene.

In accordance with a fourth aspect of the present invention there is provided a method of improving the bioavailability of a drug or BAC comprising linking the drug or BAC to a CPP which is a stabilized peptide which has a conformation imposed upon it by stapling to form a stapled peptide (StaP) or stitching to form a stitched peptide (StiP).

In accordance with a fifth aspect of the present invention there is provided a method of introducing a drug or BAC to a site which is refractory to a drug or BAC in its native state comprising linking the drug or BAC to a CPP which is a stabilized peptide which has a conformation imposed upon it by stapling to form a stapled peptide (StaP) or stitching to form a stitched peptide (StiP) and administering it to a subject.

The DCCPMs of the invention can be used to administer the drug or BAC to a target tissue, such as, for example the heart, brain or muscle.

In accordance with a sixth aspect of the present invention there is provided a method of treating a subject to alter the expression of an endogenous or exogenous gene comprising administering a DCCPM of the invention to a subject.

In accordance with a seventh aspect of the present invention there is provided a composition comprising a DCCPM of the invention and one or more pharmaceutically acceptable excipients enabling the composition to be administered orally, parenterally, intravenously or topically.

BRIEF DESCRIPTION OF THE DRAWINGS

Embodiments of the invention are further described hereinafter with reference to the accompanying Drawings, in which:

FIG. 1a is an example of a non-cyclised and an i,i+4 ring closing metathesis (RCM) using Grubb's Gen 1 catalyst to form an StaP CPA;

FIG. 1b is an example of a reduced RCM StaP using conventional reduction chemistry;

FIG. 1c is a schematic showing a selection of different StaP or StiP RCM configurations and their corresponding starting positions;

Figure 1A:
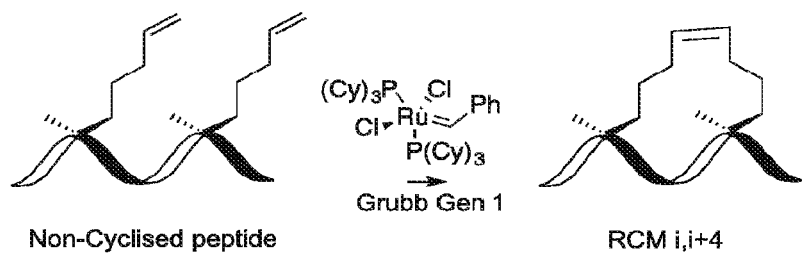
FIG. 1a-1c show a general schematic of a CPP which it has been stabilized by means of the incorporation of olefin-bearing α, α-di-substituted amino acids that permit a further chemical modification such that a cross link can be formed. Cross linking of two such non-natural amino acids is termed stapling; cross linking involving more than two non-natural amino acids is termed stitching. This schematic can be referenced against Tables 1 and 2 of this application.
Figure 1B:
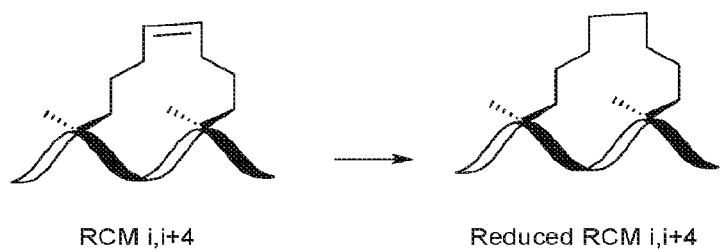
Figure 1C:
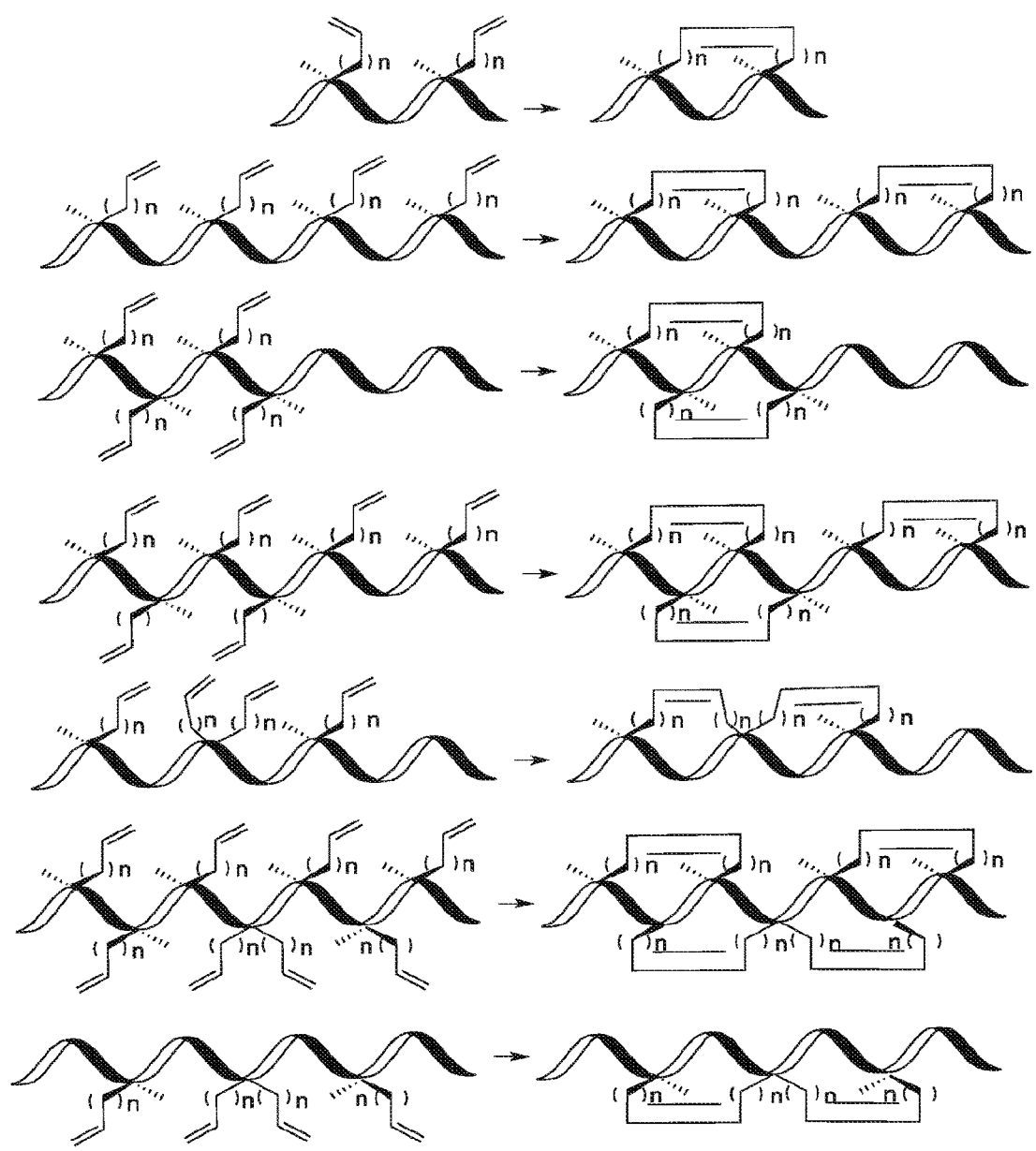
Figure 2:
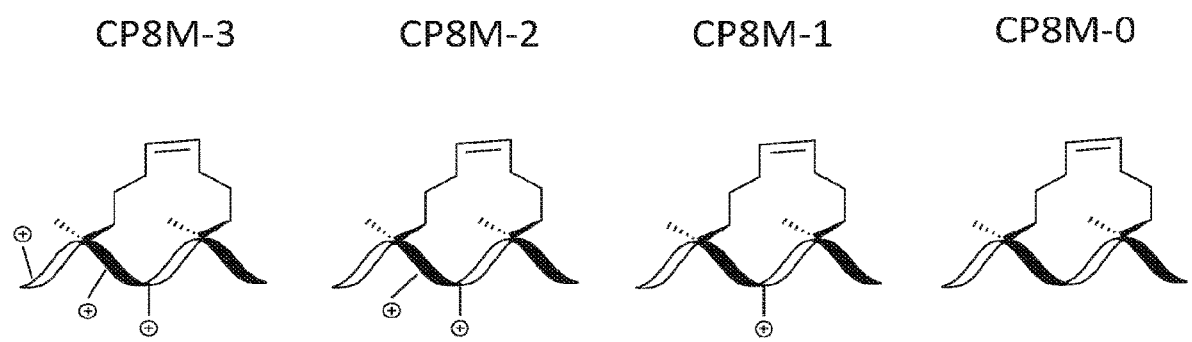
FIG. 2 exemplifies the structures of charge variants: 3+ (CP8M-3), 2+ (CP8M-2), 1+(CP8M-1) and 0+ (CP8M-0) illustrating relative positions of charge on the StaP, however the positions and charge can be varied in any permutation or combination.
Figure 3:
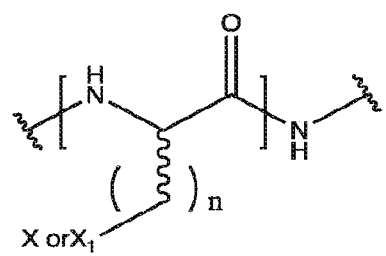
FIG. 3 exemplifies the structure of an amino acid which can be incorporated into StaP or StiPs with varying functional groups as defined in Table 6. The functional groups can then be used for bio-conjugation.
Figure 4A:
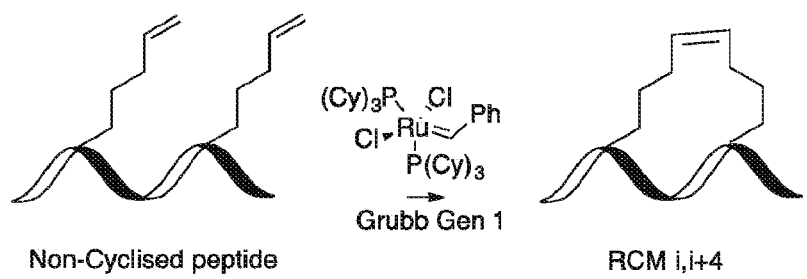
FIG. 4a is a representation of a RCM reaction to form a StaP.
Figure 4B:
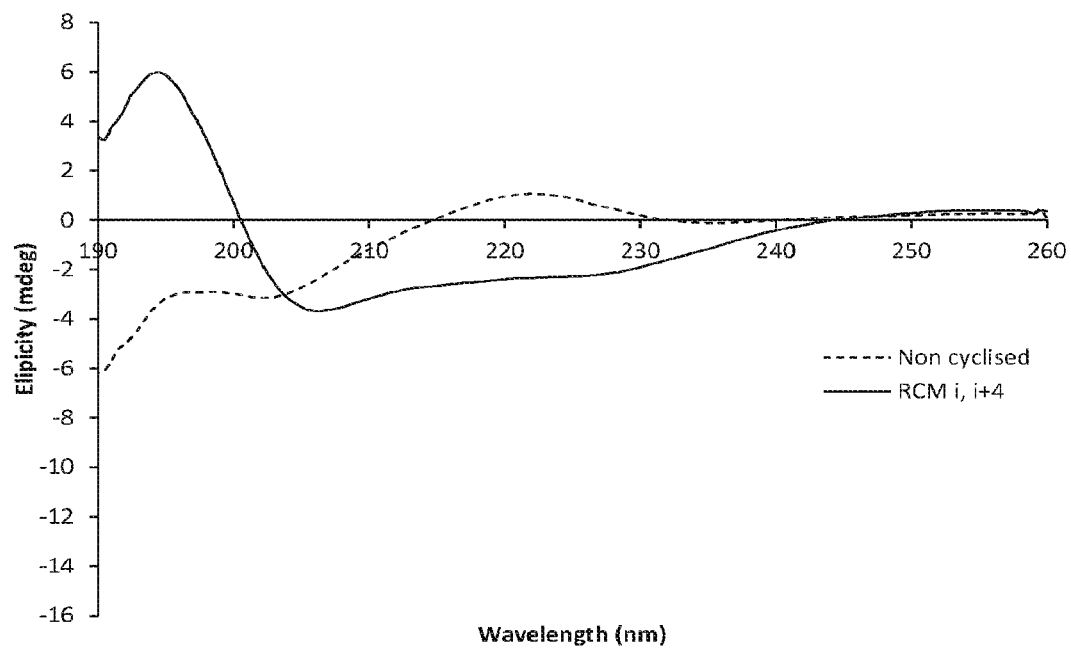
FIG. 4b shows the resulting CD spectrum of the StaP and non-cyclised stating peptide.
Figure 4C:
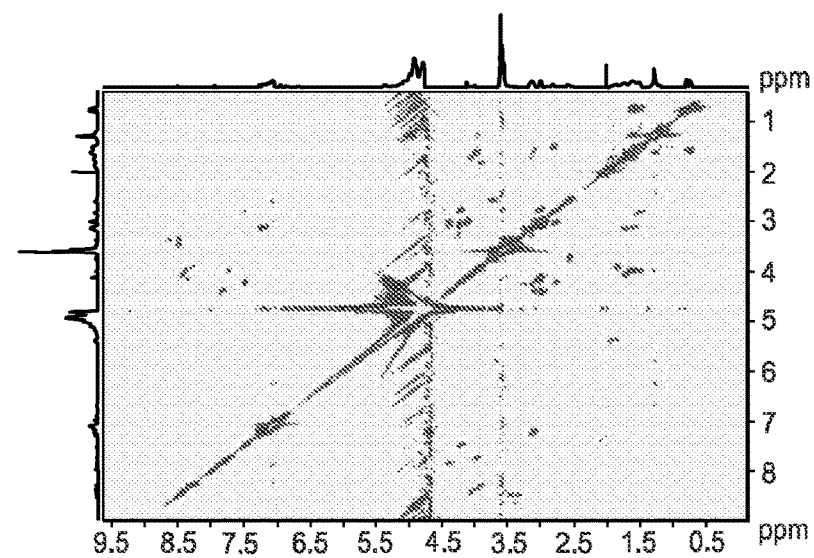
FIG. 4c is a COSY NMR spectra of CP8M.
Figure 4D:
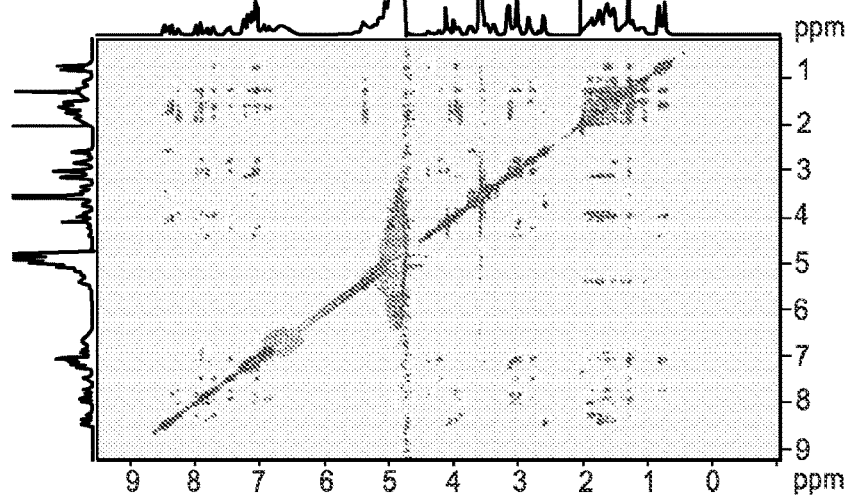
FIG. 4d is a NOESY NMR Spectra of CP8M.
Figure 4E:
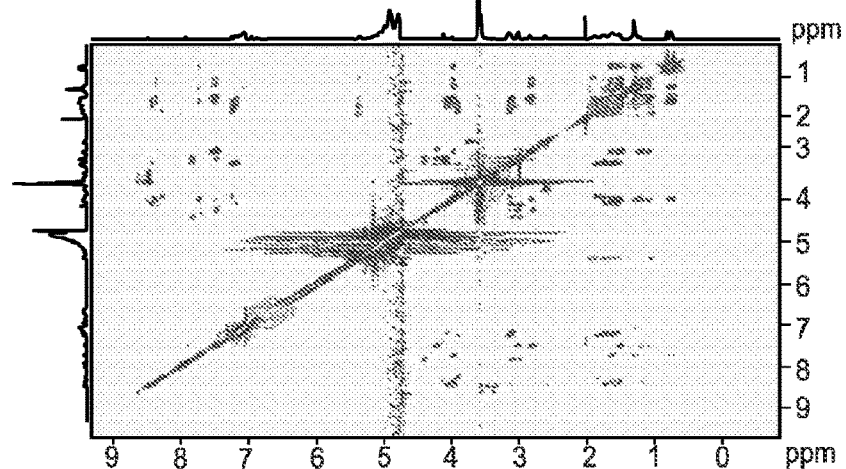
FIG. 4e is a TOCSY NMR spectra of CP8M.
Figure 5A:
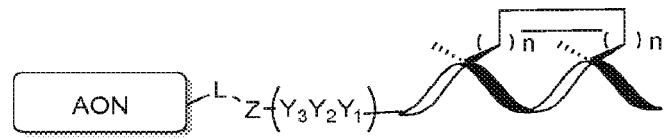
Figure 5B:
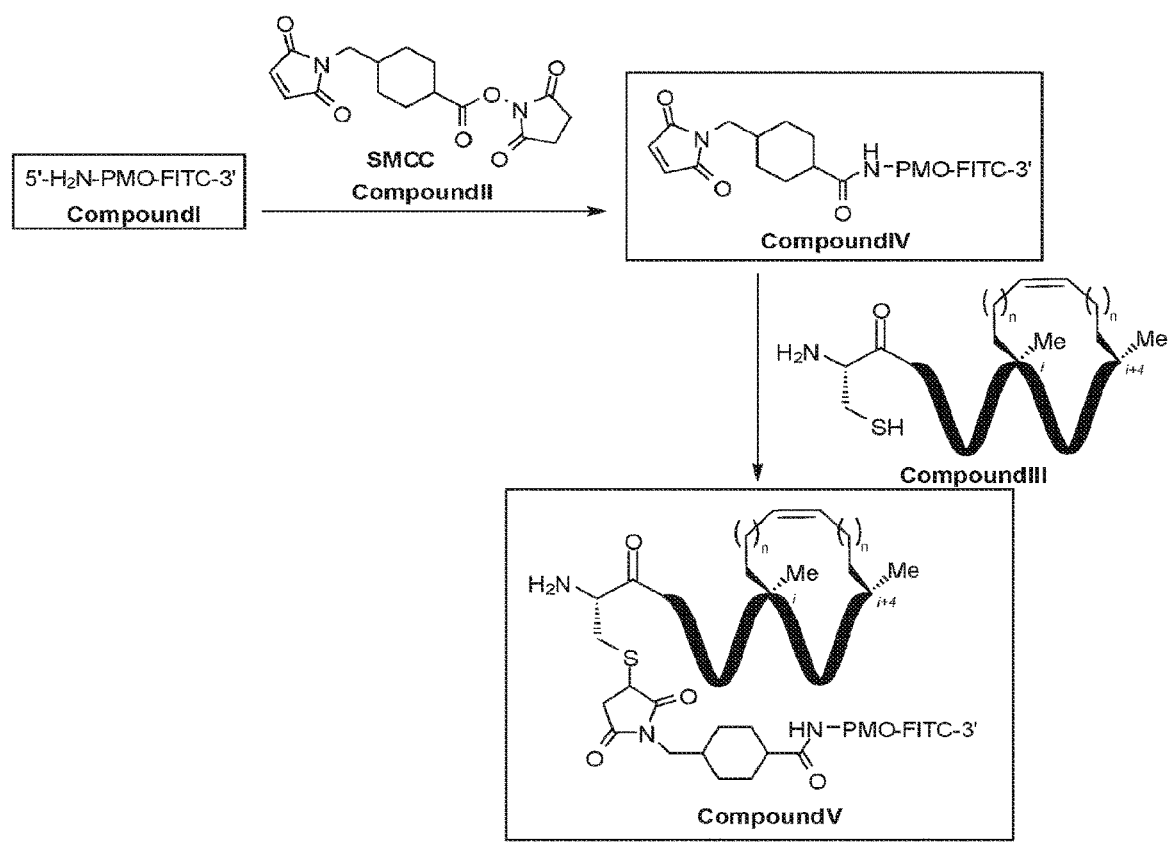
Figure 5C:
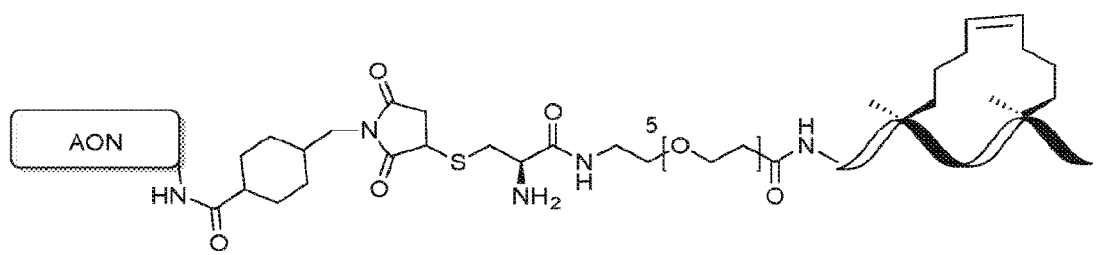
Figure 5D:
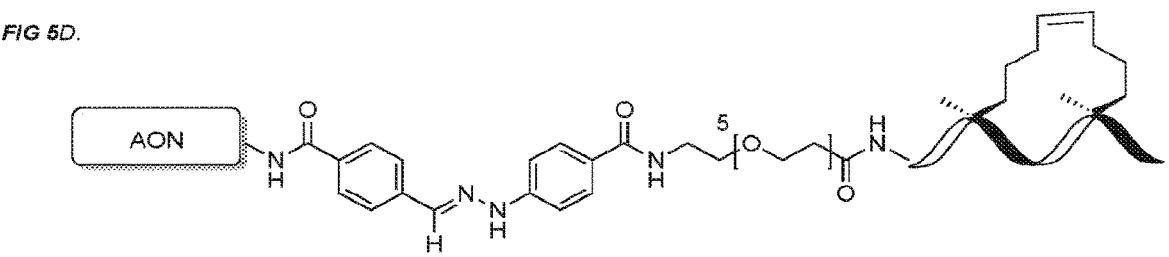
Figure 6:
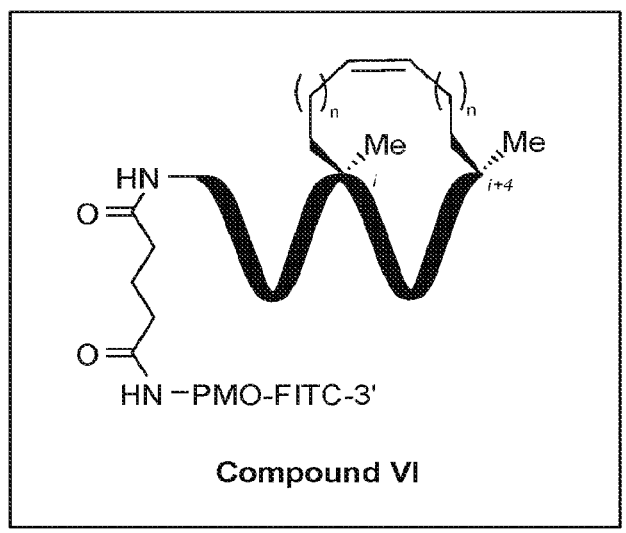
Figure 7:
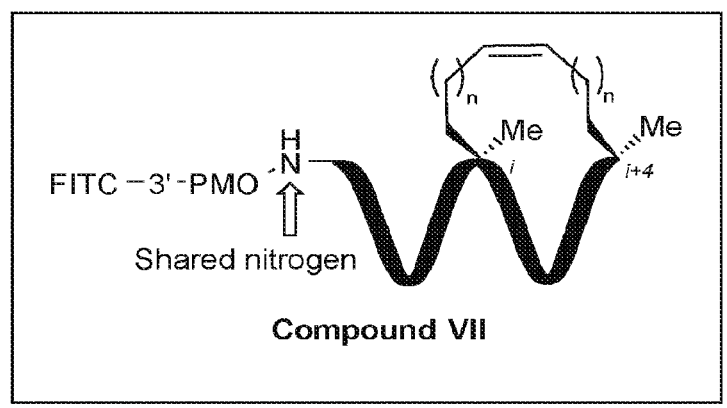
Figure 8A:
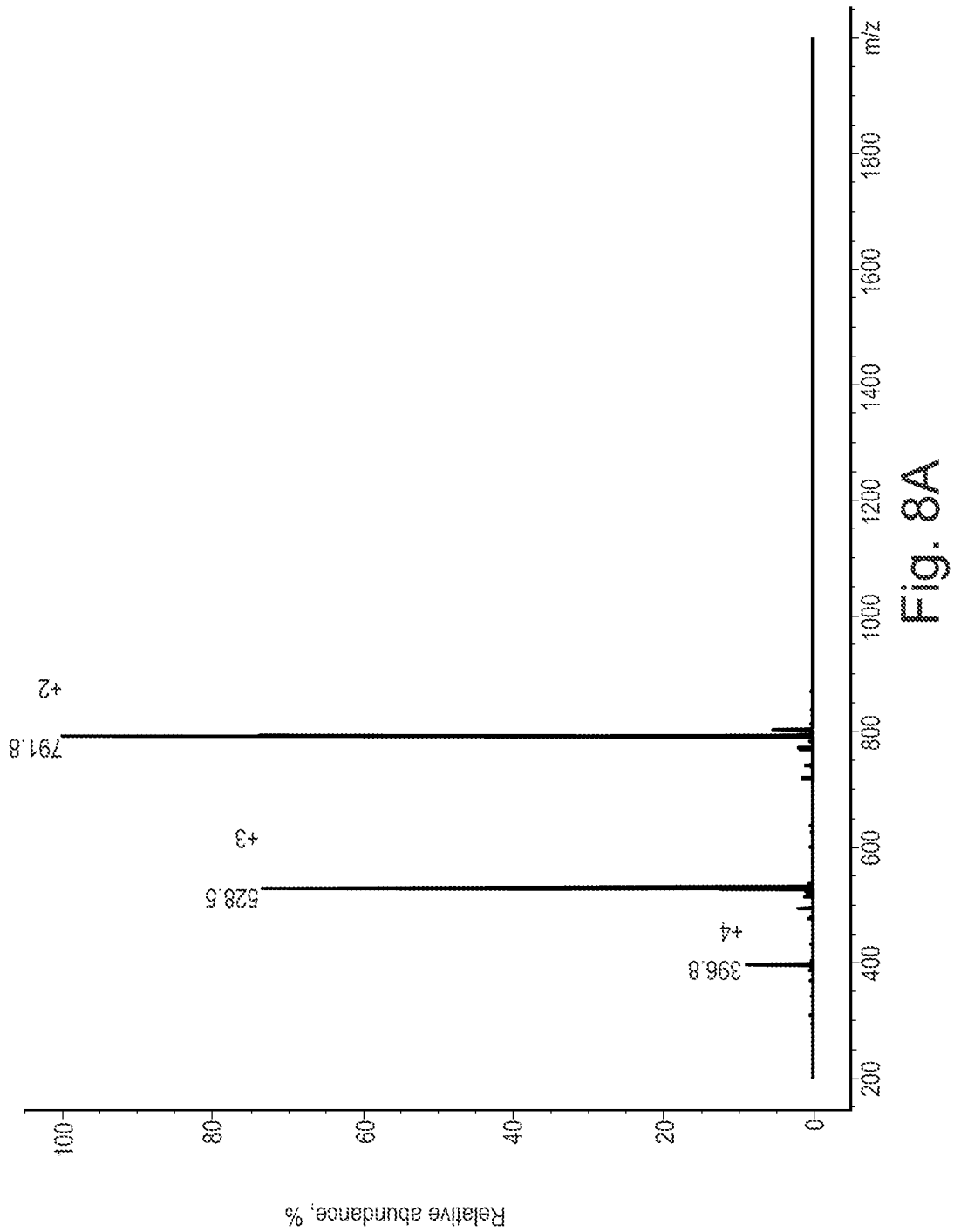
Figure 8B:
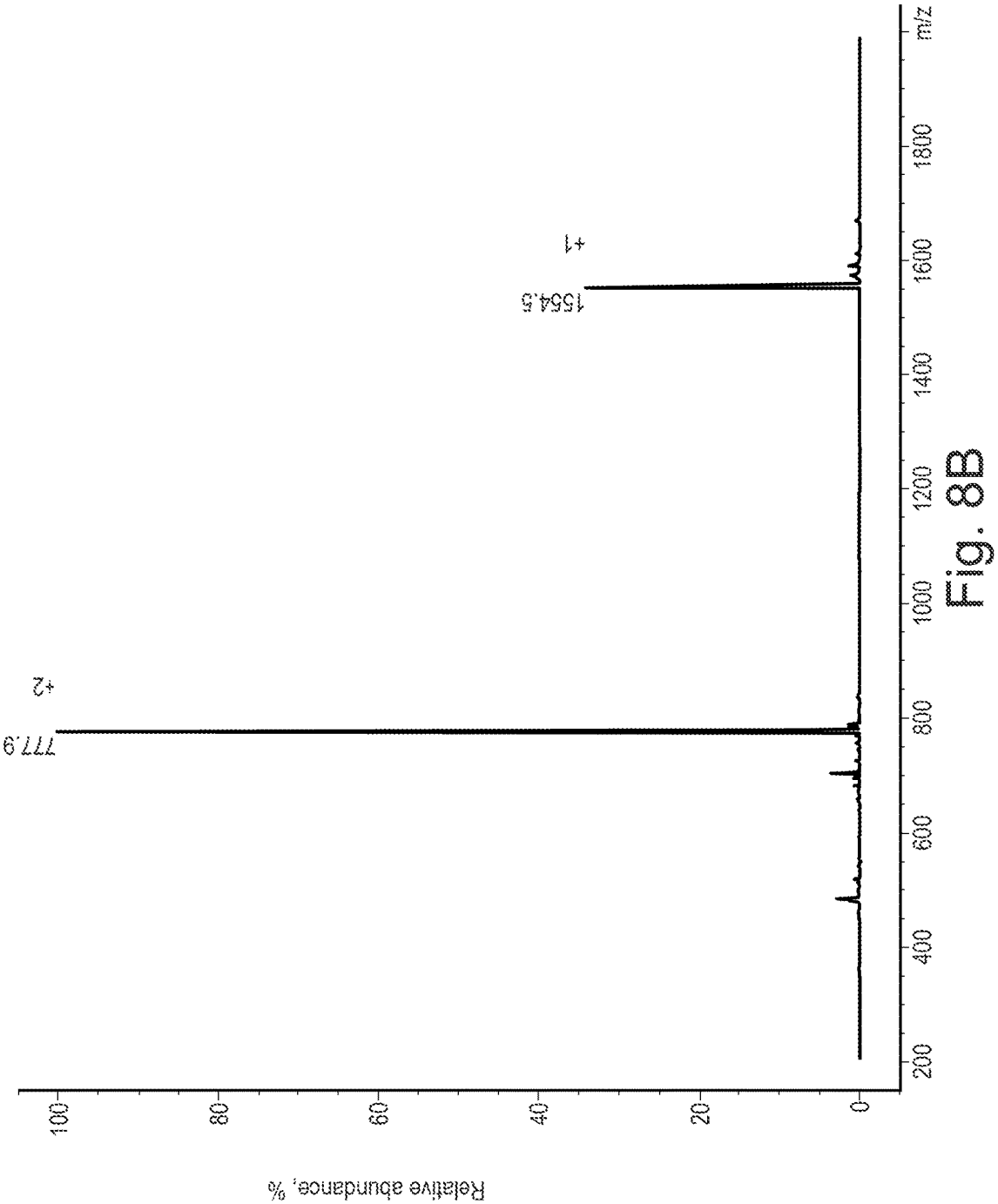
Figure 8C:
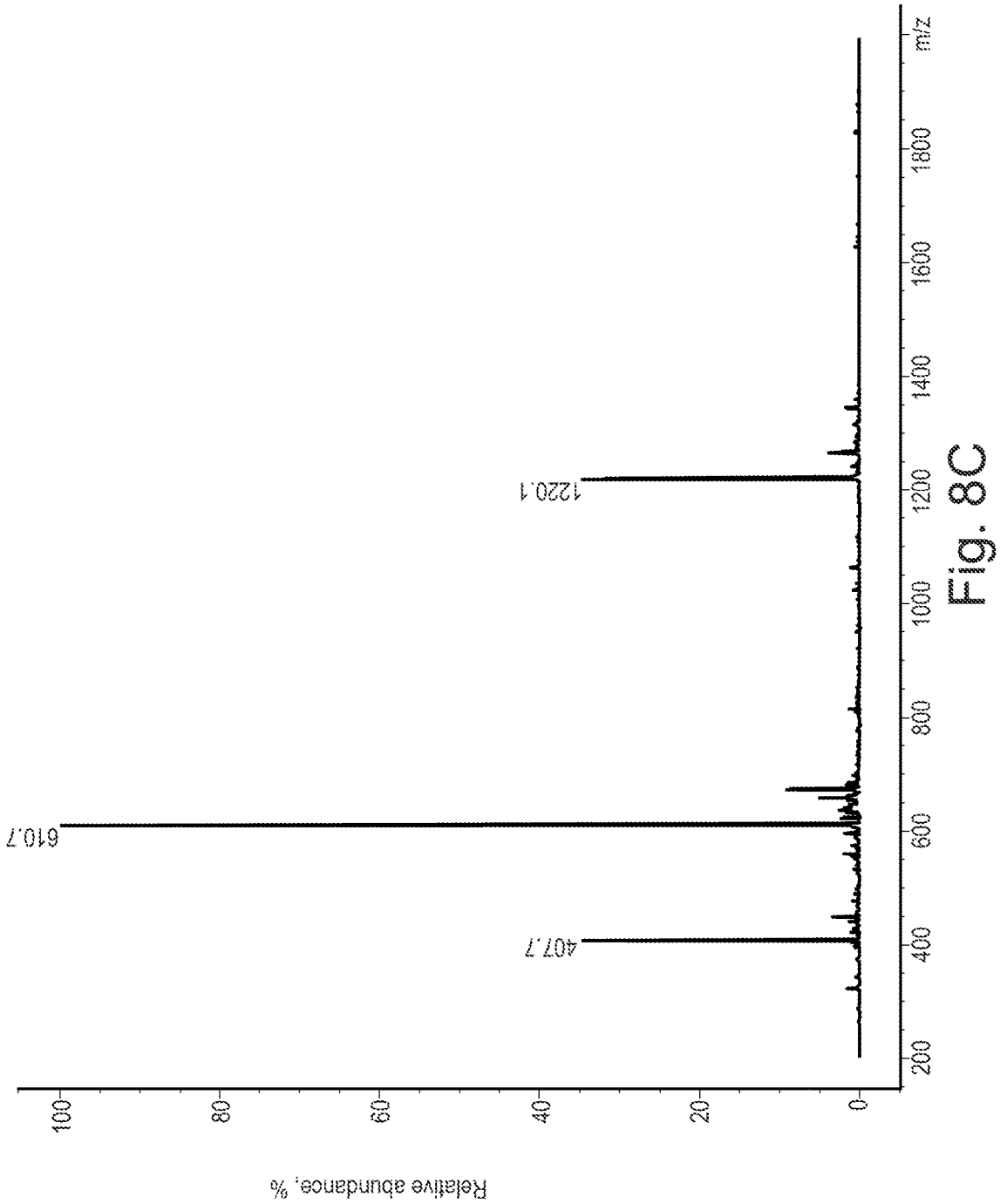
Figure 8D:
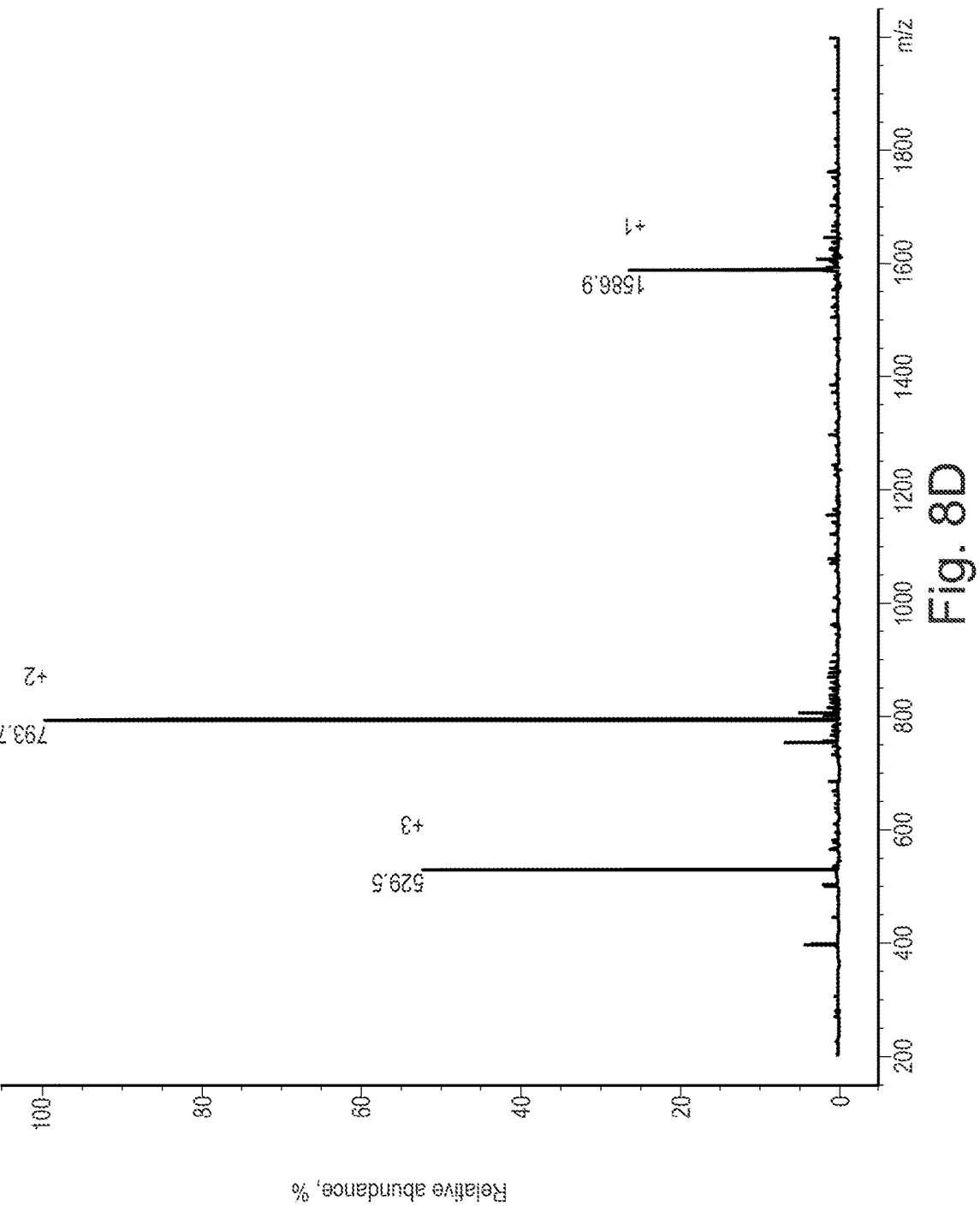
Figure 8E:
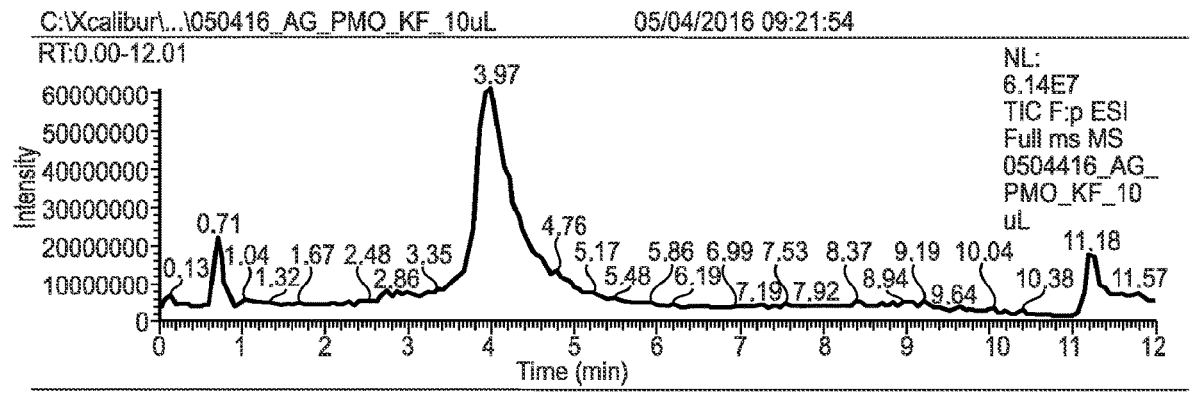
Figure 8E:
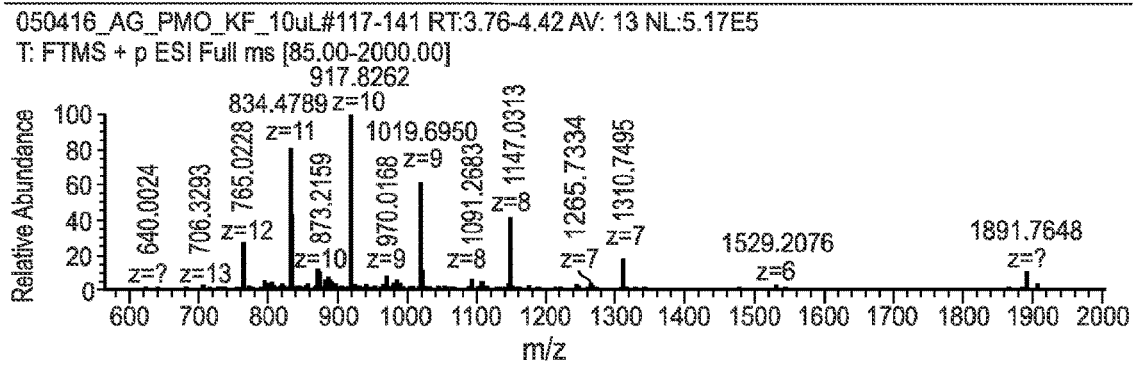
Figure 8E:
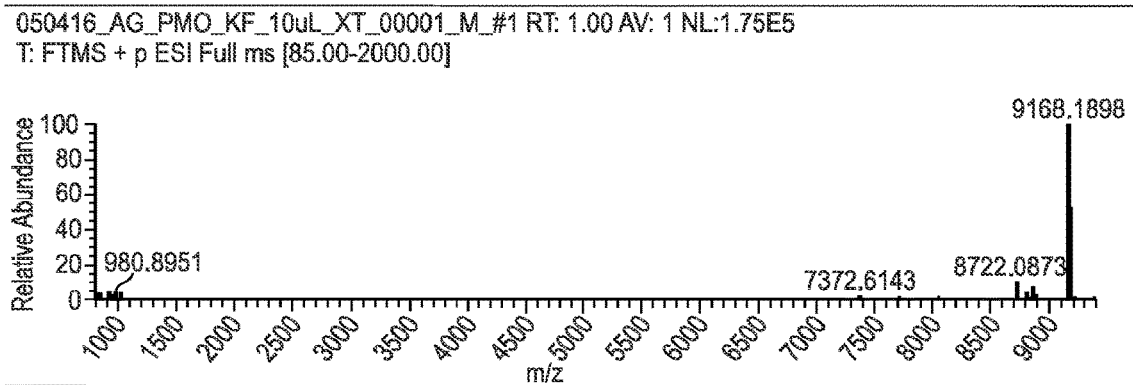
Figure 8E:
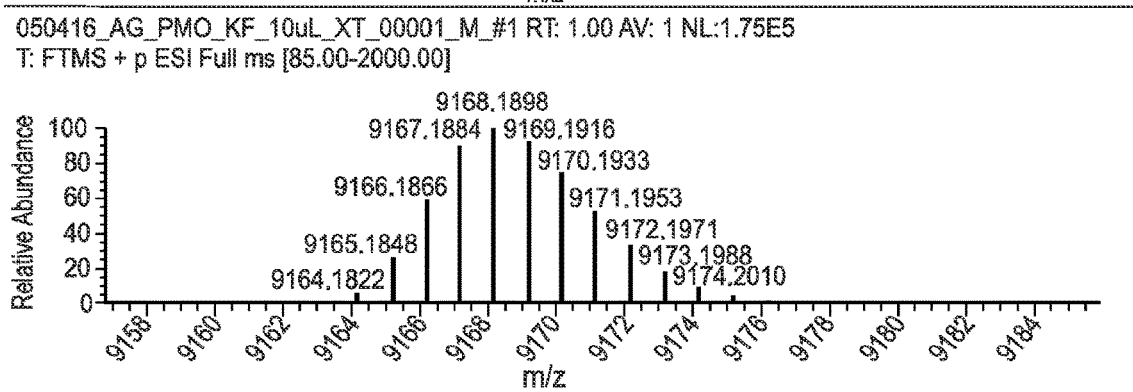
Figure 8F:
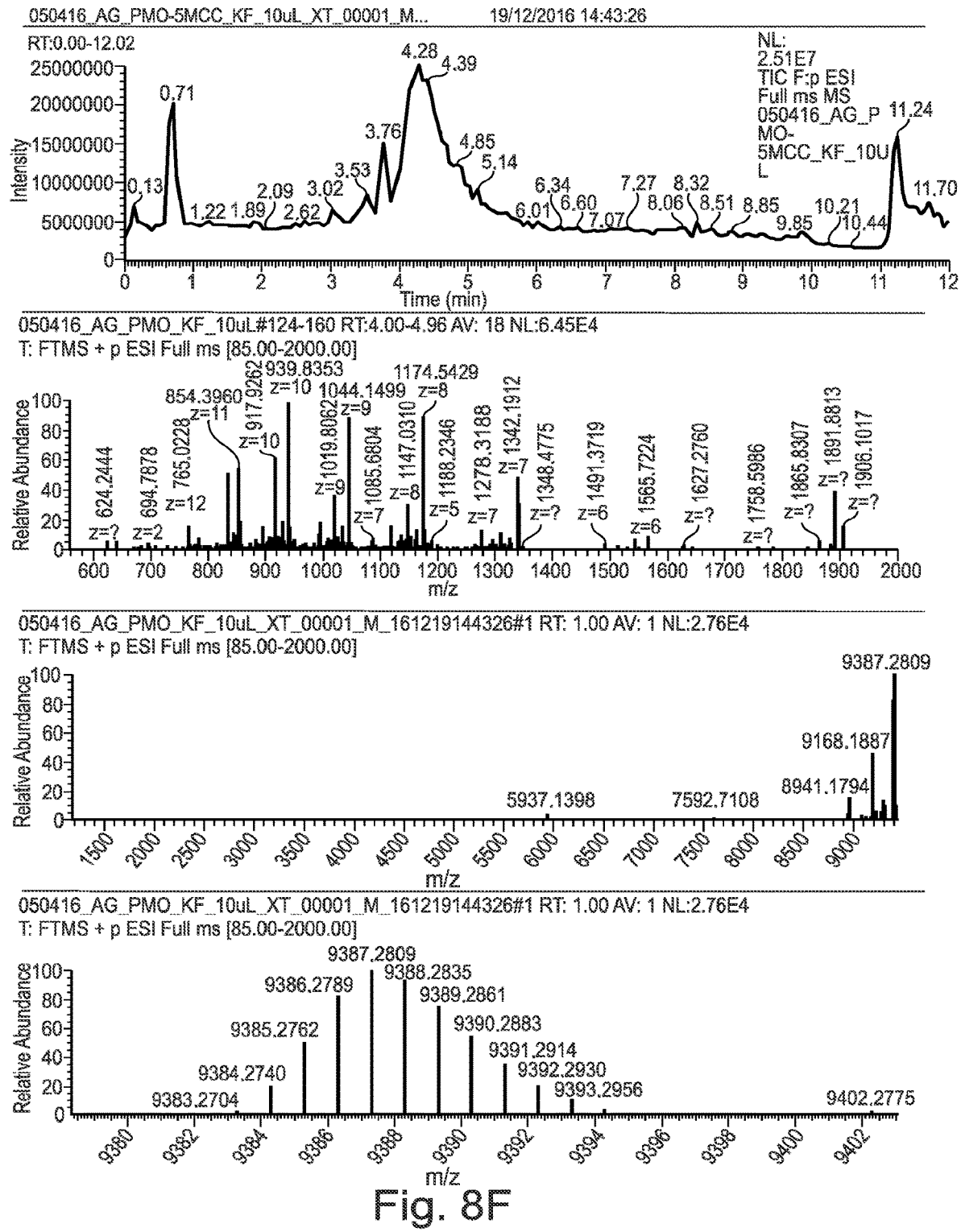
Figure 8G:
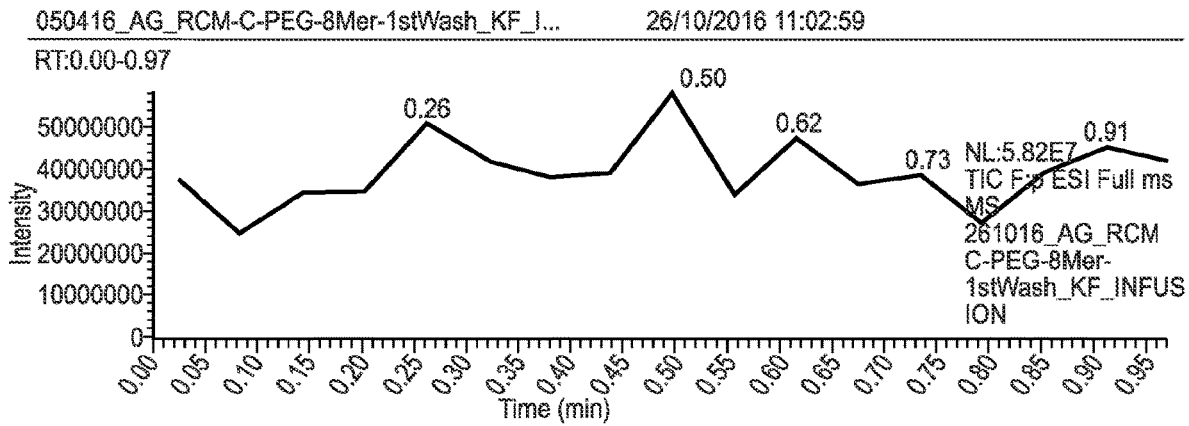
Figure 8G:
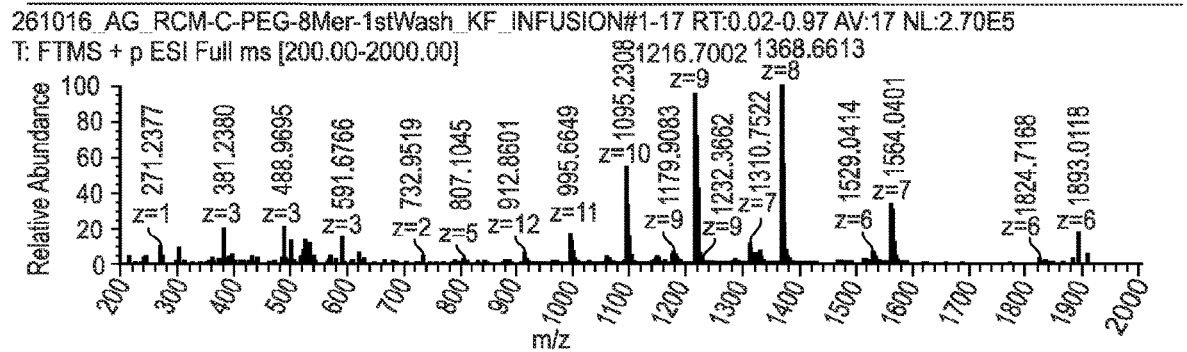
Figure 8G:
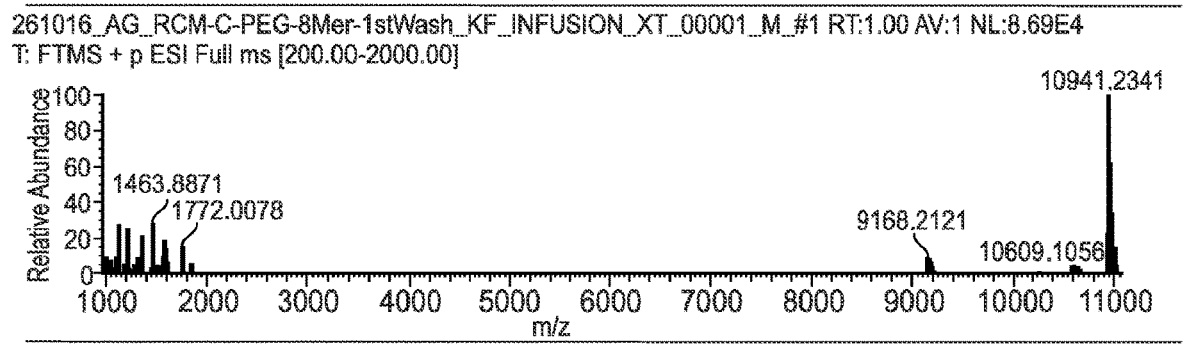
Figure 8G:
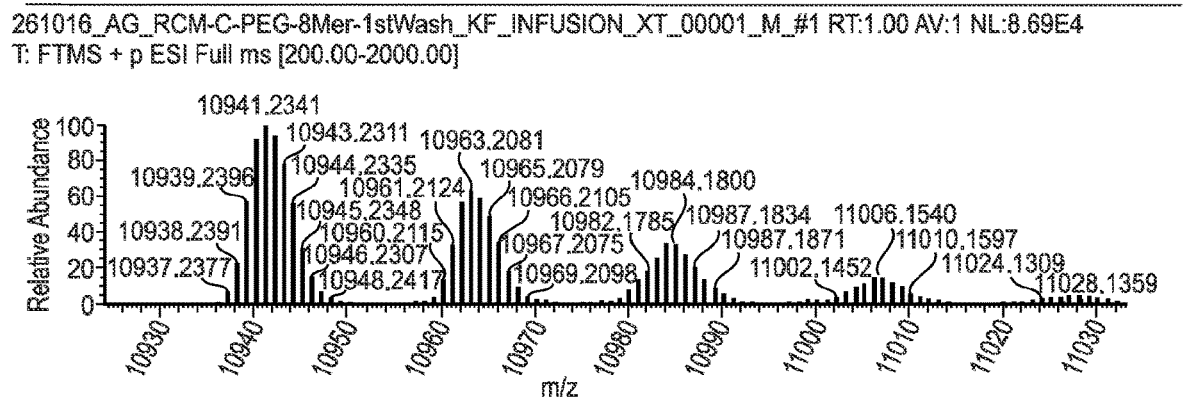
Figure 8H:
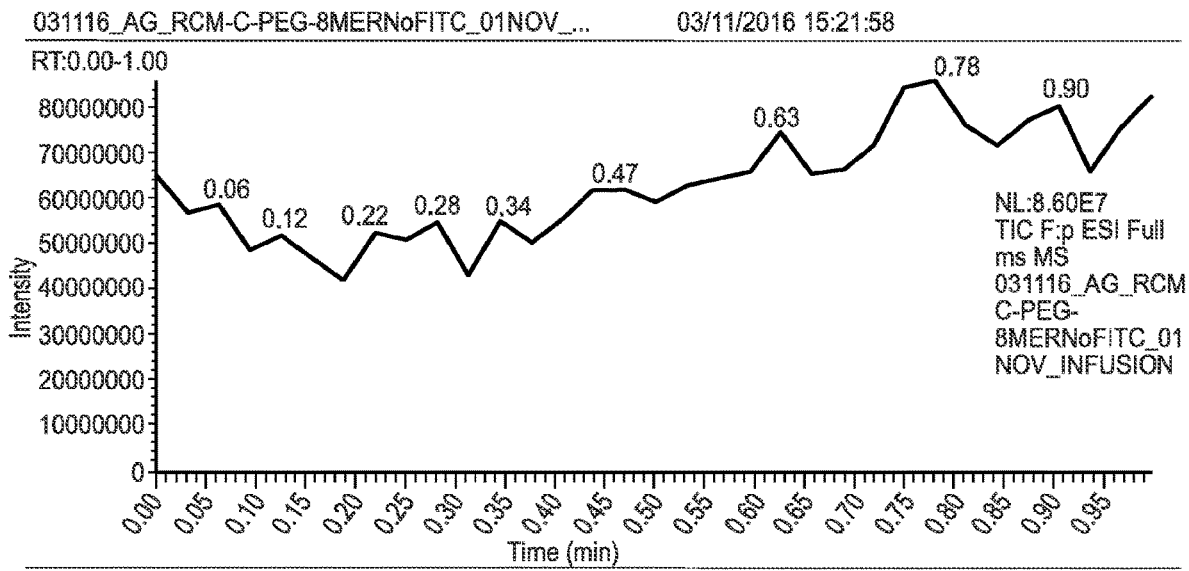
Figure 8H:
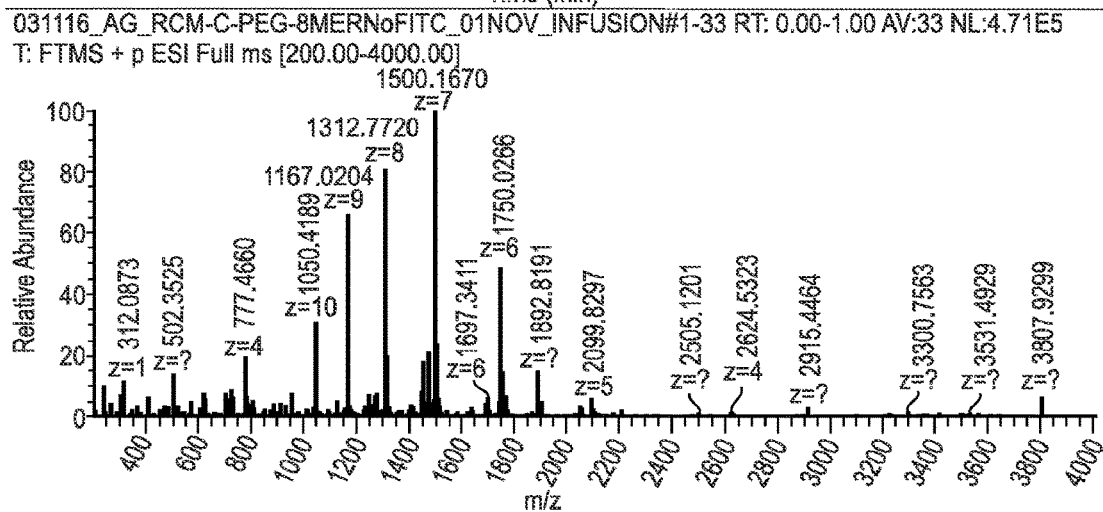
Figure 8H:
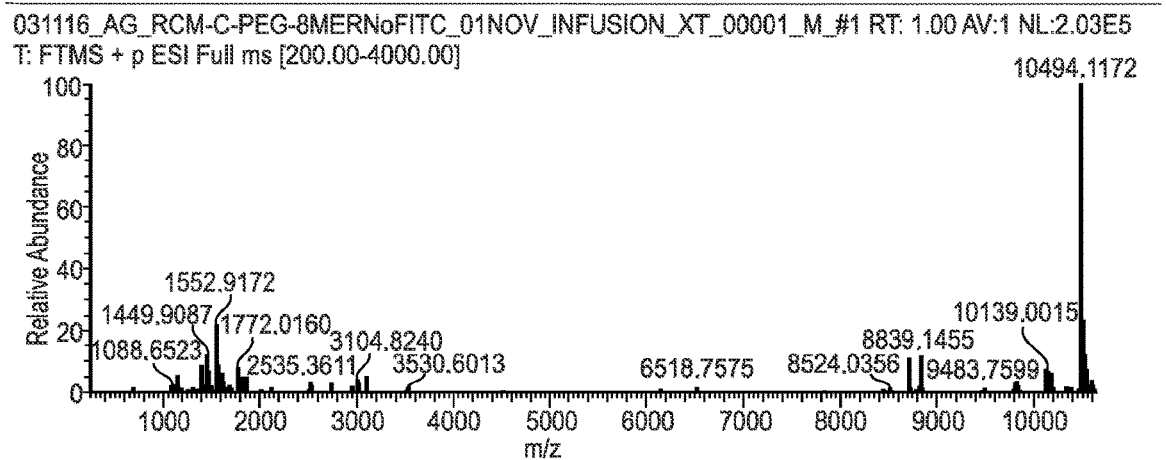
Figure 8I:
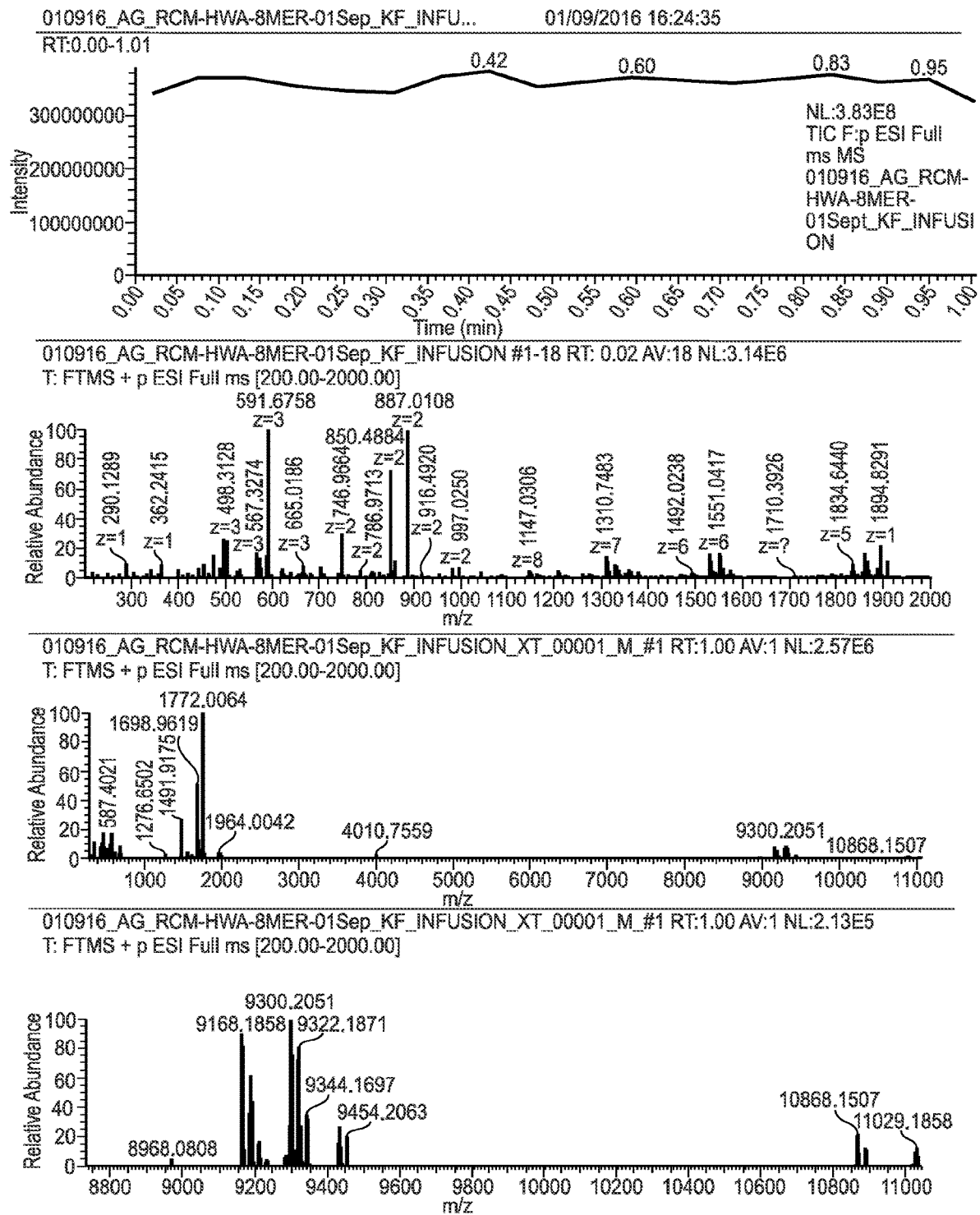
Figure 8J:
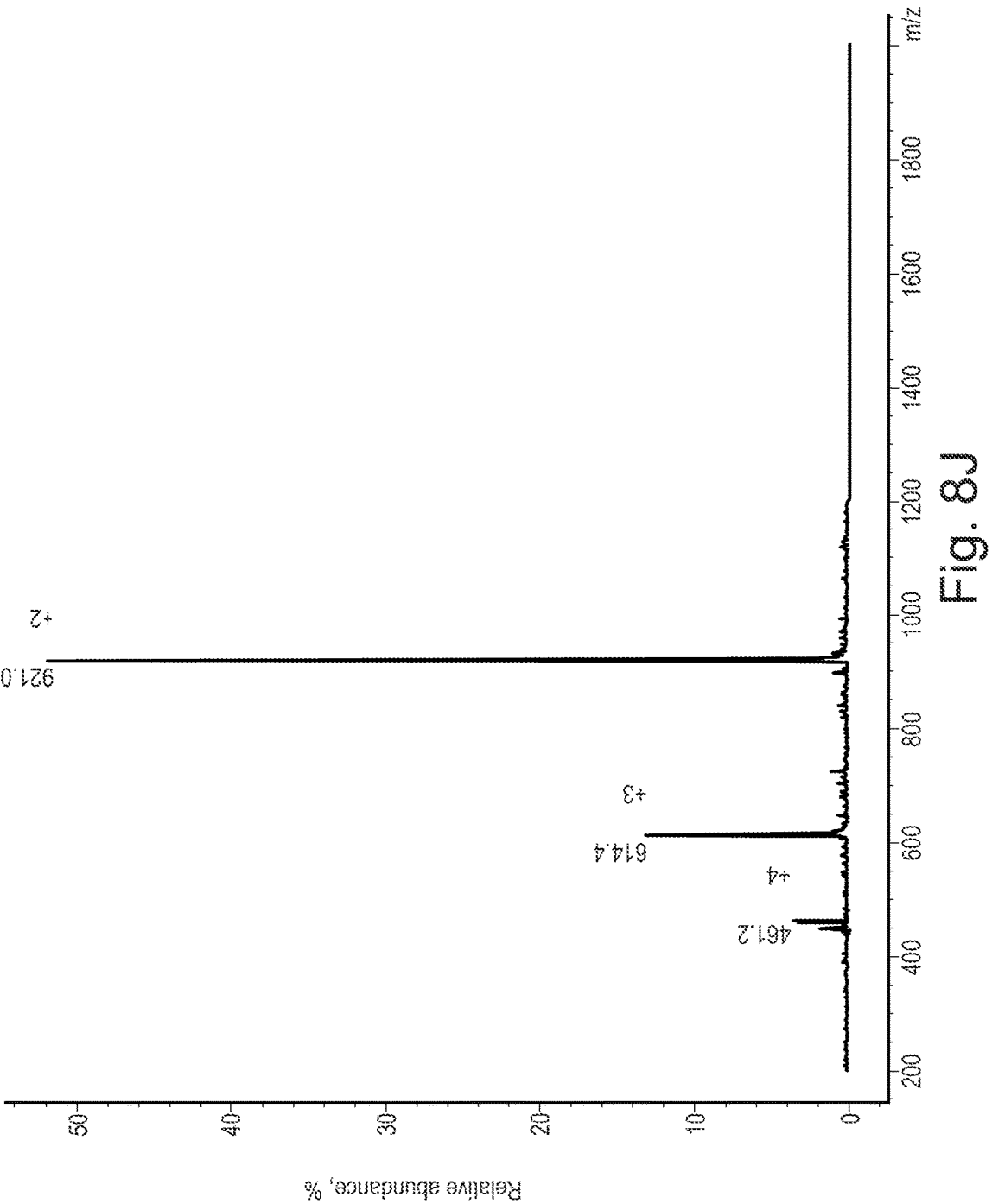
Figure 8K:
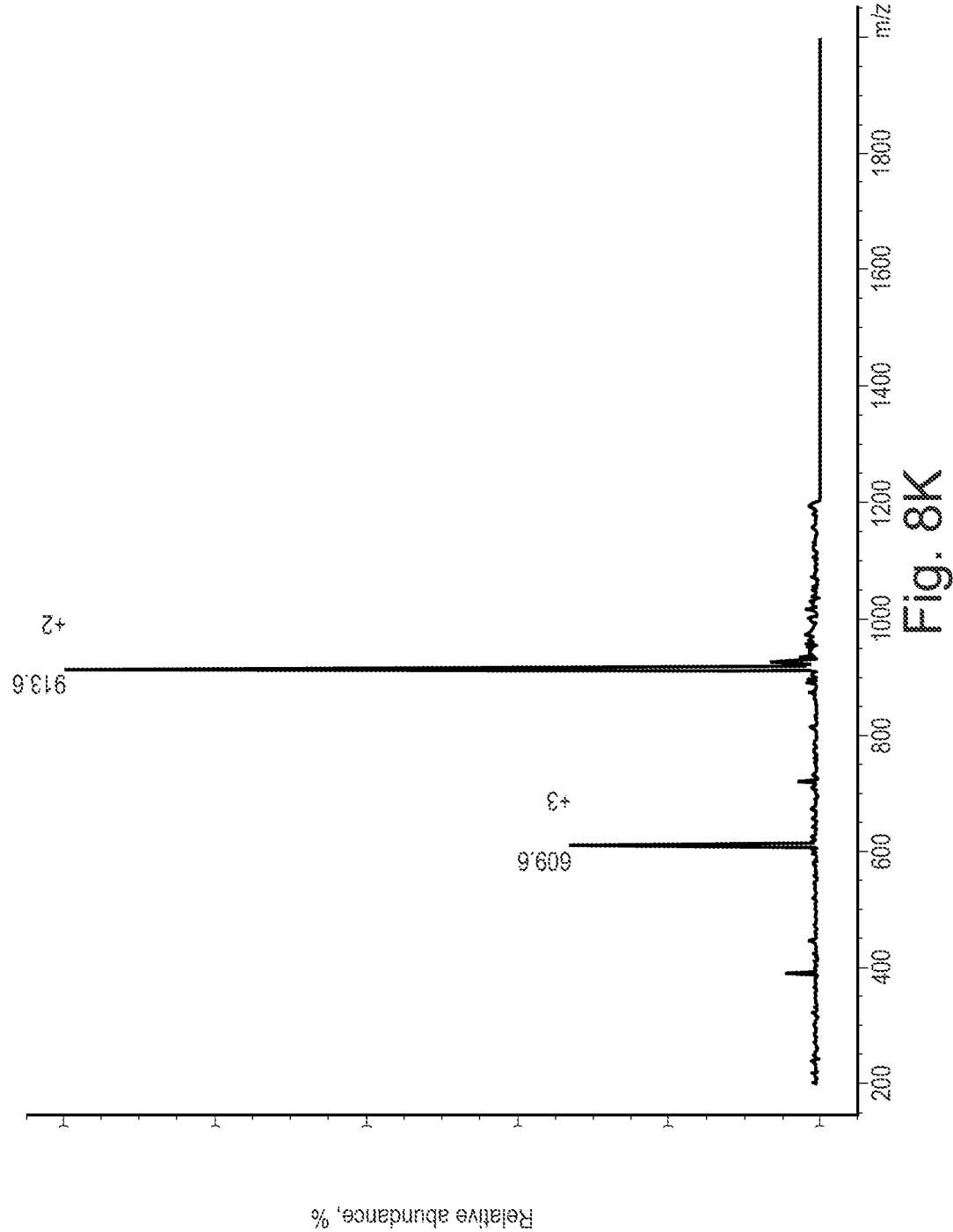
Figure 8L:
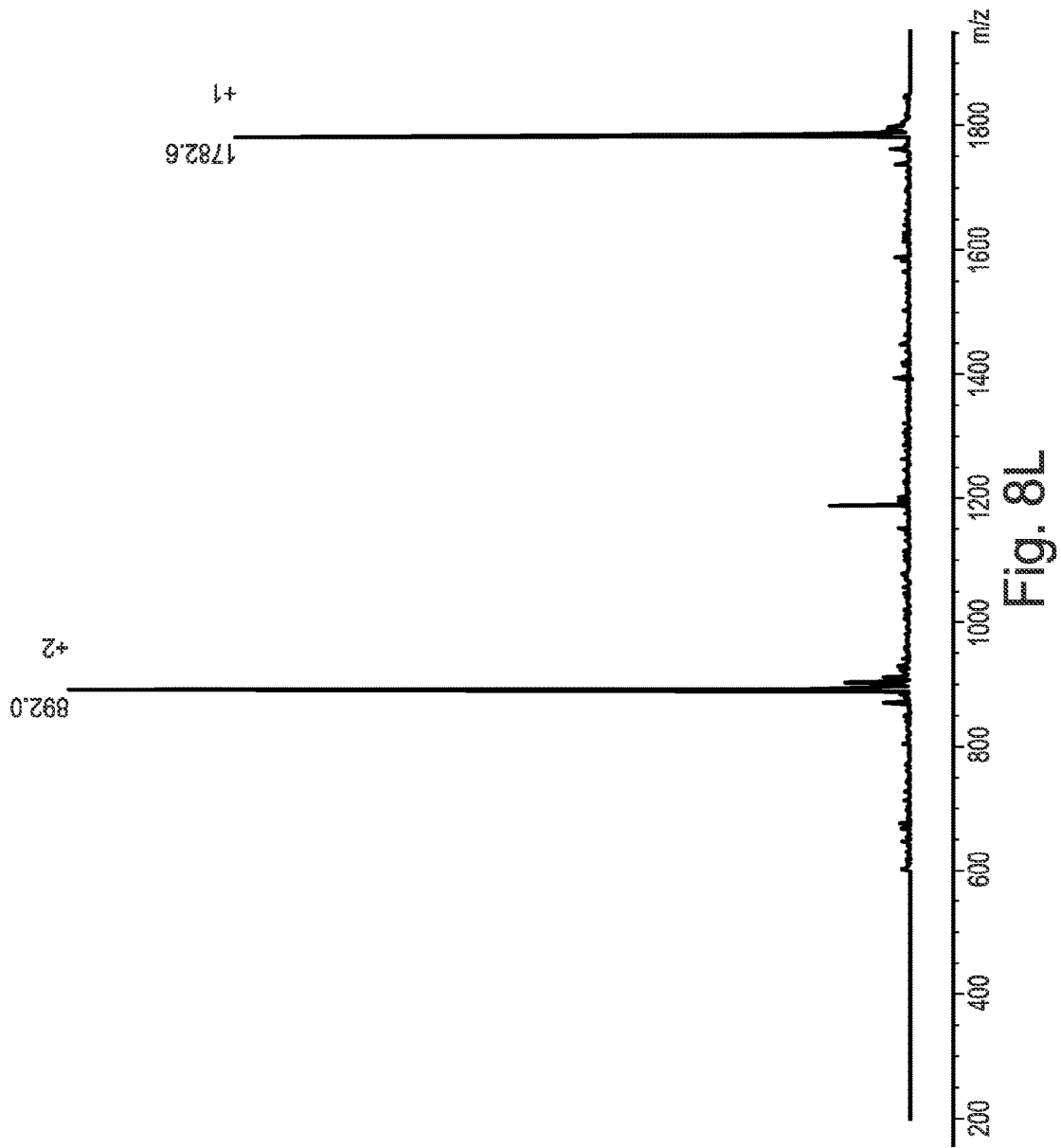
Figure 8M:
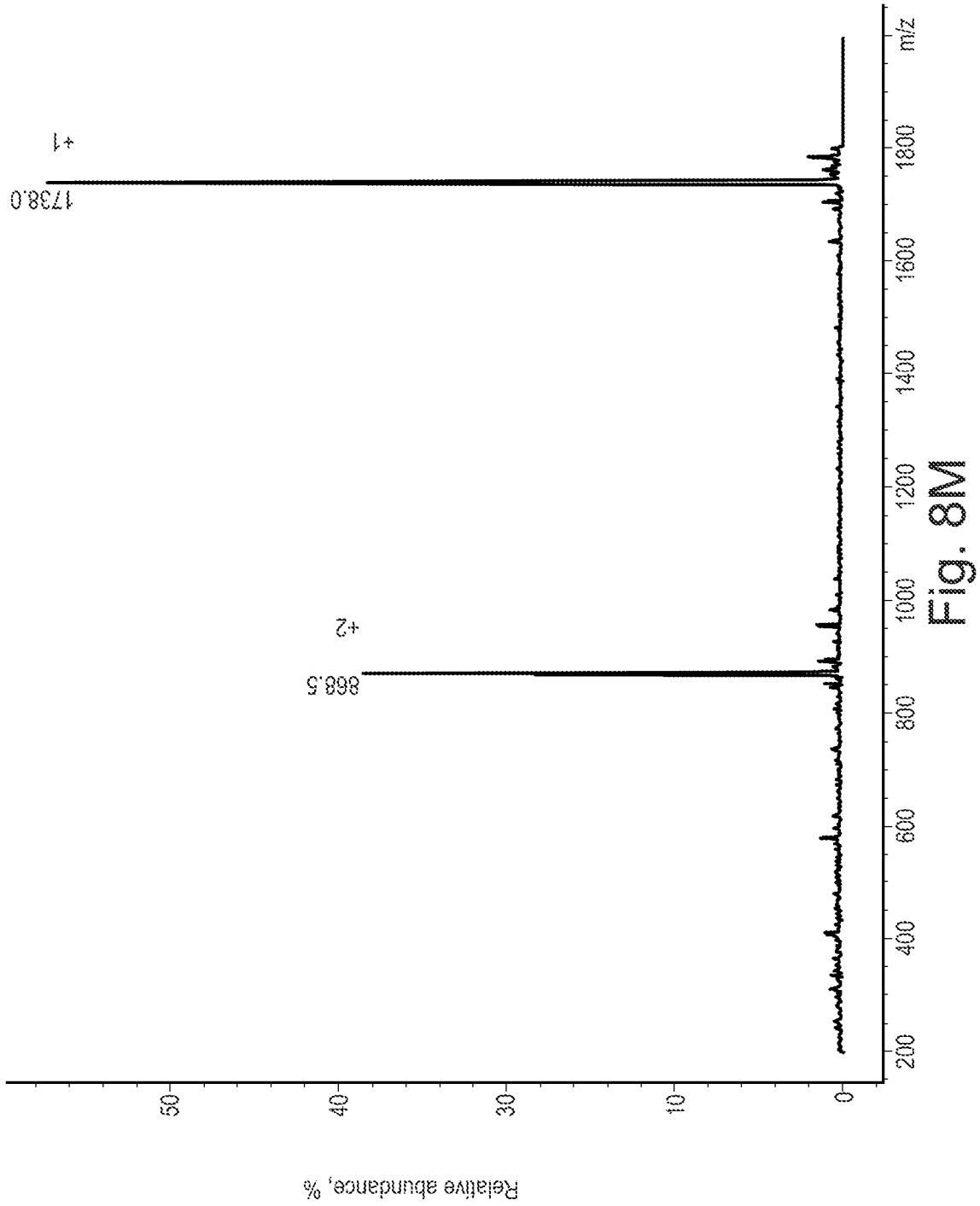
Figure 8N:
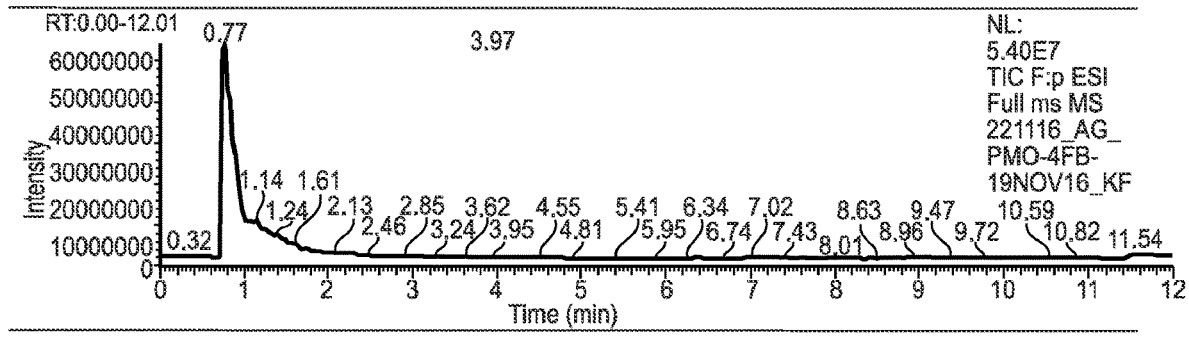
Figure 8N:
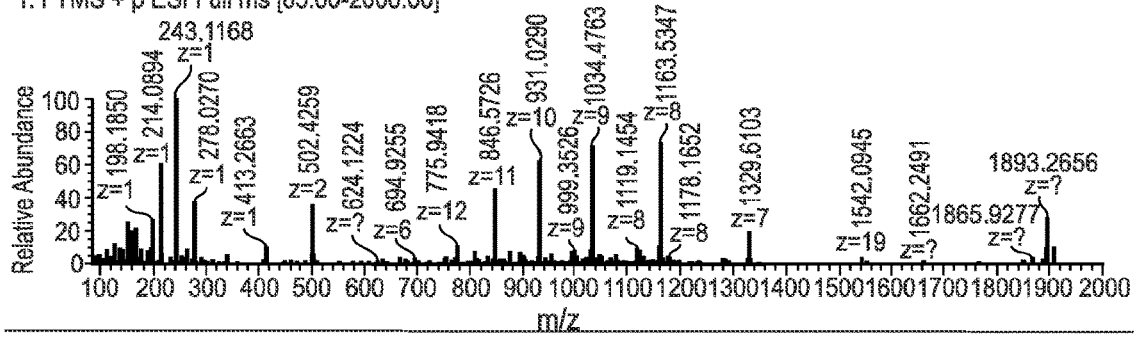
Figure 8N:
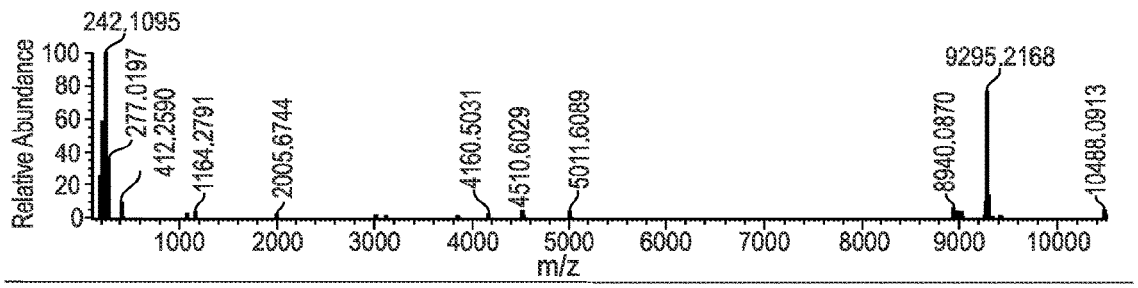
Figure 8N:
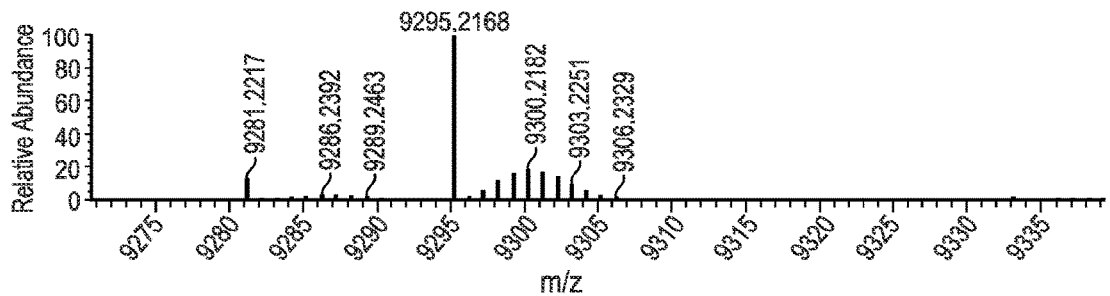
Figure 8O:
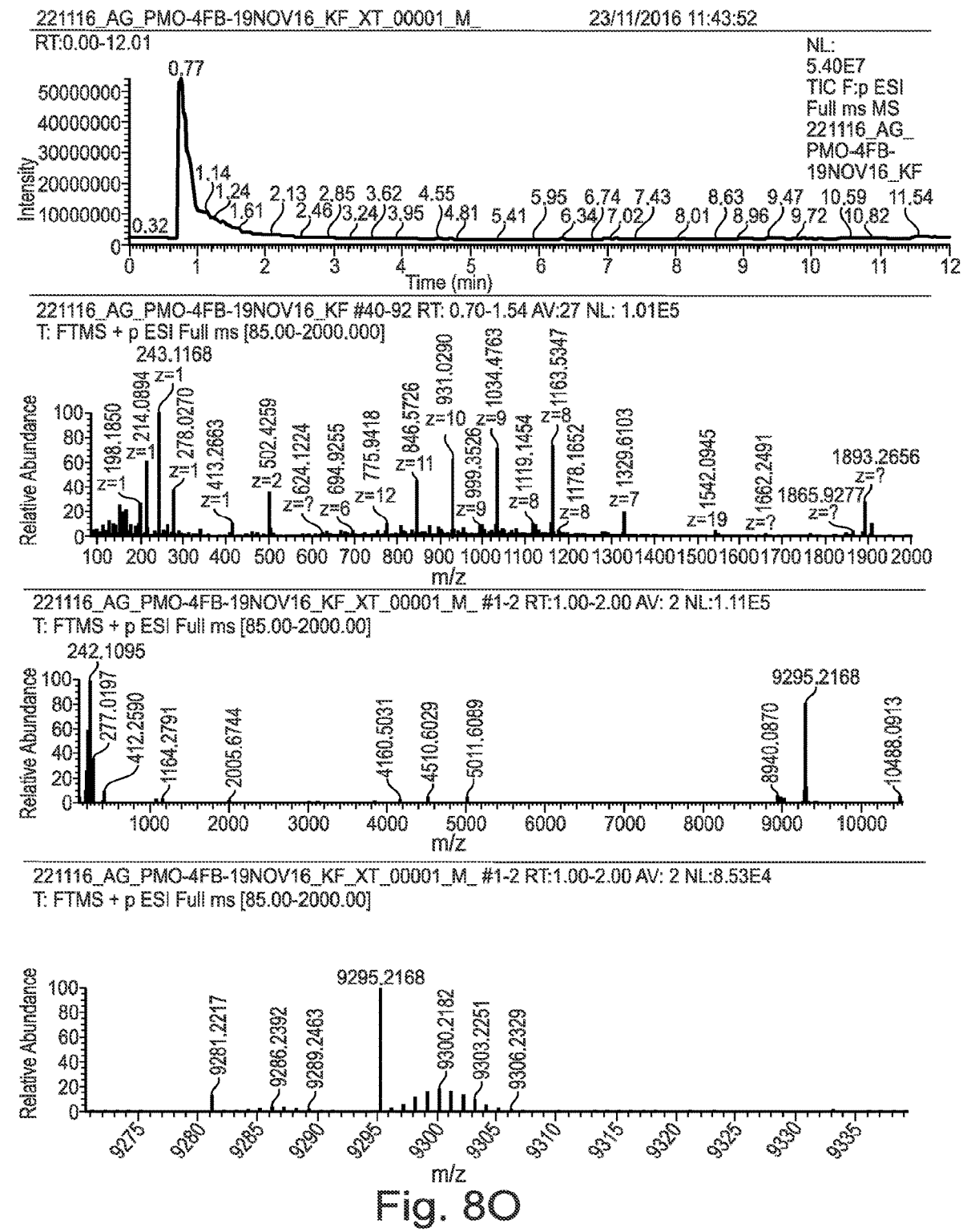

The Spectra were collected at room temperature in $H_2O$ spiked with 10% $D_2O$ and 10 mM sodium acetate;

FIG. 5a is a schematic diagram of StaP DCCPM depicting variants of linkers and spacers as defined in Table 5;

FIG. 5b is a schematic diagram of DCCPM depicting the synthetic steps for the conjugation of a StaP to a PMO. The PMO is modified to yield a 5' amine group (compound I); the heterobifunctional protein crosslinker Succinimidyl-4-[N-maleimidomethyl] cyclohexane-1-carboxylate (SMCC; compound II) is attached to 5' amine group to yield compound IV; an i,i+4 stapled peptide (compound III) is conjugated to generate the final DCCPM (compound V);

FIG. 5c is a DCCPM of CP8M conjugated to an ON using a SMCC linker (e.g. PMO-CP8M);

FIG. 5d is a DCCPM of HP8M using a HNA linker (PMO-HP8M);

The FITC group here and elsewhere may be any other fluorescent label and is present merely to enable visualization;

FIG. 6 shows a general schematic of a FITC labeled DCCPM in which the n-termini of the FITC labelled PMO (compound I) and the CPA (compound III) are linked via a bi-functional linker disuccinimidyl glutarate (DSG) forming compound VI;

FIG. 7 shows a general schematic diagram of a DCCPM in which a FITC labelled PMO is directly conjugated to a CPA through a shared nitrogen forming compound VII;

FIGS. 8a-8o show the liquid chromatography-mass spectrometry conformation of the synthetic steps and the molecular masses of compounds depicted in FIG. 1, FIG. 2 and FIG. 5. All PMOs in this application are fluorescently labelled unless specified otherwise.

Figure 9A:
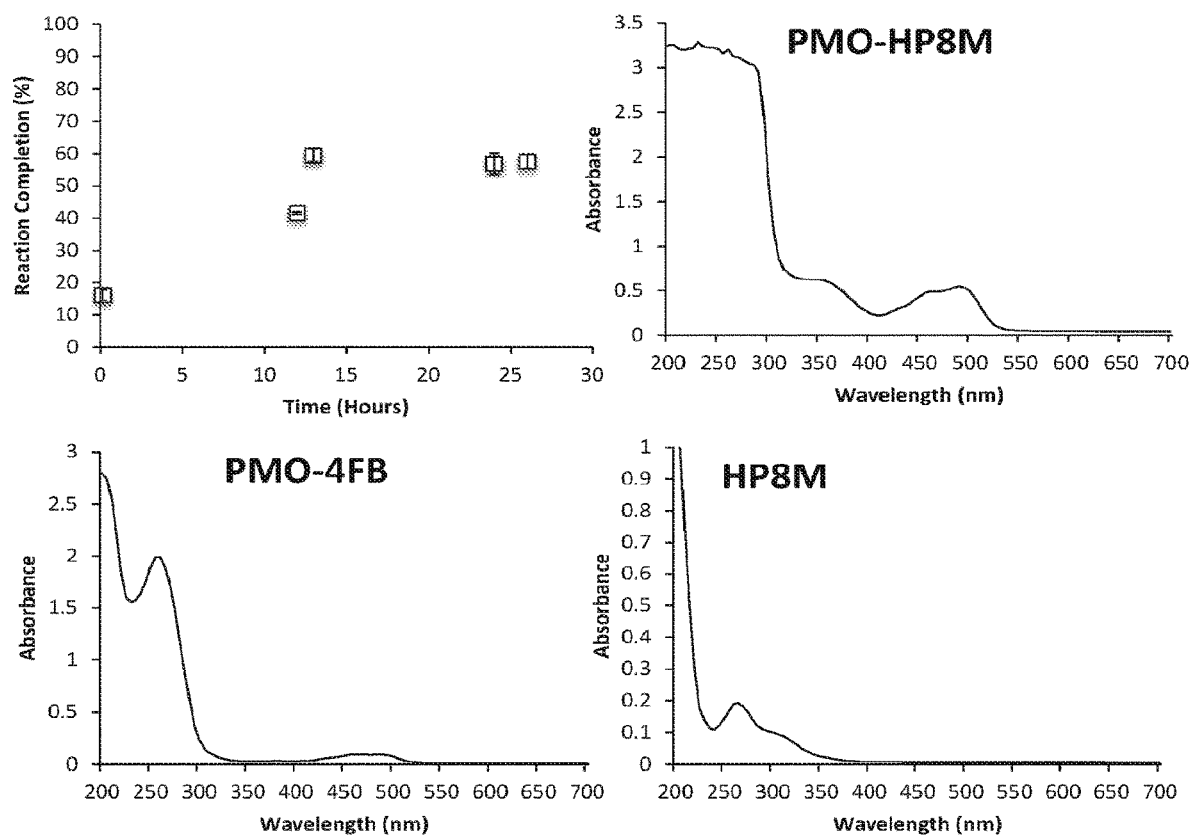
Figure 9B:
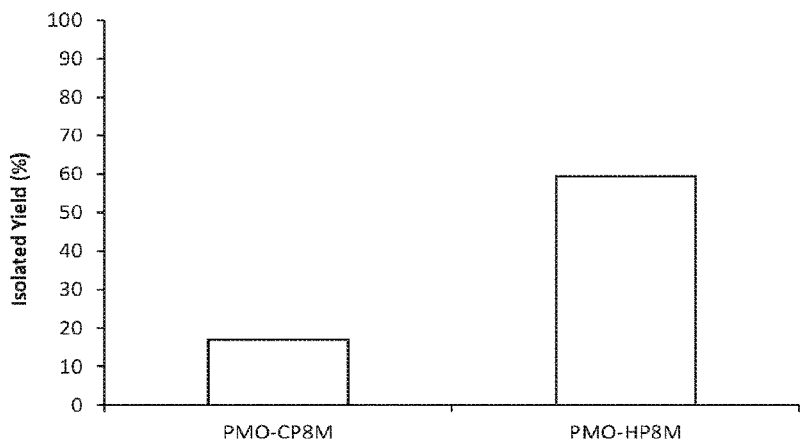

FIG. 8a is a LRMS (API-ES) mass spectra of CP8M-NC. Mass calculated for $C_{76}H_{130}N_{18}O_{16}S^{2+}$ $(M+2H)^{2+}$ 791.5 found 791.8;

FIG. 8b is a LRMS (API-ES) mass spectra of CP8M. Mass calculated for $C_{74}H_{125}N_{18}O_{16}S^{+}$ $(M+H)^{+}$ 1554.9 found 1554.5;

FIG. 8c is a LRMS (API-ES) mass spectra of CBM. Mass calculated for $C_{59}H_{95}N_{16}O_{10}S^{+}$ $(M+H)^{+}$ 1220.5 found 1220.1;

FIG. 8d is a LRMS (API-ES) mass spectra of HP8M. Mass calculated for $C_{77}H_{125}N_{20}O_{16}^{+}$ $(M+H)^{+}$ 1586.9 found 1586.5;

FIG. 8e is a HRMS (LQT-ESI) mass spectra of PMO. Mass calculated for $C_{332}H_{500}N_{153}O_{110}P_{25}$ (M) 9164.1675 found 9164.1882;

FIG. 8f is a HRMS (LQT-ESI) mass spectra of PMO-SMCC. Mass calculated for $C_{344}H_{513}N_{154}O_{113}P_{25}$ (M) 9383.2570 found 9383.2704;

FIG. 8g is a HRMS (LQT-ESI) mass spectra of PMO-CP8M. Mass calculated for $C_{418}H_{638}N_{172}O_{129}P_{25}S^{+}$ $(M+H)^{+}$ 10937.1806 found 10937.2377;

FIG. 8h is a HRMS (LQT-ESI) mass spectra of NF-PMO-CP8M. Mass calculated for $C_{393}H_{619}N_{172}O_{121}P_{25}S$ (M) 10490.0372 found 10490.2268;

FIG. 8i is a HRMS (LQT-ESI) mass spectra of PMO-HP8M. Mass calculated for $C_{417}H_{626}N_{173}O_{127}P_{25}$ (M) 10863.1285 found 10863.0716;

FIG. 8j is a LRMS (API-ES) mass spectra of FITC 3+ (CP8M-3). Mass calculated $C_{92}H_{132}N_{18}O_{20}S^{2+}$ $(M+2H)^{2+}$ 920.5 found 921.0;

FIG. 8k is a LRMS (API-ES) mass spectra of FITC 2+ (CP8M-2). Mass calculated $C_{92}H_{131}N_{17}O_{20}S^{2+}$ $(M+2H)^{2+}$ 913.0 found 913.6;

FIG. 8l is a LRMS (API-ES) mass spectra of FITC 1+ (CP8M-1). Mass calculated $C_{92}H_{129}N_{14}O_{20}S^{+}$ $(M+H)^{+}$ 1783.1 found 1782.6;

FIG. 8m is a LRMS (API-ES) mass spectra of FITC+ (CP8M-0). Mass calculated $C_{92}H_{126}N_{11}O_{20}S^{-}$ $(M-H)^{-}$ 1738.1 found 1738.0;

FIG. 8n is a HRMS (LQT-ESI) mass spectra of PMO-4-FB. Mass calculated for $C_{340}H_{503}N_{153}O_{112}P_{25}^{+}$ $(M-H)^{+}$ 9295.1802 found 9295.2168; and FIG. 8o is a HRMS (LQT-ESI) mass spectra of PMO-CP8M-NC. Mass calculated for $C_{420}H_{642}N_{172}O_{129}P_{25}S^{+}$ $(M-H)^{+}$ 10965.2112 found 10965.2162;

FIGS. 9a and 9b demonstrate the comparative conjugation efficiencies of SMCC and HNA linker systems;

FIG. 9a shows the % Conversion of HP8M and PMO-4FB into PMO-HP8M analysed by UV spectroscopy. % Conversion was calculated by $A_{350}$ of the bis-aryl hydrozone bond based on the starting reaction concentration of 705 µM. UV profiles of corresponding starting materials (HP8M and PMO-4FB) and the resulting conjugate (PMO-HP8M); and FIG. 9b shows the % isolated yield of PMO-CP8M and PMO-HP8M.

Figure 10A:
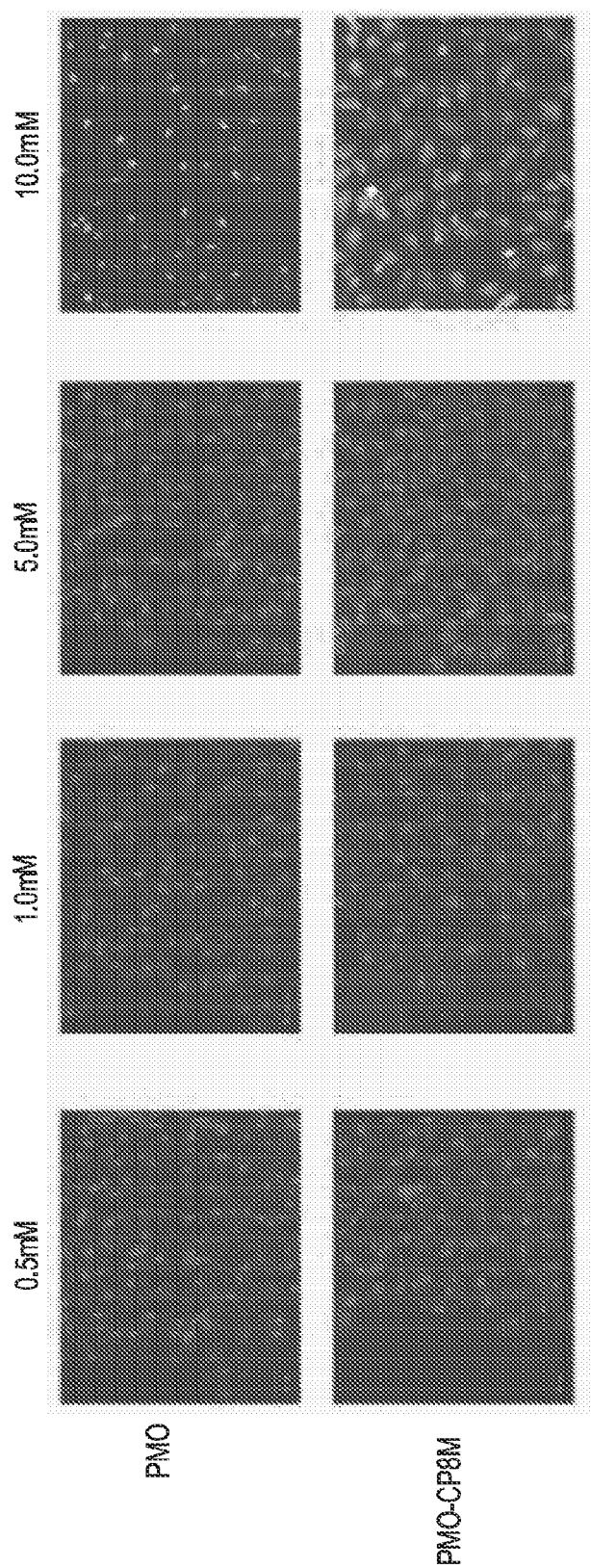

FIG. 10a shows florescence microscopy images demonstrating a dose dependent increase in DCCPM delivery into a human osteosarcoma cell line (U2OS) maintained in culture, without transfection reagent. The biologically active compound was a PMO with a sequence:

```
SEQ ID NO 1:
5'GGCCAAACCTCGGCTTACCTGAAAT3'
```

Figure 10B:
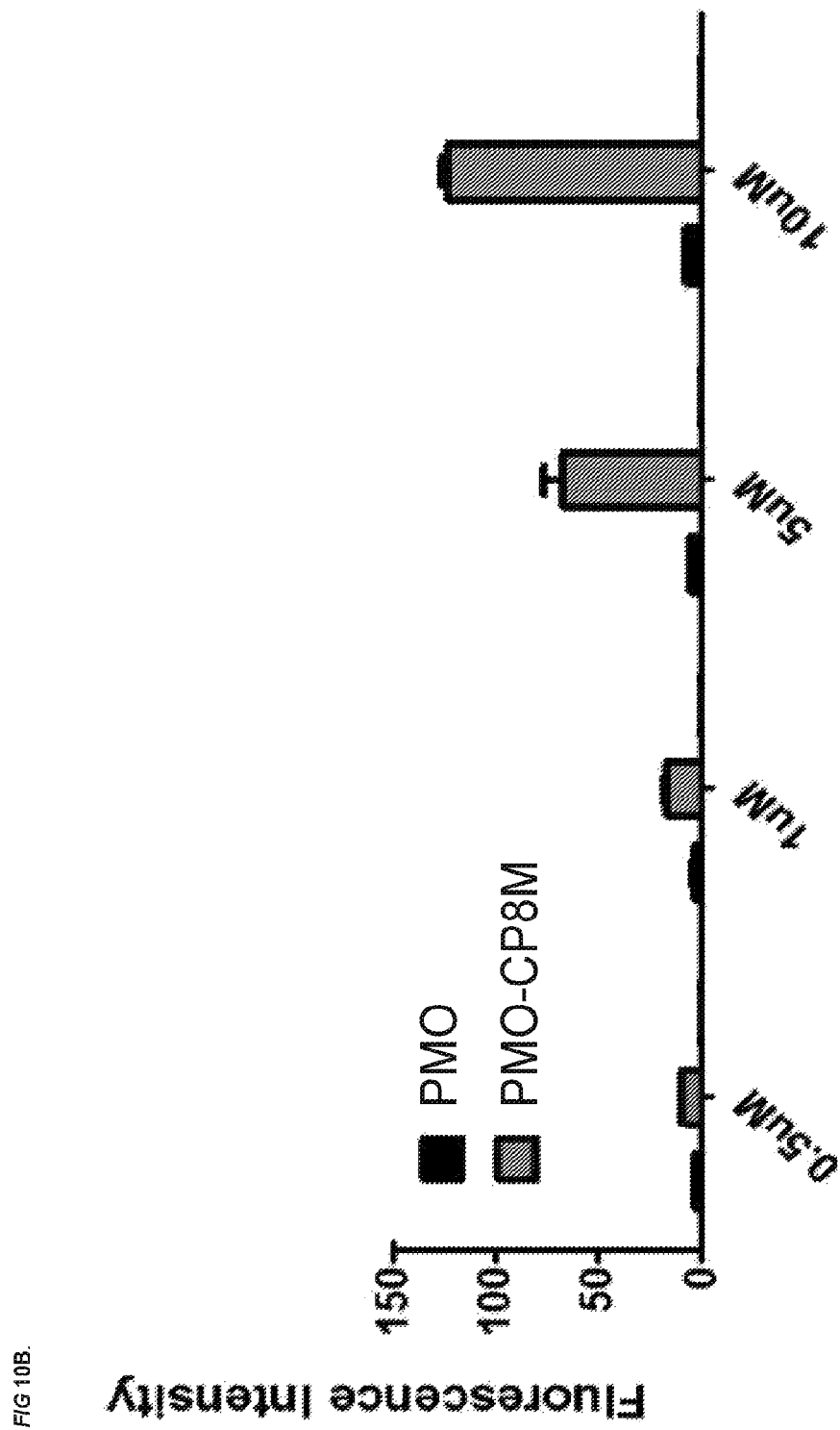
Figure 11:
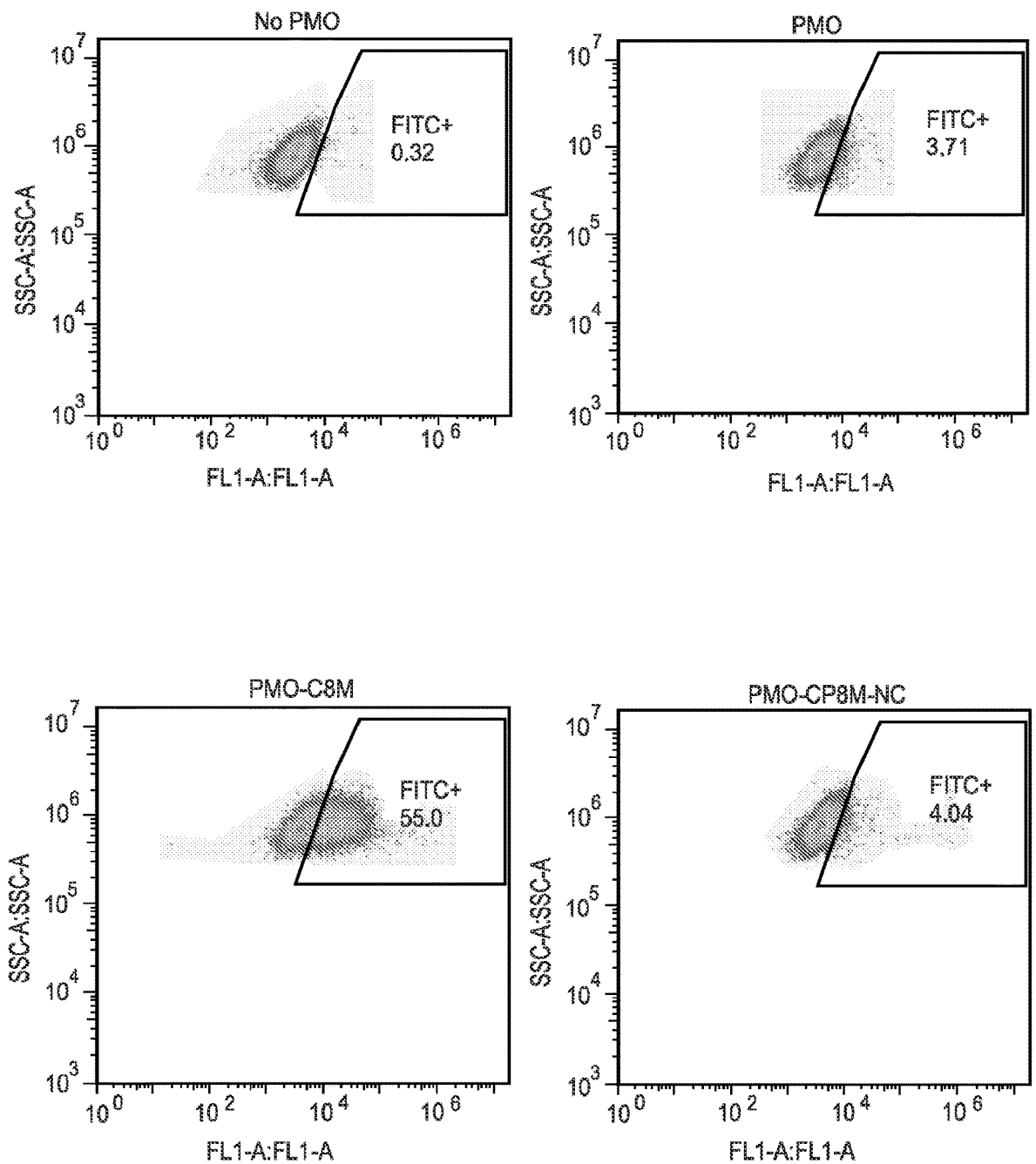

(an antisense reagent targeted to exon 23 of the mouse dystrophin gene, that causes the exclusion of exon 23 during mRNA splicing maturation); the bi-functional linker was a PEGylated SMCC; and the StaP was RKF-S5-RLF-S5 (SEQ ID NO: 57). This configuration of DCCPM is depicted as PMO-CP8M in the subsequent figs; unconjugated PMO acts as a control. All compounds were added to U2OS cells maintained in culture, without transfection reagent for 4 hours;

FIG. 10b is a graphical representation of the delivery of PMO and PMO-CP8M into a human osteosarcoma cell line (U2OS) maintained in culture without transfection reagent;

FIG. 11 is the analysis of PMO uptake into HEK293T cells by flow cytometry. Cells were incubated without PMO or with 1 µM PMO, 1 µM PMO-C8M or 1 µM PMO-CP8M-NC (all fluorescein-labelled) at 37° C. for 4 hours. Fluorescence was measured after washing the cells with PBS.

Figure 12A:
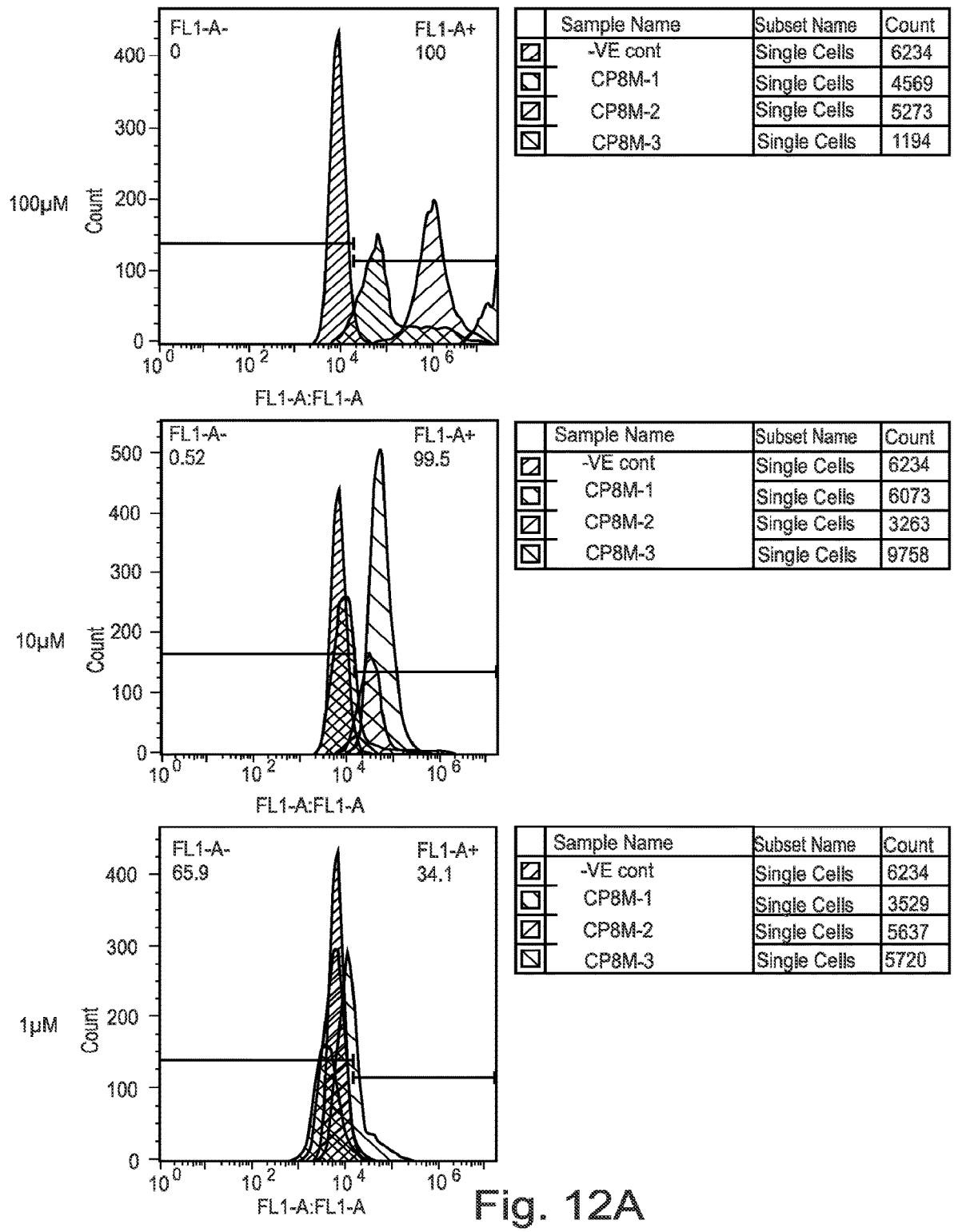
Figure 12B:
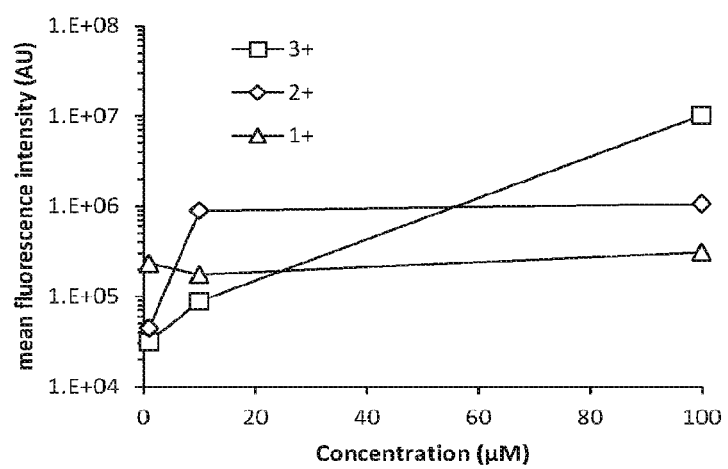
Figure 13:
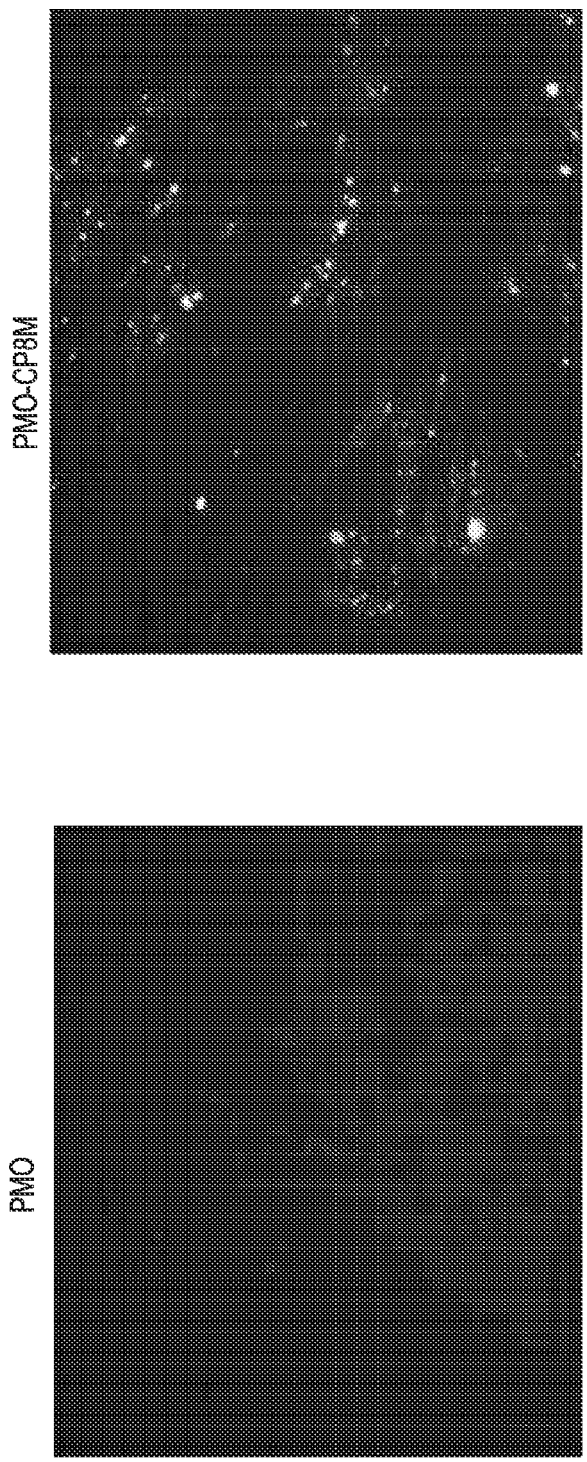

FIG. 12a shows flow cytometry analysis of HEK293T cells treated with FITC+3 (CP8M3), FITC+2 (CP8M-2) and FITC+1 (CP8M-1) without transfection reagent for 4 hours;

FIG. 12b shows flow cytometry analysis of HEK293T cells treated with FITC+3 (CP8M3), FITC+2 (CP8M-2) and FITC+1 (CP8M-1) without transfection reagent for 4 hours. The graph represents mean fluorescent intensity of FL1;

FIG. 13 shows fluorescence microscopy images either 5 µM PMO-CP8M or 5 µM PMO delivery into a mouse cell line that harbours the mdx mutation of the dystrophin gene (H2K mdx) maintained in culture, without transfection reagent, in which the PMO has a fluorescent label.

Figure 14:
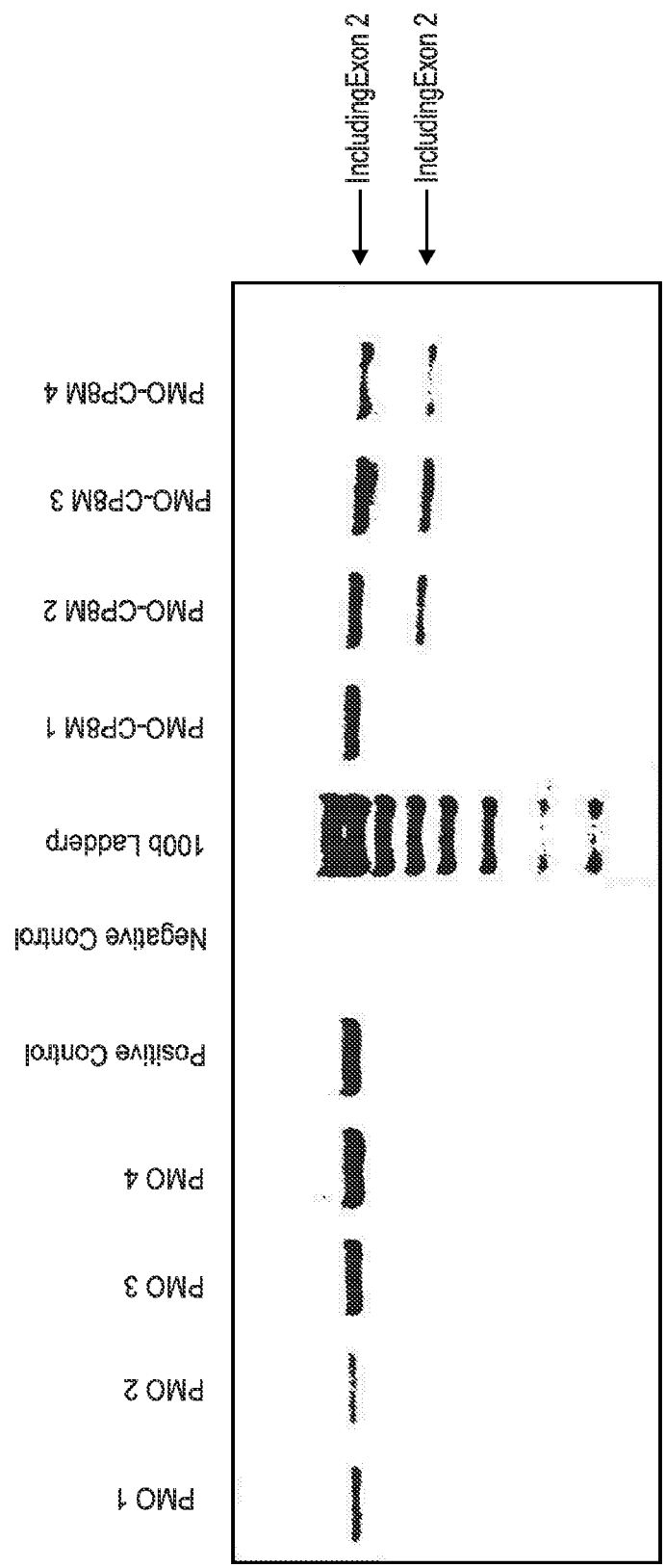
Figure 15:
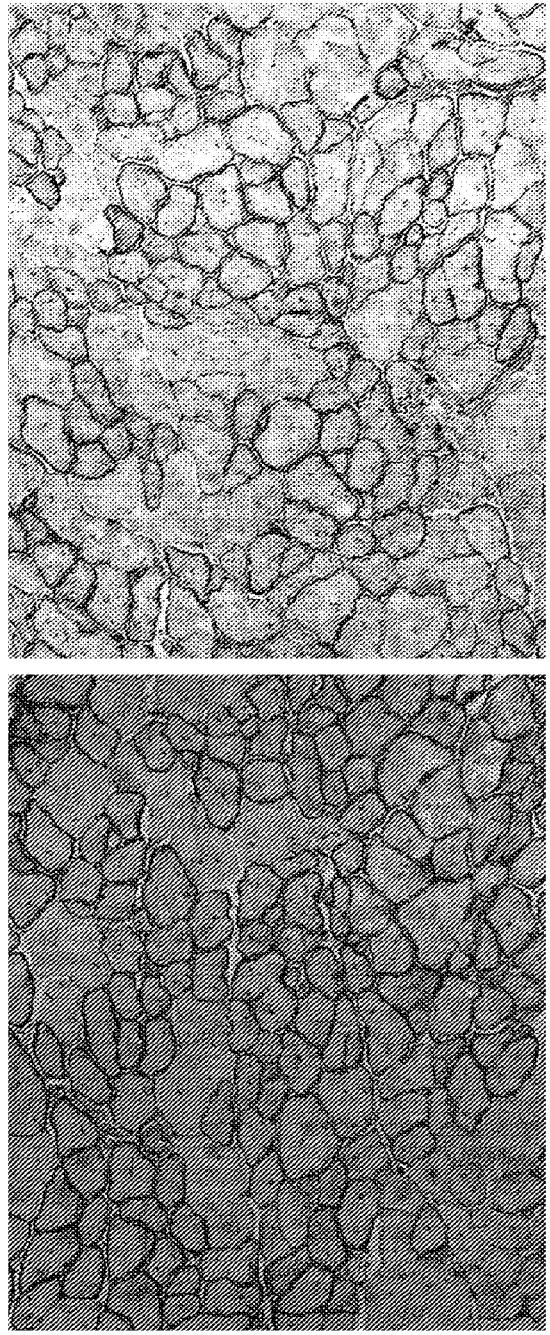
Figure 16:
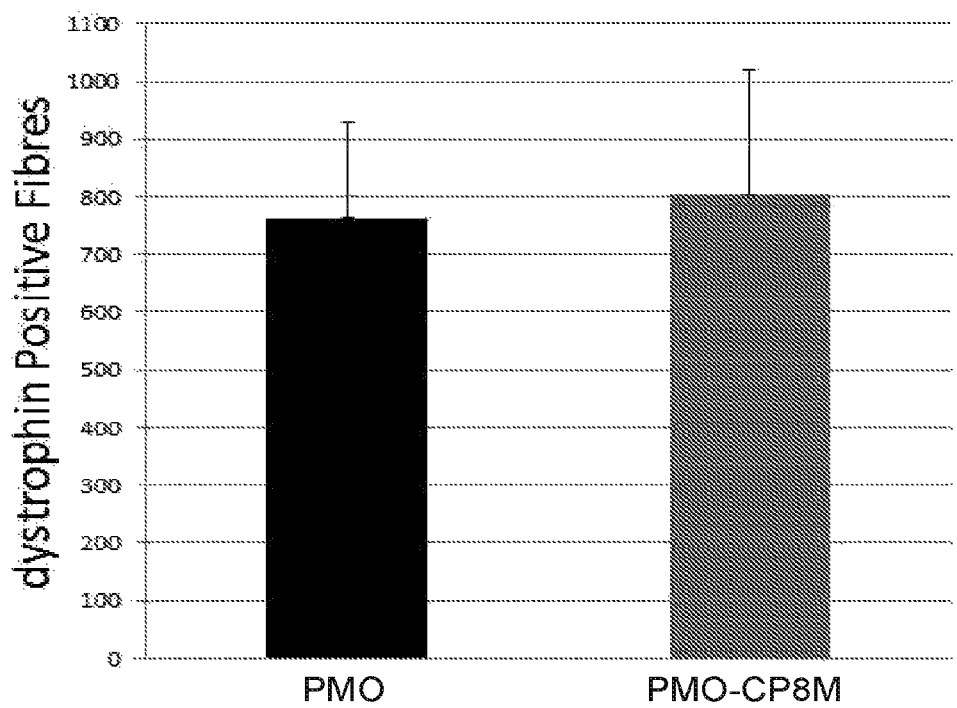
Figure 17A:
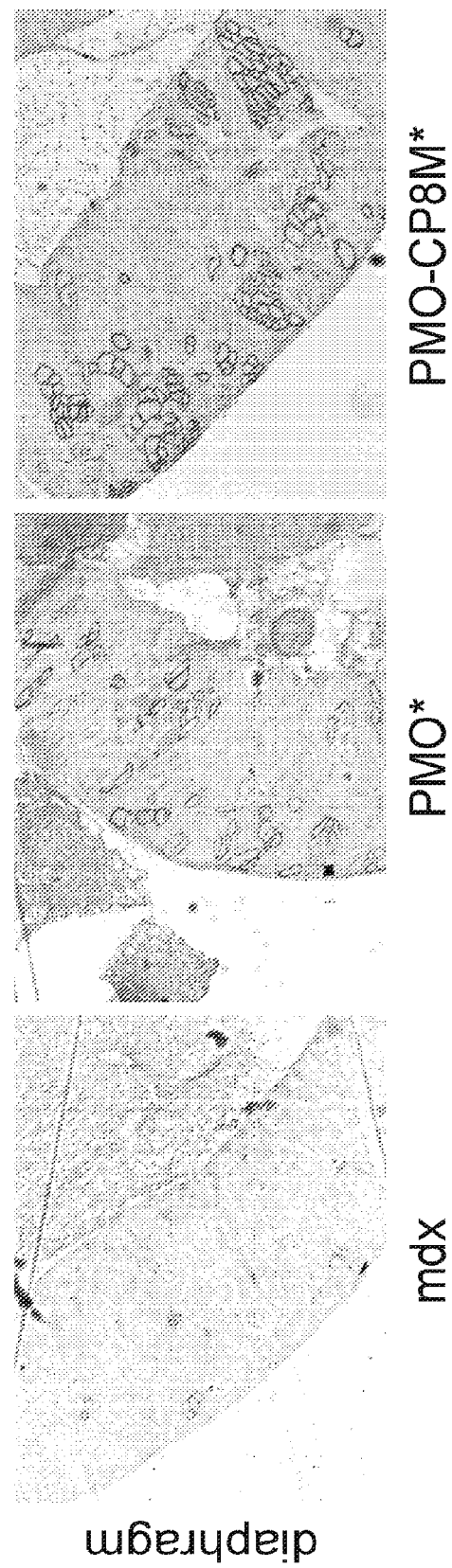
Figure 17B:
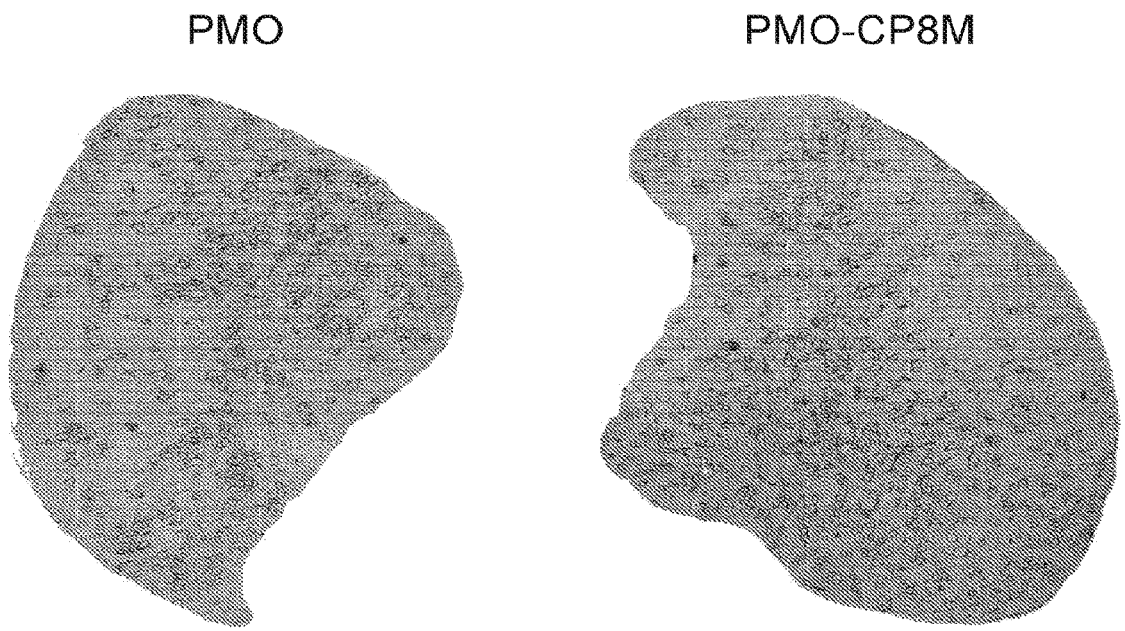
Figure 17C:
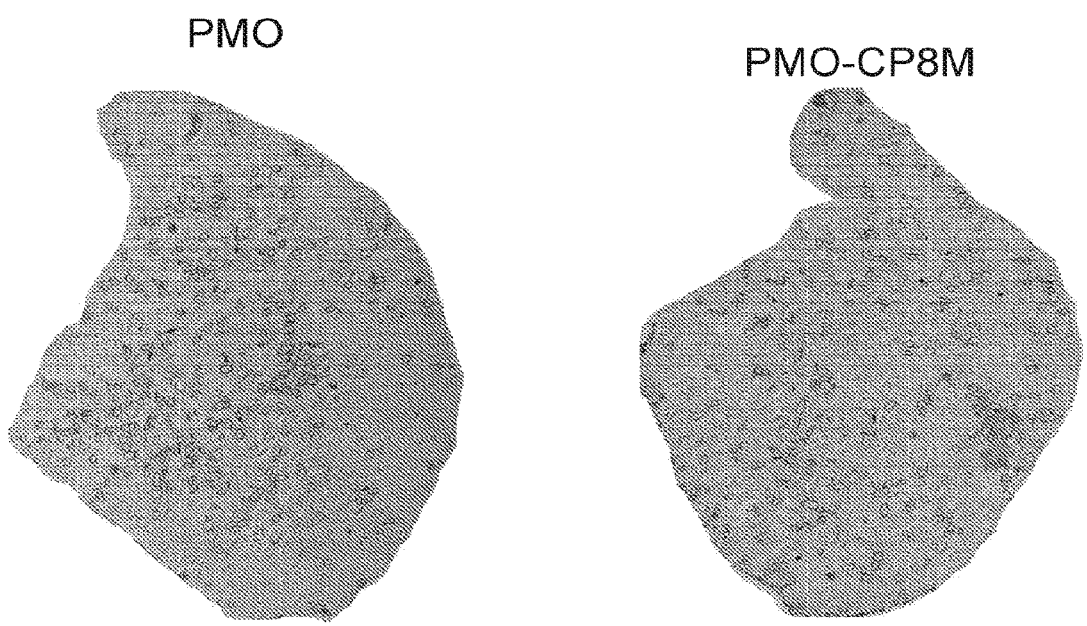
Figure 17D:
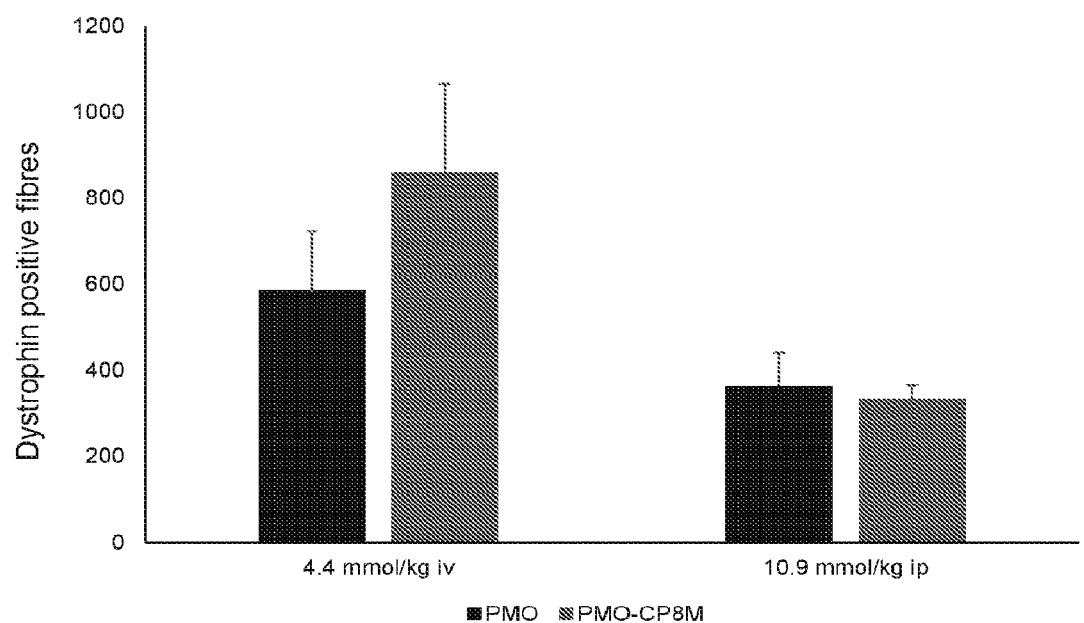
Figure 18A:
Figure 18A:
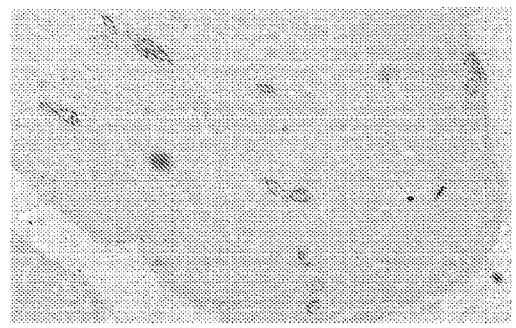
Figure 18B:
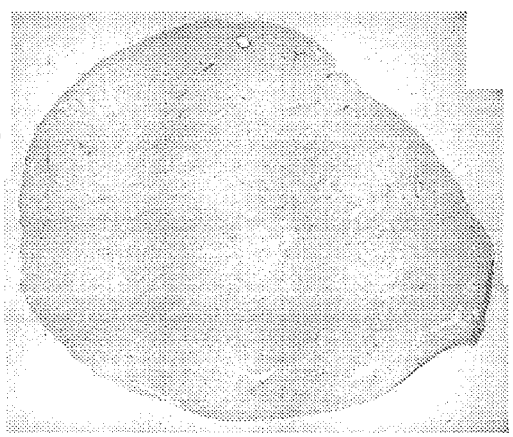
Figure 18B:
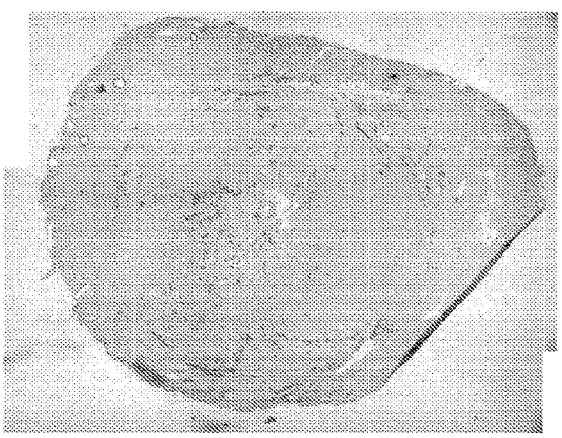
Figure 18C:
Figure 18C:
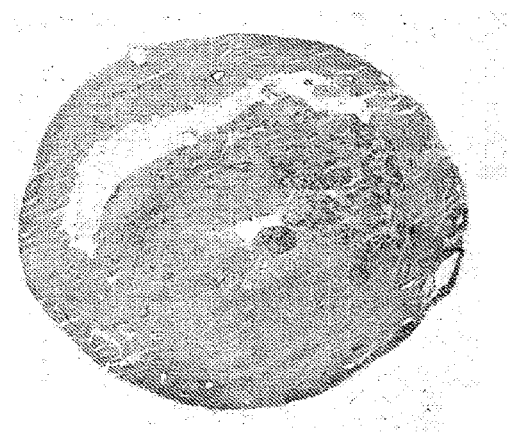
Figure 18D:
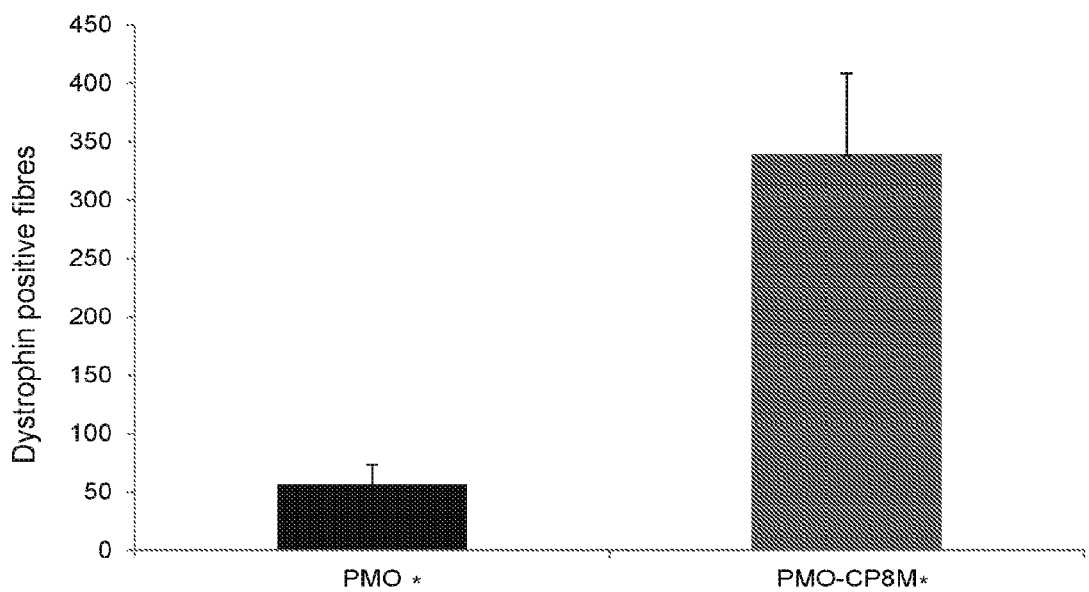
Figure 18E:
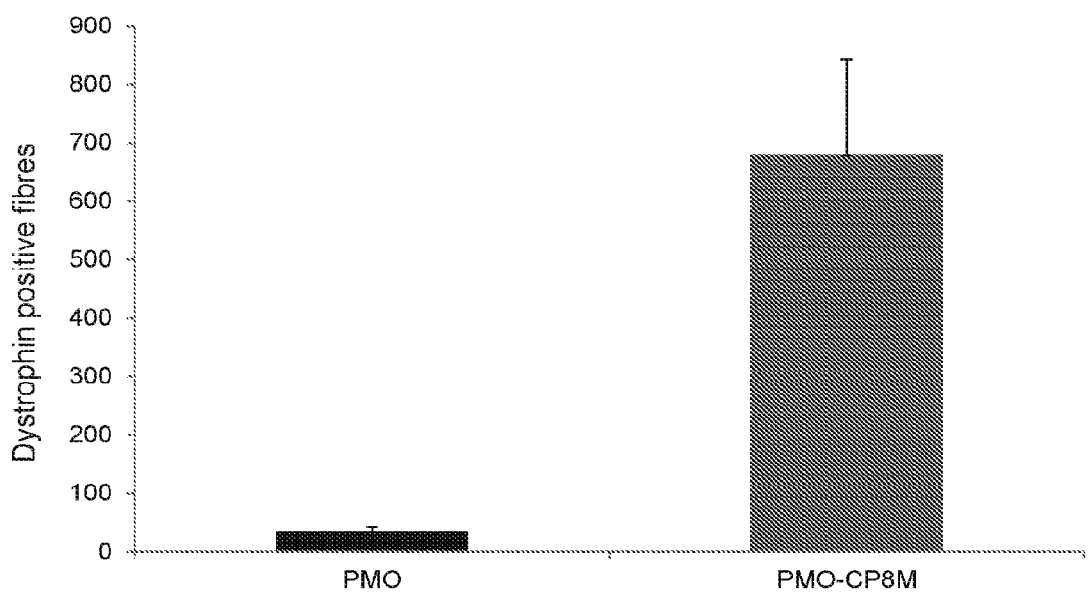
Figure 19:
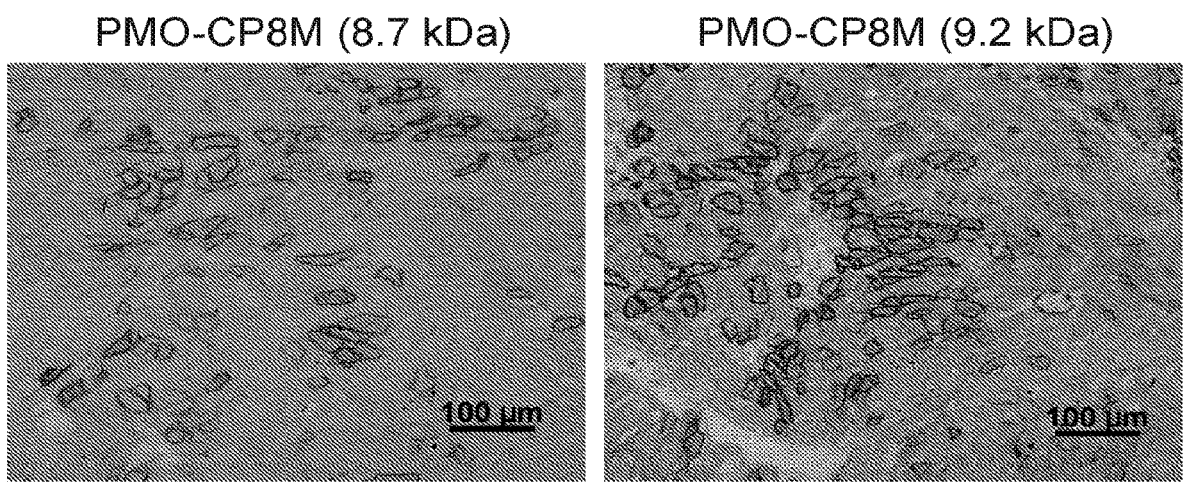
Figure 20:
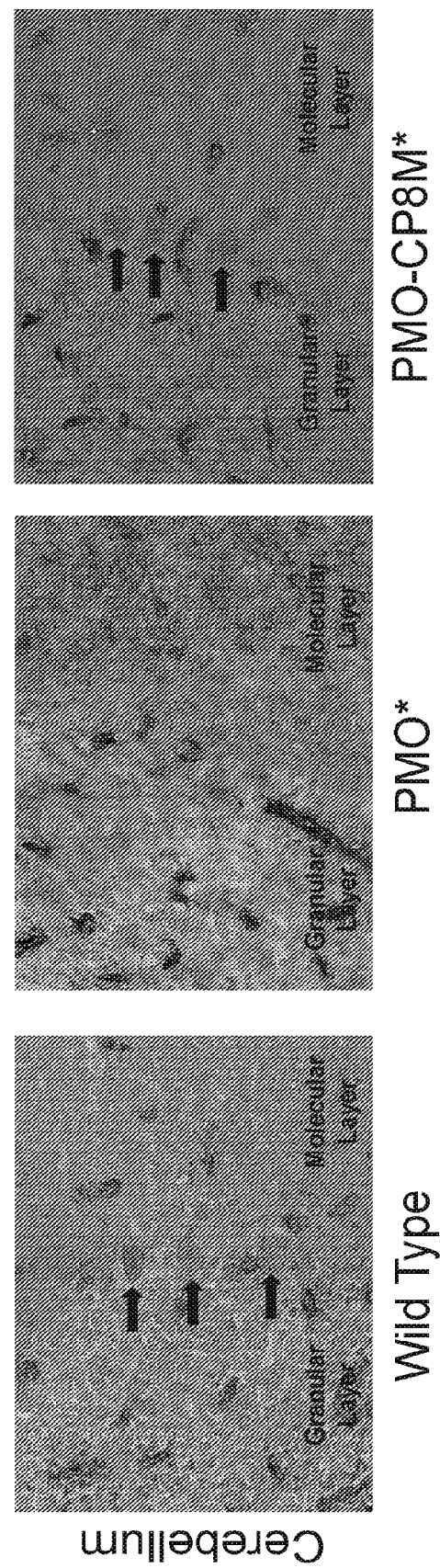
Figure 21:
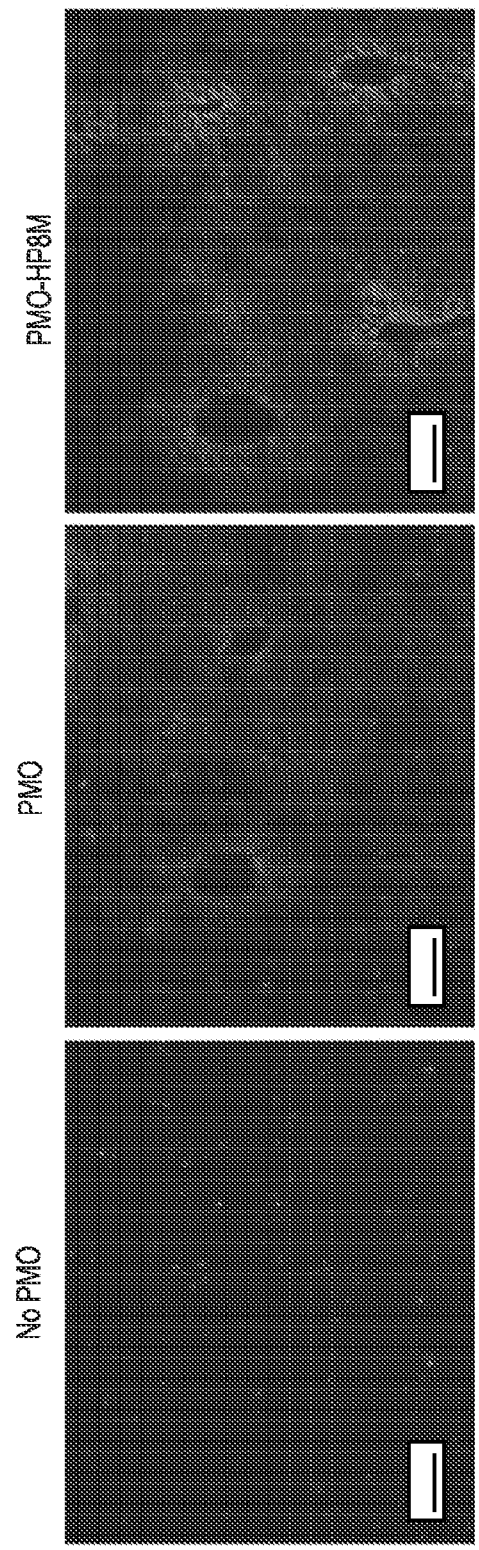

FIG. 14 shows an agarose gel electrophoresis image demonstrating that exon exclusion of the mouse dystrophin exon 23 is restricted to H2K mdx cells that have been transfected with 5 µM PMO-CP8M but not those treated with 5 µM PMO alone, in which the PMOs have a fluorescent label. 24 hours after incubation with PMO-CP8M or PMO, H2K mdx cells were recovered and RNA isolated. The RNA was reversed transcribed and an amplification between exon 20 and 26 of the mouse dystrophin gene, followed by a nested amplification between exon 20 and 26 was performed to yield a full length product of 901 bp fragment if exon 23 is present or 688 bp fragment if exon 23 is excluded;

FIG. 15 shows immuno-cytochemical staining for dystrophin from Tibialis anterior muscles of mdx mice following a single intramuscular injection of either 2.2 nmol PMO-CP8M or 2.2 nmol PMO into the Tibialis anterior muscle (dose in respect of molarity of PMO). Muscles were recovered 7 day post administration;

FIG. 16 shows a graphical representation of the number of skeletal muscle fibre being positive for an immuno-cytochemical staining for dystrophin from Tibialis anterior muscles of mdx mice injected with either 2.2 nmol PMO-CP8M or 2.2 nmol PMO. All dose are given in respect of the molarity of PMO;

FIGS. 17 a-d show immuno-cytochemical staining for dystrophin from skeletal muscles of mdx mice:

FIG. 17a is from the diaphragm following a single intraperitoneal injection of 1 μmol/kg PMO-CP8M or 1 μmol/kg PMO [* denotes non fluorescent labelled PMO]. Muscles were recovered 7 days post administration;

FIG. 17b is following multiple intravenous injections—total 4.4 μmol/kg PMO-CP8M or 4.4 μmol/kg PMO;

FIG. 17c is following multiple intraperitoneal injections—total 10.9 μmol/kg PMO-CP8M or 10.9 μmol/kg PMO; and FIG. 17d is a graphical representation of the number of skeletal muscle fibre being positive for an immuno-cytochemical staining for dystrophin following intraperitoneal administration. All dose are given in respect of the molarity of PMO [* denotes non fluorescent labelled PMO]. Muscles were recovered 14 days post administration;

FIGS. 18a-18c show immuno-cytochemical staining for dystrophin from heart muscles;

FIG. 18a is of mdx mice following a single intraperitoneal injection of 1 μmol/kg PMO-CP8M or 1 μmol/kg PMO. Muscles were recovered 7 days post administration;

FIG. 18b is following multiple intraperitoneal injections—total 7.6 μmol/kg PMO-CP8M or 7.6 μmol/kg PMO. Muscles were recovered 14 days post administration;

FIG. 18c is following multiple intraperitoneal injections—total 10.9 μmol/kg PMO-CP8M or 10.9 μmol/kg PMO;

FIG. 18d is a graphical representation of the number of cardiac muscle fibre being positive for an immuno-cytochemical staining for dystrophin following a multiple intraperitoneal injections—total 7.6 μmol/kg PMO-CP8M or 7.6 μmol/kg PMO; and FIG. 18e is a graphical representation of the number of cardiac muscle fibre being positive for an immuno-cytochemical staining for dystrophin following multiple intraperitoneal injections—total 10.9 μmol/kg PMO-CP8M or 10.9 μmol/kg PMO. All dose are given in respect of the molarity of PMO [* denotes non fluorescent labelled PMO]. Hearts were recovered 14 days post administration;

FIG. 19 shows immuno-cytochemical staining for dystrophin from heart muscles of mdx mice following intraperitoneal injections of PMO-CP8M with a total cargo size of 8.7 KDa and PMO-CP8M with total cargo size of 9.2 KDa. Hearts were recovered 14 days post administration;

FIG. 20 shows immuno-cytochemical staining for dystrophin from the cerebellum of mdx mice following a single intraperitoneal injection of 1 μmol/kg PMO-CP8M or 1 μmol/kg PMO. All dose are given in respect of the molarity of PMO [* denotes non fluorescent labelled PMO]. Cerebella were recovered 7 days post administration; and FIG. 21 demonstrates in vivo liver cell uptake of fluorescein-labelled PMO after intravenous administration of PMO or PMO-HP8M to mdx mice (single intravenous injection, 1 μmol/kg, analysed 2 weeks post-injection). Un-injected mdx mice were used as a negative control.

DETAILED DESCRIPTION

The invention is illustrated with reference to a single example which proves the benefit of the claimed invention.

An exemplary drug carrying cell penetrating molecule (DCCPM) was produced with a FITC label in order to demonstrate cellular uptake (Example 1).

The exemplary DCCPM comprises:
i) a biologically active compound (BAC)— (see Table 4 for non-limiting examples);
ii) a cell penetrating agent (CPA) which is a stabilized peptide (See Table 2 for non-limiting examples); and
iii) a bi-functional linker (BFL) (see Table 5 for non-limiting examples).

The three components forming the DCCPM are described in more detail below, although as illustrated in FIG. 5, the BAC and CPA can be linked directly (FIG. 6).

1. The Biologically Active Compound.

The biologically active compound is any compound that can exert a biological effect within a biological cell. Preferably, though not essentially, the BAC is one which will impact on the expression of one or more endogenous or exogenous genes. Examples include nucleic acids, DNAzymes, ribozymes, aptamers and pharmaceuticals. Preferred biologically active compounds for use in the present invention include electrically neutral oligonucleotides (charge −1 to +1 at physiological pH—about 7.5) such as polynucleic acids (PNAs) or PMOs or their modified derivatives that might impart a small electric charge (either positive or negative).

The biologically active compound may be used as a steric blocking compound to suppress or enhance: i) RNA splicing; ii) protein translation or iii) other nucleic acid:nucleic acid or nucleic acid:protein interactions, altering the gene expression of endogenous or exogenous (pathogen derived) genes.

The hybridisation of ON's to specific RNA sequence motifs prevents correct assembly of the spliceosome, so that it is unable to recognise the target exon(s) in the pre-mRNA and hence excludes these exon in the mature gene transcript. Exclusion of an in-frame exon can lead to a truncated yet functional gene product; exclusion of an out of frame exon results in a frame-shift of the transcript, potentially leading to a premature stop codon and a reduction in the target gene expression level.

Additionally, ON's can be designed to target 5' translation initiation start sites of endogenous or viral gene transcript(s) to prevent binding of the translational machinery. Using ASO to suppress viral translation is a well-established technology and has progressed into clinical trials for viral haemorrhagic fevers such as Marburg and Ebola.

Also, ON can be designed to target 3' untranslated region of an endogenous transcript that alters the stability of the transcript. Such targets include, and are not limited to, poly adenylation and/or cleavage sites of the transcript.

Also, ON can be designed to form aptamers such that the secondary and tertiary structures can bind proteins or other cellular targets thus impacting on specific gene expression levels.

Non-limiting exemplary ON chemistries are illustrated in Table 4.

In the non-limiting example illustrated, the target is exon 51 of the dystrophin gene and comprises the sequence:

```
SEQ ID NO 2:
5'CUCCAACAUCAAGGAAGAUGGCAUUUCUAG3'
```

2. The Cell Penetrating Agent (CPA) which is a Stabilized Peptide

The cell penetrating agents of the invention are stabilized peptides.

The peptides may be stabilized by stapling, to form a stapled peptide (StaP), or by stitching to form a stitched peptide (StiP)

All-hydrocarbon staples and stitches may confer a property, e.g. an α-helical structure, protease resistance, cellular penetrance, and biological activity.

Non-limiting examples of stapled and stitched peptide sequences are illustrated in Table 2 and include peptide sequences including S5, S8 and B5 (as defined in Table 2).

Stabilisation of e.g. the α-helical structure can be achieved by, for example, a ring-closing metathesis and may be catalysed by a variety of ruthenium catalysts including Grubbs generations 1 and 2 and Grubbs-Hoyveda generations 1 and 2.

All the peptide components (amino acids, unnatural amino acids, unstapled/unstitched, partially stapled/stitched and stapled/stitched peptides) may exist in specific geometric or stereoisomeric forms. All compounds include cis- and trans-isomers, (R)- and (S)-enantiomers, diastereoisomers and racemic mixtures thereof.

Preferred isomer/enantiomers will be enriched to give a greater proportion of one particular isomer or enantiomer. Embodiments thereof may be made of greater than 90%, 95%, 98% or 99%, by weight, of a preferred isomer/enantiomer.

Non-limiting examples of unnatural amino acids used in stabilising a peptide structure are illustrated in Table 1.

In one embodiment the applicant employs α,α-disubstituted unnatural amino acids bearing all-hydrocarbon tethers (e.g. α-methyl,α-pentenyl glycine).

For single turn stapling, one embodiment could employ a (S)-pentenylalanine (S5) at, e.g. i, i+4 positions, and in another embodiment, for double turn stapling, a combination of either R-octenylalanine/S-pentenylalanine (R8/S5) or S-octenylalanine/R-pentenylalanine (S8/R5) at e.g. i, i+7 positions can be used. The same pairings can be used to install more than one staple within a given peptide template. S5 can be substituted at i, B5 at position i+4 positions, and S8 can be been substituted at i, i+4, i+11 positions to generate stitched peptides. The S5 configured amino acid and its enantiomer R5, or S8 configured amino acid and its enantiomer R8, differ only in the opposite stereochemical configuration of the staple they bear.

Based upon the inclusion of a single or a double turn staple, peptides may comprise of one or more of the sequences in Table 2. Based upon the specific peptides shown in Table 2, a person skilled in the art can easily envisage peptides with 3, 4, 5 or more turn stabilising staples.

The hydrocarbon bridge may be composed of a double hydrocarbon bond or a single hydrocarbon bond.

In one embodiment the cell penetrating agent has a stitch or staple peptide comprising the sequence RFK-S5-RLF-S5 (SEQ ID NO: 57).

In another embodiment the peptide is a branched stapled peptide. The branched stapled peptide comprises of 2 or more chains of peptides. Branched peptides may be formed using any method know to the art; in one embodiment a lysine residue is used to branch two peptide chains.

Functional derivatives of disclosed peptide sequences could be used. Functional derivatives may have representative fragments or homologues or peptides that include insertions to the original peptide. Typical derivative would have 70%, 80%, 90% or more of the original peptide sequence and may have up to 200% of the number of amino acids of the original peptide. The derivatives would be used to enhance the delivery of a biologically active compound.

Peptide sequence can include modified amino acids to include functional groups that permit the addition of other moieties. Non-limiting examples of such moieties include an acetyl, a cholesterol, a fatty acid, a polyethylene glycol, a polysaccharide, an aminoglycan, a glycolipid, a polyphenol, a nuclear localising signal, a nuclear export signal, an antibody and a targeting molecule.

3. Bi-Functional Linker

A bi-functional linker may be used to link the BAC to the CPA.

Preferred linkers will link between, for example, an amine group on the BAC and a sulfhydryl (thiol) group (usually a cysteine residue) on the CPA terminus. Examples of substrates to achieve this include, but are not limited to, SMCC (succinimidyl 4-(N-maleimidomethyl)cyclohexane-1-carboxylate), AMAS (N-α-maleimidoacet-oxysuccinimide ester, BMPS (N-β-maleimidopropyl-oxysuccinimide ester), GMBS (N-γ-aleimidobutyryl-oxysuccinimide ester), DMVS (N-δ-maleimidovaleryl-oxysuccinimide ester, EMCS (N-ε-malemidocaproyl-oxysuccinimide ester), and LC-SMCC (Succinimidyl 4-(N-maleimidomethyl)cyclohexane-1-carboxy-(6-amidocaproate) as exemplified in Table 5.

Another preferred linker system is hydrazynal nicotinic acid (HNA), however if the BAC is a PMO, the PMO is modified to incorporate 4 formyl benzioic acid.

Other linkers such as DSG (disuccinimidyl gluterate) and DSCDS (disuccinimidyl-cyclohexl-1,4-diester) will include the ability to link the 5'-amino group of the BAC to the N-terminus of the CPA (Table 5, entries 8 and 9).

Linkers may include other elements that confer a desirable property on the DCCPM e.g. spacer between ON and CPA or an element that will enhance solubility, for example a PEGylated element as illustrated in FIGS. 5c and 5d. Non-limiting examples are shown in Table 5.

The biologically active compound is covalently attached to the chimeric cell delivery peptide. Again, this can be done using any method known in the art. Preferably, the cell delivery peptide is attached to the biologically active compound by means of a disulphide bridge or a thiol maleimide linker e.g. SMCC; the attachment may be by means of an amide linker or an oxime linker or a thioether linker.

Example 1: (Proof of Principle)

DCCPM to Enhance RNA Steric Blocking in Treating Duchenne Muscular Dystrophy (DMD).

INTRODUCTION

Duchenne muscular dystrophy (DMD) is the most common inherited lethal childhood disease in the world, with a worldwide incidence of approximately 1 in 4000 live births[33]. This severe muscle-wasting disorder is caused in the majority of families by gene mutations leading to disruption of the reading frame and premature truncation of the protein dystrophin[34,35].

RNA splicing suppression of the DMD transcript has particular promise. The hybridisation of ASOs to specific RNA sequence motifs prevents correct assembly of the spliceosome, so that it is unable to recognise the target exon(s) in the pre-mRNA and hence excludes them in the mature gene transcript. ASO-mediated RNA splicing suppression resulting in the re-expression of a truncated, yet functional dystrophin protein has been demonstrated in vitro and in the pre-clinical mdx mouse model[29,36-41], which led to clinical development programs[8,13].

Although intravenously administered PMOs have demonstrated a dose-dependent increase in dystrophin re-expression with some functional benefit[13,42], skeletal muscle dystrophin restoration is still very variable between patients after many multiple administrations. Importantly, many other target tissues (e.g. brain and heart) remain refractory to PMO transfection even when repeat administration or high dose strategies are employed[27-29].

To date unmodified CPA conjugation improves PMO bio-distribution and serum stability[30-32], however toxicity is still a major roadblock for pipeline development[19].

Applicant hypothesised that a CPA based upon a stabilized e.g. StaP (or StiP) conjugated to a PMO known to cause RNA splicing suppression of the DMD transcript, would lead to a greater level of dystrophin restoration and re-expression of dystrophin in tissues refractory to naked PMO without the potential for CPA related toxicity.

Materials and Methods

Nuclear Magnetic Resonance (NMR) Analysis of StaP $^1$H NMR spectra was recorded using a Bruker Avance III 500 (500 MHz) spectrometer. Samples were dissolved in $H_2O$ with 10% $D_2O$ and 10 mM sodium acetate.

NOESY spectra were recorded with a 12626.263 Hz sweep width, 4096 complex points (DQD acquisition mode) in the direct dimension and 1024 indirect points (States-TPPI acquisition mode). A NOESY mixing time of 250 ms was used to provide cross peaks with high signal to noise while largely avoiding spin diffusion. A pre-saturation pulse on water and a 3-9-19 pulse sequence with 20% Z-gradients (4,5) aided solvent suppression. TOCSY spectra were recorded with the same spectral width and resolution as the NOESY with a homonuclear Hartman-Hahn transfer using the MLEV17 sequence for an 80 ms mixing time (6). Two power levels were used for excitation (3 dB) and spinlock (12.2 dB). Water suppression was achieved as with the NOESY.

High Resolution Mass Spectroscopy

High-resolution mass spectra were recorded on a Thermo scientific LQT Orbitrap XL under electron spray ionization conditions (ESI) or where indicated under Atmospheric Pressure Ionisation (API) condition.

Circular Dichroism (CD) Spectroscopy

CD analysis was performed on an Applied Photophysics Chirascan Circular Dichroism spectrometer. Samples were dissolved in $D_2O$ at 0.125 W/W % and data acquired in triplicate at room temperature and subsequently averaged and smoothed using built in qCD software. Graphs were plotted by subtracting a blank $D_2O$ spectrum from the acquired data to provided blank correction.

Synthesis of PMO-CP8M and NF-PMO-CP8M

PMO (22.2 mg, 2.1 µM) was dissolved in PBS (400 µL, 1 x) and incubated at room temp after the addition of SMCC linker (6 mg, 18 µM, 9x excess) dissolved in MeCN 100 µL. After 45 mins the mixture was desalted using sephadex g25 hydrated in a PBS 1x and was also used as the eluent. RCM-C-PEG-8Mer (3 mg, 2.5 µM) was mixed immobilised TCEP (750 µL) for 1 h. The SMCC modified PMO was then desalted into PBS/MeCN (500 µL 4:1) and immediately the peptide was eluted from the immobilised TCEP and stirred at room temp for 3 hours before purification on a Waters HLB column.

The solution was loaded onto 4 HLB columns, and washed with milliQ water to remove any salts then 20% MeCN in water and finally PMO-CP8M was removed with 50% MeCN in water. The MeCN content was reduced by rotary evaporation and the conjugate subsequently freeze dried to yield the final lipholysed compound.

Synthesis of PMO-HP8M

Modification of PMO to PMO-4FB.

4-FB (250 mg, 1.5 mM) was dissolved in DMF with COMU (1.2 g, 2.6 mM) and NHS (230 mg, 2.0 mM) and stirred for a few mins. Nb, 4-FB did not fully dissolve until DIEA was added. DIEA (0.54 mL 3.0 mM) was then added upon which the reaction mixture changed from colourless to pale yellow/orange. The reaction mixture was stirred for 1 h and monitored by TLC using 5% MeOH in DCM. The mixture was separated over DCM to remove DMF then purified by flash chromatography using DMC to elute the top spot staining positive with 2,4 DNP. Product was collected as an off white solid 112 mg (30%).

PMO (30.4 mg, 3 µM) was added to a solution of 4-FB and dissolved in Carbonate buffer:MeCN (50% MeCN) and NHS activated 4-FB (10 mg, 32 µM) was added and stirred overnight. The mixture was then desalted using sephadex G25 superfine with water:MeCN as an eluent. MeCN was removed by rotary evaporation and the remaining eluent was then freeze dried. Freeze dried product yielded 24 mg 83% yield.

Conjugation of PMO-4FB to HP8M

HP8M was dissolved in milliq ultra pure water (100 µL) to give a solution of 12 mg/mL. Aldehyde modified PMO (7 mg, 0.76 µM) was dissolved in water/MeCN (300 µL, 1:1) and desalted using sephadex G25 superfine and water/MeCN (1:1) as the eluent. The collected fraction was then diluted to 1 mL total volume in water:MeCN mix (1:1) and PMO content was analysed by UV/vis and found to be 6.5 mg/mL or 705 µM. HNA peptide and Analine (10 mM final conc) was then added and UV/vis monitored for evidence of $A_{354}$ and used to calculate the conjugation of PMO to peptide.

PMO and Peptide Synthesis

PMO were synthesised with a 5' amine group and 3' fluorescein isothiocyanate (FITC) label and purified >90% by Genetool LLC (Philomath, Oreg. USA). All peptides were synthesized following an established protocol using standard Fmoc-peptide chemistry on Rink amide MBHA resin. The coupling reactions were performed by the addition of a mixture of 10 equivalents of the amino acids, 9.9 equivalents of HCTU and 20 equivalents of DIPEA in NMP (equivalents relative to initial loading of Rink amide MBHA resin). The reactions were allowed to proceed for at least one hour. Coupling of non-natural amino acids (R/S5, R/S8 or 85) was performed with 4 equivalents of the amino acid, 3.9 equivalents of HCTU and 10 equivalents of DIPEA in NMP for two hours. The ring closing metathesis reaction of the olefin-containing non-natural amino acids was facilitated with Grubbs|catalyst (benzylidene-bis(tricyclohexylphosphine)-dichlororuthenium) dissolved to approximately 10 mg/mL in 1,2-dichloroethane (DCE) for two hours under nitrogen bubbling. Subsequently, excess catalyst was washed from the resin with DCE and then coupled with an N-terminal FITC. Upon completion, peptides were simultaneously cleaved from the resin and de-protected using a cleavage cocktail containing 95% TFA, 2.5% TIS and 2.5% water. Crude peptides were dissolved in 50% acetonitrile/water, passed through a 0.2 µm syringe filter, and purified by reverse phase HPLC using a C-18 column (Agilent, Palo Alto, Calif.). Compound identification and purity was assessed using coupled LC/MS (Agilent, Palo Alto, Calif.). Purified fractions were pooled and evaporated to remove acetonitrile and trace TFA by Speedvac and then lyophilized to dryness. A non-ring closed peptide was also produced as a control.

Cell Culture and Transfection

U2OS cells (Human osteosarcoma) were cultured in high glucose DMEM supplemented with 10% foetal calf serum (Sigma, UK) at 37° C. under an 8% CO2/92% air atmosphere.

$H_2K$ mdx mouse myoblasts were cultured at 33° C. under a 8% $CO_2$/92% air atmosphere in high-glucose DMEM supplemented with 20% foetal calf serum, 0.5% chicken embryo extract (PAA laboratories Ltd, Yeovil, UK), and 20 units/ml γ-interferon (Roche applied science, Penzberg, Germany). Cells were then treated with trypsin and plated at $8 \times 10^4/cm^2$ in 24-well plates coated with 0.1 mg/ml ECM gel (Sigma). $H_2K$ mdx cells were transfected 24 h after seeding with treatment in a final volume of 0.2 ml of normal growth media. Following 4 hours of transfection, the PMO or PMO-SAP was removed and replaced with DMEM supplemented with 5% horse serum. Fluorescence and RNA extraction was performed 48 hours post transfection.

HEK293T cells (Human embryonic kidney) were cultured in high glucose DMEM supplemented with 10% foetal calf serum (Sigma, UK) at 37° C. under an 8% $CO_2$/92% air atmosphere.

U2OS cells were incubated with PMO or PMO-CP8M at increasing concentration (0.5 μM, 1.0 μM, 5.0 μM and 10 μM) with any facilitation transfection reagent; H2K mdx mouse myoblasts were incubated with PMO or PMO-CP8M at 5.0 μM: HEK293T cells were incubated with CP8M (1.0 μM, 10 μM and 100 μM) and PMO, PMO-CP8M-NC, PMO-C8M at 1.0 μM. Levels of fluorescence was quantified at 494 nm to determine relative entry of respective compounds by microscopic or flow cytometry methodologies.

RNA Extraction and Nested RT-PCR Analysis

Total RNA was isolated from $H_2K$ mdx mouse myoblasts cells (RNeasy, Qiagen, UK). The RNA was reversed transcribed (nanoscript2, Primer Design UK) and an amplification between exons 20 and 26, followed by a nested amplification between exon 20 and 26 was performed to yield a full length product of 901 bp or 688 bp if the mouse dystrophin exon 23 was excluded. Products loaded in a 1% agarose gel (buffered with tris acetate 40 mM and 1 mM ethylenediaminetetraacetic acid).

Animals mdx mice, with access to chow and water ad libitum, were used in all experiments. All experiments were carried out in the Animal unit, School of Biological Science, University of Reading, Reading, UK according to procedures authorized by the UK Home Office. Mice were killed by $CO_2$ inhalation or cervical dislocation at desired time points, and muscles and other tissues were snap-frozen in liquid nitrogen-cooled isopentane and stored at −80° C.

Administration of PMO or PMO-CP8M

Intramuscular administrations: Tibialis anterior muscles of mdx mice were injected with either 2.2 nmol PMO or 2.2 nmol PMO-CP8M under isoflurane anaesthesia. Systemic administration: mdx mice were subject to a single or repeated intraperitoneal injections of PMO or PMO-CP8M (or non-fluorescently labelled variants) at doses ranging from 1 μmol/kg to 10.9 μmol/kg total delivery; alternatively, mdx mice were subject to single or repeated intravascular injections of PMO or PMO-CP8M ranging from 1 μmol/kg to 4.4 μmol/kg total. A series of tissues were recovered at the end of the experiment that included skeletal muscle, heart, brain and liver.

Histology and Immuno-Cytochemistry

For skeletal muscle, heart and brain, 10 μM cryosections were cut and dystrophin protein was detected using rabbit polyclonal antibody to dystrophin (ab15277; Abcam, Cambridge, UK). Routine haematoxylin and eosin staining was used to assess general pathology and morphology. For liver, 10 μM cryosections were dried and embedded in fluorescence-compatible mounting medium (Dako), and general fluorescence was assessed microscopically at 494 nm.

Flow Cytometry

Uptake of fluorescently-labelled PMO was determined by flow cytometry using an Accuri C6 flow cytometer. PMO-transfected cells were released with trypsin, washed in PBS and kept on ice before analysis. Cell fluorescence in single live cells was determined using FlowJo software after appropriate gating. Untreated cells were used to establish gating settings for the determination of the % fluorescein-positive cells.

Statistical Analysis

All data are reported as mean values±SEM. Statistical differences between treatment groups and control groups were evaluated by SigmaStat (Systat Software, UK) and student's t test was applied. Significance was accepted for p-values<0.05.

Results

Circular dichroism and the nuclear magnetic resonance data confirmed that the ordered structure of the peptides was as expected and that the stapled peptides adopted an α-helical structure (FIG. 4).

The conjugation of PMO-SMCC with a CPP to form PMO-CP8M has consistently yielded an efficiency of 10%. Surprisingly, adopting a conjugation based upon a PMO modified to incorporate 4 formyl benzioic acid and hydrazynal nicotinic acid (HNA) incorporated into the terminal end of the CPP, increased the efficiency of conjugation to yield PMO-HP8M at 59% (FIG. 9).

PMO was conjugated to the bi-functional linker (a PEGylated SMCC) and a CPP (RKF-S5-RLF-S5 (SEQ ID NO: 57)) as confirmed by mass spectrometry (FIG. 7). Subsequently PMO and PMO-CP8M were transfected into a standard cell line (U2OS) to determine if the CP8M conferred enhanced cell entry to the cell. Naked PMO were refractory to cell entry, giving only a background fluorescence signal, compared to a dose dependent increase in fluorescence with PMO-CP8M (FIGS. 10a and 10b). The lack of signal above background does not allow statistical analyses of the comparative increase in fluorescence, but clearly demonstrated that without the CP8M conjugation, PMO did not enter the cell.

Transfection experiments conducted in the HEK293T human embryonic kidney cells again demonstrated that PMO was refractory to cell entry. Importantly, a non-ring closed variant of CP8M (termed CP8M-NC) also did not result in significant cell entry above that of PMO alone. However a ring closed variant that contains the core sequence RKF-S5-RLF-S5 (SEQ ID NO: 57) demonstrated that when conjugated to a fluorescently labelled PMO (to form PMO-C8M), that the PMO was now efficiently taken into cells (FIG. 11). This confirms that the shape imposed upon the peptide sequence, following a ring closing metathesis, is important to facilitate cellular entry of a DCCPM in which the BAC is an ON, more specifically a PMO.

The formal charge of CP8M is +3 at physiological pH. We also provide data demonstrating that reducing the formal charge within this sequence still leads to a surprising and significant cellular entry of CP8M variants with formal charges of +2 (CP8M-2) and +1 (CP8M-1) (FIGS. 12a and 12b), particularly at lower concentrations. The reduction in charge leads to solubility issues which account for the failure of a dose dependent increase, unlike that observed with CP8M. Alternative excipients or manipulations of the peptide as highlighted in Table 5 and Table 6 are likely to overcome these solubility issues.

When transfection experiments were conducted in the H2K mdx mouse myoblasts cells, it confirmed the finding that PMO are refractory to muscle cell entry, which was overcome with the conjugation of CP8M (FIG. 13) and that the CP8M mediated delivery of PMO resulted in the steric blockade of RNA editing of the dystrophin transcript, such that exon 23 was excluded from the transcript (FIG. 14). Again, the lack of exon exclusion from the PMO only samples precludes comparative statistical analyses; but highlights that exon exclusion, resultant from entry of a PMO, only occurs when the PMO is conjugated to CP8M.

In order to determine if CP8M hindered the biological activity of the PMO, direct intramuscular administrations (2.2 nmol) were conducted into the Tibialis anterior muscle of mdx female mice, with muscle recovered 7 days post-administration. The percentage of dystrophin re-expression was equivocal between the PMO-CP8M (805.75) and the naked PMO (762.25) with no statistical significant difference (n=4, p=0.863; FIG. 15 and FIG. 16). Thus it was determined that CP8M does not confer any steric hindrance to the biological activity of the PMO.

Systemic administrations of PMO-CP8M and PMO were conducted in mdx mice to determine if the CP8M moiety enhanced cell entry into skeletal muscle. Varying sub-optimal amounts (totally 1 μmol/kg, 4.4 μmol/kg, 10.9 μmol/kg) were administered by either intraperitoneal or intravenous injections, and diaphragm and/or Tibialis anterior (TA) muscle recovered 7 days post-administration. After a single intraperitoneal administration of 1 μmol/kg the diaphragm muscle gave more dystrophin positive fibres after PMO-CP8M treatment compared to the PMO control group (FIG. 17a, n=1). In tibialis anterior muscles, intravenous (4.4 μmol/kg; n=3) data was equivocal between groups (FIG. 17b and FIG. 17d, p=0.201), as was the intraperitoneal (10.9 μmol/kg; n=4) data (FIG. 17c and FIG. 17d, p=0.886).

(4.4 μmol/kg; n=3) data was equivocal between group (FIG. 17b and FIG. 17d, p=0.201), as was the intraperitoneal (10.9 μmol/kg; n=4) data (FIG. 17c and FIG. 17d, p=0.886).

Systemic intraperitoneal administrations of PMO-CP8M and PMO were conducted in mdx mice to determine if CP8M enhanced cell entry (FIGS. 18-21). A series of tissues was recovered and frozen 1 or 2 weeks post-administration (skeletal muscle, heart, brain and liver).

A single low dose of PMO or PMO-CP8M (1 μmol/kg) was administered (n=1 per group) and tissues recovered 7 days post-administration. Dystrophin-positive heart muscle fibres were detected after PMO-CPM8, but not PMO administration (FIG. 18a).

In addition, we carried out repeated intraperitoneal administrations into mdx mice. Intraperitoneal injections of PMO-CP8M (without fluorescent label) totaling 7.6 μmol/kg over 4 days (n=4 per group) lead to a significant increase in dystrophin-positive heart muscle fibres 2 weeks post-administration compared to injection of an equimolar amount of PMO (340±69 vs 57±17 fibres, p<0.01; FIGS. 18b & 18d).

Furthermore, Applicant carried out intraperitoneal administration of PMO or PMO-CP8M, totaling 10.9 μmol/kg over 2 days (n=4 per group). Again, administration of PMO-CP8M lead to a significantly higher number of dystrophin-positive heart muscle fibres compared to administration of PMO (680±163 vs 33±8 fibres, p<0.05; FIGS. 18c & 18e).

PMO-peptide conjugates of both 8.7 kDa and 9.2 kDa were successfully delivered to heart muscle fibres as evidenced by the induction of dystrophin re-expression in the hearts of mdx mice (FIG. 19, n=4).

A single low dose (1 μmol/kg) intravenous administration of PMO-CP8M, but not PMO (both without fluorescent label), led to recovery of dystrophin expression in the Purkinje cells of mdx mouse cerebellum (FIG. 20; n=1 per group). No dystrophin expression was observed in the PMO control.

A single low dose (1 μmol/kg) intravenous administration of PMO-HP8M led to increased hepatocyte fluorescence in the vicinity of blood vessels two weeks post-administration compared to administration of PMO (FIG. 21; n=1 per group), implying increased uptake of PMO-HP8M in hepatocytes.

CONCLUSION

From the data generated it can be seen that the conjugation of a CPA, stabilized by stapling, to a BAC (in the form of a PMO), via a BFL, facilitates entry of the PMO into a cell. The StaP CPA facilitated PMO entry in both in vitro and in vivo assay systems.

Applicant's data presents evidence that modified linker systems based on HNA and 4 formyl benzioic acid improve the efficiency of conjugation between a BAC and CPA.

Surprisingly, variants of CPA in which the formal charge is reduced demonstrate enhanced cell entry at lower concentrations. This will have important sequelae with respect to improving the toxicological profile of CPA, more specifically a CPP.

The in vivo model of RNA splicing suppression demonstrated that the biological action of an α-helical peptide conjugated PMO is equivalent to naked PMO following intramuscular administration, thus determining that no steric hindrance is exerted upon the PMO when coupled to an α-helical peptide moiety.

The data demonstrates the fact that in the in vivo model of RNA splicing suppression the stabilized CPA may enhance cell entry into skeletal muscle, particularly at lower doses. However PMO are known to enter skeletal muscle without a CPP conjugation.

Surprisingly, and very significantly, it has been demonstrated that tissues refractory to naked PMO transfection re-express dystrophin protein in both the heart and brain (purkinje cell) compartments when the PMO is conjugated with a StaP.

Applicant further provides evidence that the CPP can facilitate the entry of cargoes of different size and mass far beyond that stated in the current state of the art.

The repertoire of human and animal diseases that can be addressed is now expanded and enhanced due to the increased pharmacodynamics of the PMOs when conjugated with a stabilised peptide. Neuromuscular disease, metabolic disease, cancer, age-related degenerative diseases and acquired viral infection can all be targeted.

REFERENCES

1 Iversen, P. L. et al. Discovery and early development of AVI-7537 and AVI-7288 for the treatment of Ebola virus and Marburg virus infections. *Viruses* 4, 2806-2830, doi: 10.3390/v4112806 (2012).

2 Heald, A. E. et al. Safety and pharmacokinetic profiles of phosphorodiamidate morpholino oligomers with activity against ebola virus and marburg virus: results of two single-ascending-dose studies. *Antimicrob Agents Chemother* 58, 6639-6647, doi:10.1128/aac.03442-14 (2014).

3 Warren, T. K. et al. Advanced antisense therapies for postexposure protection against lethal filovirus infections. *Nat Med* 16, 991-994, doi:10.1038/nm.2202 (2010).

4. Campbell, J. M., Bacon, T. A. & Wickstrom, E. Oligodeoxynucleoside phosphorothioate stability in subcellular extracts, culture media, sera and cerebrospinal fluid. *Journal of biochemical and biophysical methods* 20, 259-267 (1990).

5. Agrawal, S., Mayrand, S. H., Zamecnik, P. C. & Pederson, T. Site-specific excision from RNA by RNase H and mixed-phosphate-backbone oligodeoxynucleotides. *Proc Natl Acad Sci USA* 87, 1401-1405 (1990).

6. Tereshko, V. et al. Correlating structure and stability of DNA duplexes with incorporated 2'-O-modified RNA analogues. *Biochemistry* 37, 10626-10634, doi:10.1021/bi980392a (1998).

7. Shibahara, S. et al. Inhibition of human immunodeficiency virus (HIV-1) replication by synthetic oligo-RNA derivatives. *Nucleic Acids Res* 17, 239-252 (1989).

8. Goemans N, C. C., Kraus J E, et al. Drisapersen efficacy and safety in Duchenne muscular dystrophy: results of a phase III, randomized, double-blind, placebo-controlled trial (study DMD114044). *World Muscle Society Congress; Asilomar, Calif., USA*; Oct. 1-5, 2013 (2103).

9. Goemans, N. M. et al. Long-Term Efficacy, Safety, and Pharmacokinetics of Drisapersen in Duchenne Muscular Dystrophy: Results from an Open-Label Extension Study. *PLoS One* 11, e0161955, doi:10.1371/journal.pone.0161955 (2016).

10. Dirin, M. & Winkler, J. Influence of diverse chemical modifications on the ADME characteristics and toxicology of antisense oligonucleotides. *Expert Opin Biol Ther* 13, 875-888, doi:10.1517/14712598.2013.774366 (2013).

11. Sazani, P. et al. Repeat-dose toxicology evaluation in cynomolgus monkeys of AVI-4658, a phosphorodiamidate morpholino oligomer (PMO) drug for the treatment of duchenne muscular dystrophy. *Int J Toxicol* 30, 313-321, doi:10.1177/1091581811403505 (2011).

12. Sazani, P., Weller, D. L. & Shrewsbury, S. B. Safety pharmacology and genotoxicity evaluation of AVI-4658. *Int J Toxicol* 29, 143-156, doi:10.1177/1091581809359206 (2010).

13. Mendell, J. R. et al. Eteplirsen for the treatment of Duchenne muscular dystrophy. *Ann Neurol* 74, 637-647, doi:10.1002/ana.23982 (2013).

14. Heemskerk, H. A. et al. In vivo comparison of 2'-O-methyl phosphorothioate and morpholino antisense oligonucleotides for Duchenne muscular dystrophy exon skipping. *J Gene Med* 11, 257-266, doi:10.1002/jgm.1288 [doi] (2009).

15. Kreutz, M. et al. Antibody-antigen-adjuvant conjugates enable co-delivery of antigen and adjuvant to dendritic cells in cis but only have partial targeting specificity. *PLoS One* 7, e40208, doi:10.1371/journal.pone.0040208 (2012).

16. Derossi, D., Joliot, A. H., Chassaing, G. & Prochiantz, A. The third helix of the Antennapedia homeodomain translocates through biological membranes. *J Biol Chem* 269, 10444-10450 (1994).

17. Gautam, A. et al. CPPsite: a curated database of cell penetrating peptides. *Database the journal of biological databases and curation* 2012, bas015, doi:10.1093/database/bas015 (2012).

18. Hirose, H. et al. Transient focal membrane deformation induced by arginine-rich peptides leads to their direct penetration into cells. *Mol Ther* 20, 984-993, doi:10.1038/mt.2011.313 (2012).

19. Moulton, H. M. & Moulton, J. D. Morpholinos and their peptide conjugates: therapeutic promise and challenge for Duchenne muscular dystrophy. *Biochim Biophys Acta* 1798, 2296-2303, doi:10.1016/j.bbamem.2010.02.012 (2010).

20. Tunnemann, G. et al. Live-cell analysis of cell penetration ability and toxicity of oligo-arginines. *J Pept Sci* 14, 469-476, doi:10.1002/psc.968 (2008).

21. Chu, Q. et al. Towards understanding cell penetration by stapled peptides. *Med Chem Comm* 6, 111-119, doi:10.1039/C4MD00131A (2015).

22. Hilinski, G. J. et al. Stitched α-Helical Peptides via Bis Ring-Closing Metathesis. *Journal of the American Chemical Society* 136, 12314-12322, doi:10.1021/ja505141j (2014).

23. Lehto, T. et al. Cellular trafficking determines the exon skipping activity of Pip6a-PMO in mdx skeletal and cardiac muscle cells. *Nucleic Acids Res* 42, 3207-3217, doi:10.1093/nar/gkt1220 (2014).

24. Nakase, I. et al. Interaction of arginine-rich peptides with membrane-associated proteoglycans is crucial for induction of actin organization and macropinocytosis. *Biochemistry* 46, 492-501, doi:10.1021/bi0612824 (2007).

25. Chang, Y. S. et al. Stapled alpha-helical peptide drug development: a potent dual inhibitor of MDM2 and MDMX for p53-dependent cancer therapy. *Proc Natl Acad Sci USA* 110, E3445-3454, doi:10.1073/pnas.1303002110 (2013).

26. Vitiello, L. et al. In vivo delivery of naked antisense oligos in aged mdx mice: analysis of dystrophin restoration in skeletal and cardiac muscle. *Neuromuscul Disord* 18, 597-605, doi:50960-8966(08)00141-7 [pii]10.1016/j.nmd.2008.05.011 [doi] (2008).

27. Jearawiriyapaisarn, N., Moulton, H. M., Sazani, P., Kole, R. & Willis, M. S. Long-term improvement in mdx cardiomyopathy after therapy with peptide-conjugated morpholino oligomers. *Cardiovasc Res* 85, 444-453, doi: cvp335 [pii]10.1093/cvr/cvp335 [doi] (2010).

28. Wu, B. et al. One-year treatment of morpholino antisense oligomer improves skeletal and cardiac muscle functions in dystrophic mdx mice. *Mol Ther* 19, 576-583, doi: 10.1038/mt.2010.288 (2011).

29. Wu, B. et al. Effective rescue of dystrophin improves cardiac function in dystrophin-deficient mice by a modified morpholino oligomer. *Proc Natl Acad Sci USA* 105, 14814-14819, doi:0805676105 [pii]10.1073/pnas.0805676105 [doi] (2008).

30. Jearawiriyapaisarn, N. et al. Sustained dystrophin expression induced by peptide-conjugated morpholino oligomers in the muscles of mdx mice. *Mol Ther* 16, 1624-1629, doi:mt2008120 [pii]10.1038/mt.2008.120 [doi] (2008).

31. Betts, C. et al. Pip6-PMO, A New Generation of Peptide-oligonucleotide Conjugates With Improved Cardiac Exon Skipping Activity for DMD Treatment. *Molecular therapy. Nucleic acids* 1, e38, doi:10.1038/mtna.2012.30 (2012).

32. Ivanova, G. D. et al. Improved cell-penetrating peptide-PNA conjugates for splicing redirection in HeLa cells and exon skipping in mdx mouse muscle. *Nucleic Acids Res* 36, 6418-6428 (2008).

33. Mendell, J. R. et al. Evidence-based path to newborn screening for Duchenne muscular dystrophy. *Ann Neurol* 71, 304-313, doi:10.1002/ana.23528 (2012).

34. Hoffman, E. P., Brown, R. H., Jr. & Kunkel, L. M. Dystrophin: the protein product of the Duchenne muscular dystrophy locus. *Cell* 51, 919-928. (1987).

35. Monaco, A. P., Bertelson, C. J., Liechti-Gallati, S., Moser, H. & Kunkel, L. M. An explanation for the phenotypic differences between patients bearing partial deletions of the DMD locus. *Genomics* 2, 90-95 (1988).

36 Aartsma-Rus, A. et al. Therapeutic antisense-induced exon skipping in cultured muscle cells from six different DMD patients. *Hum Mol Genet* 12, 907-914 (2003).
37 Alter, J. et al. Systemic delivery of morpholino oligonucleotide restores dystrophin expression bodywide and improves dystrophic pathology. *Nat Med* 12, 175-177 (2006).
38 Kinali, M. et al. Local restoration of dystrophin expression with the morpholino oligomer AVI-4658 in Duchenne muscular dystrophy: a single-blind, placebo-controlled, dose-escalation, proof-of-concept study. *Lancet Neurol* 8, 918-928, doi:S1474-4422(09)70211-X [pii] 10.1016/S1474-4422(09)70211-X [doi] (2009).
39 Lu, Q. L. et al. Systemic delivery of antisense oligoribonucleotide restores dystrophin expression in body-wide skeletal muscles. *Proc Natl Acad Sci USA* 102, 198-203 (2005).
40 van Deutekom, J. C. et al. *Local dystrophin restoration with antisense oligonucleotide* PRO051. *N Engl J Med* 357, 2677-2686, doi:357/26/2677 [pii]10.1056/NEJMoa073108 [doi] (2007).
41 Wu, B. et al. Dose-dependent restoration of dystrophin expression in cardiac muscle of dystrophic mice by systemically delivered morpholino. *Gene Ther* 17, 132-140, doi:gt2009120 [pii]10.1038/gt.2009.120 [doi] (2010).
42 Cirak, S. et al. Exon skipping and dystrophin restoration in patients with Duchenne muscular dystrophy after systemic phosphorodiamidate morpholino oligomer treatment: an open-label, phase 2, dose-escalation study. *Lancet* 378, 595-605, doi:10.1016/s0140-6736(11)60756-3 (2011).

---

The invention claimed is:

1. A method of delivering a biologically active siRNA or antisense oligonucleotide moiety into a cell and retaining biological activity of the siRNA or antisense oligonucleotide moiety, comprising the step of contacting the cell with a molecule, the molecule comprising:
   i) a biologically active siRNA or antisense oligonucleotide moiety, comprising a phosphorodiamidate morpholino oligonucleotide (PMO) covalently linked via a bi-functional linker moiety (BFL) to,
   ii) a peptide moiety comprising a stapled peptide (StaP) or a stitched peptide (StiP), wherein the StaP or StiP is a stabilized peptide which has a conformation comprising at least one alpha helix by olefin cross linking comprising in the StaP an olefin cross link between two unnatural amino acids of the peptide at positions i, i+4, and/or i, i+7 and in the StiP at least two olefin cross links between at least three unnatural amino acids of the peptide at positions i, i+4, and i+11, and the StaP or the StiP can penetrate a cell membrane,
   wherein the StaP or StiP has the amino acid sequence comprising SEQ ID NO: 27, 28, 33, 41, 44, 57, 88, 89, 90, 91, 92, 93, 94, 109, 140, 141, 159, 160, 162, 163, 164, or 165,
   wherein the molecule can penetrate a cell membrane, and has biological activity of the siRNA or antisense oligonucleotide moiety.

2. The method according to claim 1, wherein the StaP or StiP comprises at least two unnatural amino acids bearing all-hydrocarbon tethers and at least one of those unnatural amino acids has an α-methyl group.

3. The method according to claim 1, wherein each cross link is formed by ring-closing olefin metathesis.

4. The method according to claim 1, wherein each cross link comprises a hydrocarbon bridge, and wherein at least one cross linked unnatural amino acid comprises an α-methyl group.

5. The method according to claim 1, wherein the StaP or StiP comprises at least two unnatural amino acids bearing all-hydrocarbon tethers.

6. The method of claim 5, wherein the StaP or StiP is stabilized by at least one cross link between the unnatural amino acid R-octenylalanine and the unnatural amino acid S-pentenylalanine.

7. The method according to claim 3, wherein the StaP or StiP is stabilized by at least one cross link between one or more of the unnatural amino acids: (S)-pentenylalanine (S5) or its enantiomer (R5); S-octenylalanine (S8) or its enantiomer (R8); or combinations thereof.

8. The method according to claim 1, wherein the StaP or StiP is stabilized by at least one cross link between one or more of the unnatural amino acids:

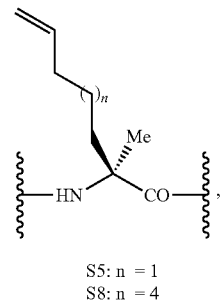

S5: n = 1
S8: n = 4

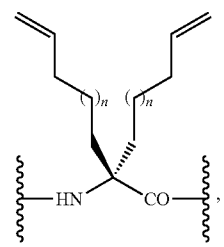

B5: n = 1
B8: n = 4

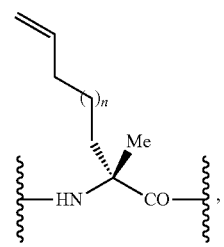

R5: n = 1
R8: n = 4

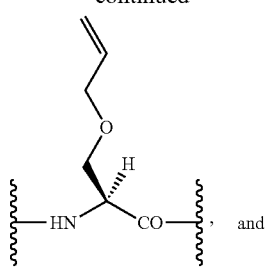

S-OAS

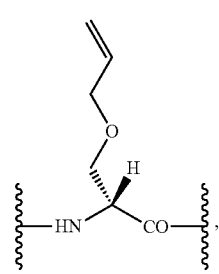

R-OAS wherein S5 is (S)-pentenylalanine, R5 is (R)-pentenylalanine, S8 is (S)-octenylalanine, R8 is (R)-octenylalanine, B5 is α, α-di-substituted pentenylalanine, B8 is α, α-di-substituted octenylalanine, and S-OAS and R-OAS are O-allyl-serine analogues.

9. The method according to claim 5, wherein the StaP or StiP is stabilized by at least one cross link the unnatural amino acid R-octenylalanine and the unnatural amino acid R-pentenylalanine.

10. The method according to claim 1, wherein the stabilized conformation comprises at least one beta sheet.

11. The method of claim 1, wherein the BFL comprises:

(SMCC)

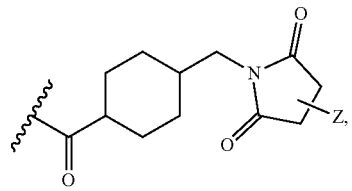

a residue of succinimidyl 4-(N-maleimidomethyl) cyclohexane-1-carboxylate, where Z is

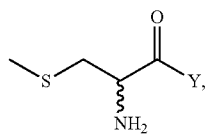

and Y is a covalent bond to the N-terminus of the StaP or the StiP, or Y is

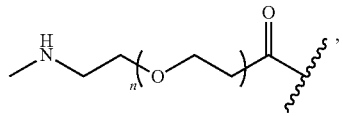

where n is 1 to 10;

(AMAS)

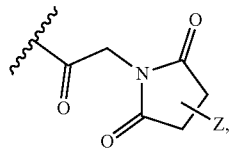

a residue of N-α-maleimidoacet-oxysuccinimide ester, where Z is

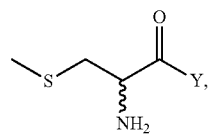

and Y is a covalent bond to the N-terminus of the StaP or the StiP, or Y is

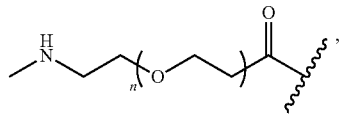

where n is 1 to 10;

(BMPS)

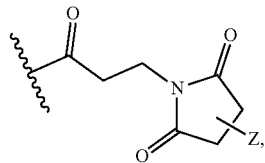

a residue of N-β-maleimidopropyl-oxysuccinimide ester, where Z is

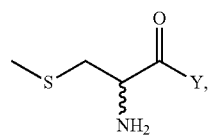

and Y is a covalent bond to the N-terminus of the StaP or the StiP, or Y is

127

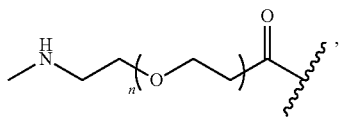

where n is 1 to 10;

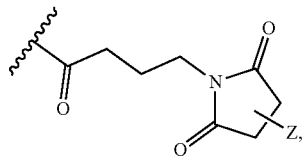

(GMBS)

a residue of N-γ-aleimidobutyryl-oxysuccinimide ester, where Z is

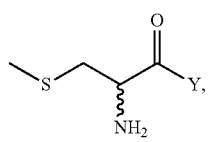

and Y is a covalent bond to the N-terminus of the StaP or the StiP, or Y is

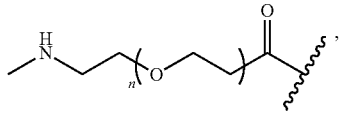

where n is 1 to 10;

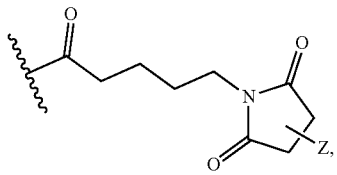

(DMVS)

a residue of N-δ-maleimidovaleryl-oxysuccinimide ester, where Z is

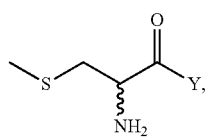

and Y is a covalent bond to the N-terminus of the StaP or the StiP, or Y is

128

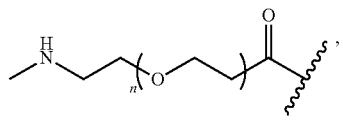

where n is 1 to 10;

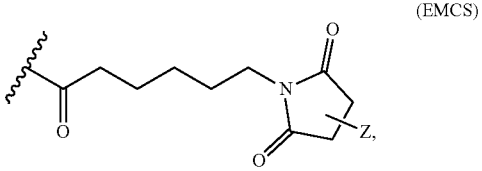

(EMCS)

a residue of N-ε-malemidocaproyl-oxysuccinimide ester, where Z is

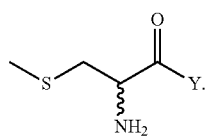

and Y is a covalent bond to the N-terminus of the StaP or the StiP, or Y is

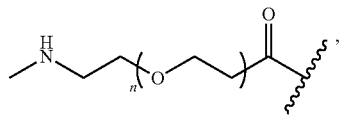

where n is 1 to 10

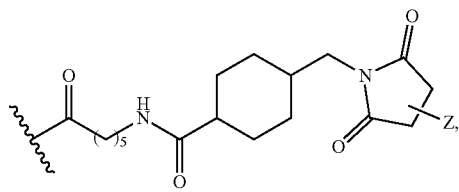

(LC-SMCC)

a residue of succinimidyl 4-(N-maleimidomethyl) cyclohexane-1-carboxy-(6-amidocaproate), where Z is

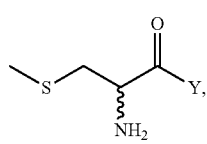

and Y is a covalent bond to the N-terminus of the StaP or the StiP, or Y is

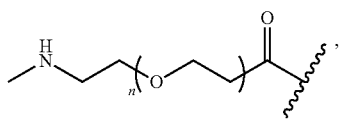

where n is 1 to 10;

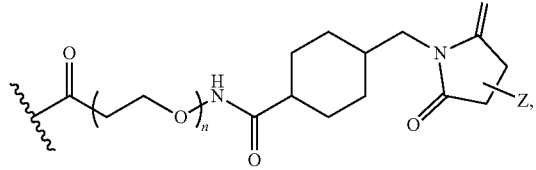
(SM(PEG)ₙ)

a residue of succinimidyl 4-(N-maleimidomethyl) cyclohexane-1-carboxylate (polyethylene glycol)ₙ, wherein n equals 1 to 10, Z is

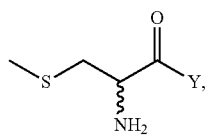

and, Y is either present or not present, and when Y is present, Y is

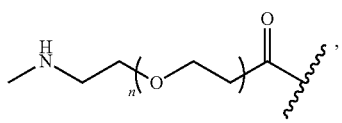

where n is 1 to 10, and when Y is not present, Y is a covalent bond to the N-terminus of the StaP or the StiP;

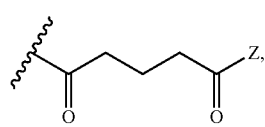
(DGS)

a residue of disuccinimidyl gluterate, where Z is not present, and instead there is a covalent bond to the N-terminus of the StaP or the StiP, or to the N of

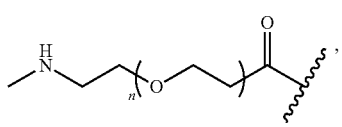

wherein n is 1 to 10;
or,

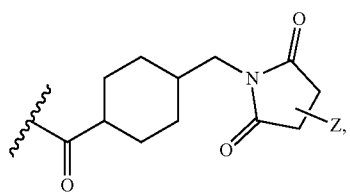
(DSCDS)

a residue of disuccinimidyl-cyclohexl-1,4-diester, where Z is not present, and instead there is a covalent bond to the N-terminus of the StaP or the StiP, or to the N of

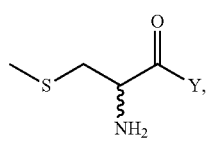

wherein n is 1 to 10.

12. The method of claim 11, wherein in each Y moiety, n is 5.

13. The method of claim 11, wherein the BFL comprises SMCC.

14. The method of claim 1, wherein the BFL comprises:

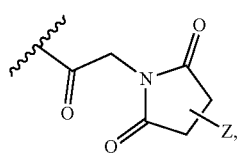

a residue of succinimidyl 4-(N-maleimidomethyl) cyclohexane-1-carboxylate, where Z is

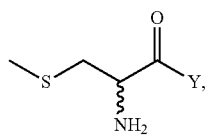

and Y is a covalent bond to the N-terminus of the StaP or the StiP;

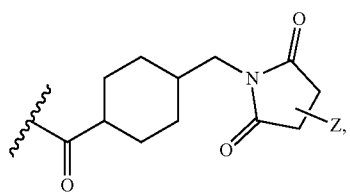

a residue of N-α-maleimidoacet-oxysuccinimide ester, where Z is

131

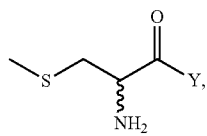

and Y is a covalent bond to the N-terminus of the StaP or the StiP;

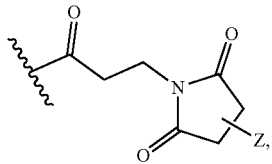

a residue of N-β-maleimidopropyl-oxysuccinimide ester, where Z is

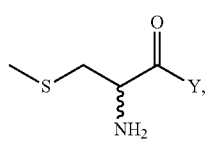

and Y is a covalent bond to the N-terminus of the StaP or the StiP;

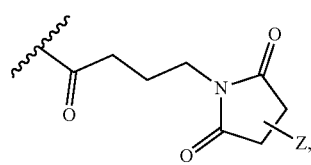

a residue of N-γ-aleimidobutyryl-oxysuccinimide ester, where Z is

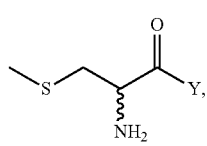

and Y is a covalent bond to the N-terminus of the StaP or the StiP;

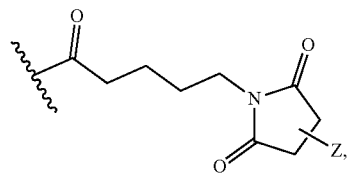

a residue of N-δ-maleimidovaleryl-oxysuccinimide ester, where Z is

132

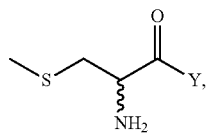

and Y is a covalent bond to the N-terminus of the StaP or the StiP;

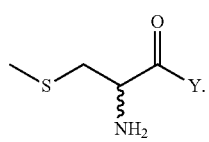

a residue of N-ε-malemidocaproyl-oxysuccinimide ester, where Z is

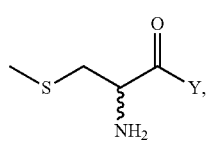

and Y is a covalent bond to the N-terminus of the StaP or the StiP;

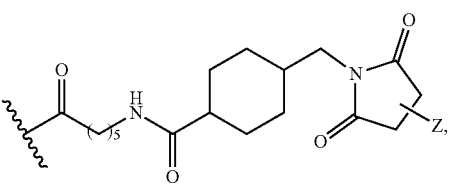

a residue of succinimidyl 4-(N-maleimidomethyl) cyclohexane-1-carboxy-(6-amidocaproate),
where Z is

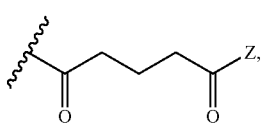

and Y is a covalent bond to the N-terminus of the StaP or the StiP;

a residue of disuccinimidyl gluterate, where Z is not present; or, a residue of disuccinimidyl-cyclohexl-1,4-diester, where Z is not present.

15. The method of claim 12, wherein the BFL comprises SMCC.

16. The method of claim 1, wherein the oligonucleotide comprises (SEQ ID NO: 2)
5'CUCCAACAUCAAGGAAGAUGGCAUUUCUAG3'.

17. The method of claim 1, wherein the StiP or StaP comprises pentenylalanine.

18. The method according to claim 1, wherein the BFL comprises a residue of an amine to sulphydryl cross linker containing N-hydroxysuccinimide esters and malemide reactive groups separated by a cyclohexane spacer.

19. The method according to claim 18, wherein the BFL comprises a residue of succinimidyl 4-(N-maleimidomethyl) cyclohexane-1-carboxylate (SMCC).

20. The method of claim 1, wherein the StiP or the StaP has a formal charge between +3 and +1.

21. The method of claim 1, wherein contacting the cell occurs at a concentration between 1.0 μM and 10 μM of the molecule.

22. The method of claim 1, wherein the peptide moiety is a StaP, wherein the StaP has the amino acid sequence of SEQ ID NO: 57.

23. A method making a molecule comprising the step of conjugating:
  i) a biologically active siRNA or antisense oligonucleotide moiety, comprising a phosphordiamidate morpholino oligonucleotide to,
  ii) a peptide moiety comprising a stapled peptide (StaP) or a stitched peptide (StiP), wherein the StaP or StiP is a stabilized peptide which has a conformation comprising at least one alpha helix by olefin cross linking comprising in the StaP an olefin cross link between two unnatural amino acids of the peptide at positions i, i+4, and/or i, i+7 and in the StiP at least two olefin cross links between at least three unnatural amino acids of the peptide at positions i, i+4, and i+11, and the StaP or the StiP can penetrate a cell membrane,
  wherein the StaP or StiP has the amino acid sequence comprising SEQ ID NO: 27, 28, 33, 41, 44, 57, 88, 89, 90, 91, 92, 93, 94, 109, 140, 141, 159, 160, 162, 163, 164, or 165,
  wherein the biologically active siRNA or antisense oligonucleotide moiety is covalently linked directly to the StiP or the StaP via a bi-functional linker moiety (BFL) to the StiP or the StaP,
  wherein the molecule can penetrate a cell membrane, and has biological activity of the siRNA or antisense oligonucleotide moiety.

24. The method of claim 23, wherein the phosphorodoamidate morpholino oligonucleotide has the sequence of (SEQ ID NO: 2)
5'CUCCAACAUCAAGGAAGAUGGCAUUUCUAG3'.

25. The method of claim 23, wherein the BFL is SMCC.

26. The method of claim 23, wherein the peptide moiety is a StaP, wherein the StaP has the amino acid sequence of SEQ ID NO: 57.

* * * * *

SEQUENCE LISTING

```
Sequence total quantity: 194
SEQ ID NO: 1            moltype = DNA  length = 25
FEATURE                 Location/Qualifiers
source                  1..25
                        mol_type = other DNA
                        organism = Homo sapiens
SEQUENCE: 1
ggccaaacct cggcttacct gaaat                                             25

SEQ ID NO: 2            moltype = RNA  length = 30
FEATURE                 Location/Qualifiers
source                  1..30
                        mol_type = other RNA
                        organism = Homo sapiens
SEQUENCE: 2
ctccaacatc aaggaagatg gcatttctag                                        30

SEQ ID NO: 3            moltype = AA   length = 18
FEATURE                 Location/Qualifiers
REGION                  1..18
                        note = Synthetic
source                  1..18
                        mol_type = protein
                        organism = synthetic construct
SEQUENCE: 3
TRQARRNRRR RWRRAAAA                                                     18

SEQ ID NO: 4            moltype = AA   length = 17
FEATURE                 Location/Qualifiers
REGION                  1..17
                        note = Synthetic
source                  1..17
                        mol_type = protein
                        organism = synthetic construct
SEQUENCE: 4
TRQARRNRRR RWRERQR                                                      17

SEQ ID NO: 5            moltype = AA   length = 16
FEATURE                 Location/Qualifiers
REGION                  1..16
                        note = Synthetic
source                  1..16
                        mol_type = protein
                        organism = synthetic construct
SEQUENCE: 5
RQIKIWFQNR RMKWKK                                                       16

SEQ ID NO: 6            moltype = AA   length = 12
FEATURE                 Location/Qualifiers
REGION                  1..12
                        note = Synthetic
source                  1..12
                        mol_type = protein
                        organism = synthetic construct
SEQUENCE: 6
RRRRRRRRWR RR                                                           12
```

```
SEQ ID NO: 7            moltype = AA   length = 16
FEATURE                 Location/Qualifiers
REGION                  1..16
                        note = Synthetic
source                  1..16
                        mol_type = protein
                        organism = synthetic construct
SEQUENCE: 7
LSQETFSDLW KLLPEN                                                       16

SEQ ID NO: 8            moltype = AA   length = 14
FEATURE                 Location/Qualifiers
REGION                  1..14
                        note = Synthetic
source                  1..14
                        mol_type = protein
                        organism = synthetic construct
SEQUENCE: 8
NQLKRSFFAL RDQI                                                         14

SEQ ID NO: 9            moltype = AA   length = 23
FEATURE                 Location/Qualifiers
REGION                  1..23
                        note = Synthetic
source                  1..23
                        mol_type = protein
                        organism = synthetic construct
SEQUENCE: 9
TILKASVDYI RKLQREQQRA KEL                                               23

SEQ ID NO: 10           moltype = AA   length = 12
FEATURE                 Location/Qualifiers
REGION                  1..12
                        note = Synthetic
source                  1..12
                        mol_type = protein
                        organism = synthetic construct
SEQUENCE: 10
RRRRRRRRRR RR                                                           12

SEQ ID NO: 11           moltype = AA   length = 12
FEATURE                 Location/Qualifiers
REGION                  1..12
                        note = Synthetic
source                  1..12
                        mol_type = protein
                        organism = synthetic construct
SEQUENCE: 11
YGRKKRRQRR RP                                                           12

SEQ ID NO: 12           moltype = AA   length = 8
FEATURE                 Location/Qualifiers
REGION                  1..8
                        note = Synthetic
source                  1..8
                        mol_type = protein
                        organism = synthetic construct
SEQUENCE: 12
RKFKRLFQ                                                                8

SEQ ID NO: 13           moltype = AA   length = 14
FEATURE                 Location/Qualifiers
REGION                  1..14
                        note = Synthetic
source                  1..14
                        mol_type = protein
                        organism = synthetic construct
SEQUENCE: 13
NELKRSFFAL RDQI                                                         14

SEQ ID NO: 14           moltype = AA   length = 14
FEATURE                 Location/Qualifiers
REGION                  1..14
                        note = Synthetic
SITE                    4
                        note = misc_feature - Xaa is R8, an enantiomer of S8,
                         S-octenylalanine
SITE                    11
```

-continued

| | |
|---|---|
| | note = misc_feature - Xaa is S5, a-methyl, a-alkenylglycine with 5 carbon chain |
| source | 1..14<br>mol_type = protein<br>organism = synthetic construct |

SEQUENCE: 14
NQLXRSFFAL XDQI                                                              14

| | |
|---|---|
| SEQ ID NO: 15 | moltype = AA  length = 9 |
| FEATURE | Location/Qualifiers |
| REGION | 1..9<br>note = Synthetic |
| source | 1..9<br>mol_type = protein<br>organism = synthetic construct |

SEQUENCE: 15
KNHTHQQDI                                                                     9

| | |
|---|---|
| SEQ ID NO: 16 | moltype = AA  length = 42 |
| FEATURE | Location/Qualifiers |
| REGION | 1..42<br>note = Synthetic |
| source | 1..42<br>mol_type = protein<br>organism = synthetic construct |

SEQUENCE: 16
NELKRSFFAL RDQIPSLQGE KASRAQILDK ATEYIQYNLR RK                                42

| | |
|---|---|
| SEQ ID NO: 17 | moltype = AA  length = 24 |
| FEATURE | Location/Qualifiers |
| REGION | 1..24<br>note = Synthetic |
| source | 1..24<br>mol_type = protein<br>organism = synthetic construct |

SEQUENCE: 17
KATEYIQYNL RRKNHTHQQD IDDL                                                   24

| | |
|---|---|
| SEQ ID NO: 18 | moltype = AA  length = 15 |
| FEATURE | Location/Qualifiers |
| REGION | 1..15<br>note = Synthetic |
| source | 1..15<br>mol_type = protein<br>organism = synthetic construct |

SEQUENCE: 18
ASTLFETFYL GGLLG                                                             15

| | |
|---|---|
| SEQ ID NO: 19 | moltype = AA  length = 15 |
| FEATURE | Location/Qualifiers |
| REGION | 1..15<br>note = Synthetic |
| SITE | 10<br>note = misc_feature - Xaa is S5, a-methyl, a-alkenylglycine with 5 carbon chain |
| SITE | 14<br>note = misc_feature - Xaa is S5, a-methyl, a-alkenylglycine with 5 carbon chain |
| source | 1..15<br>mol_type = protein<br>organism = synthetic construct |

SEQUENCE: 19
RRGSRPSGAX RRRXR                                                             15

| | |
|---|---|
| SEQ ID NO: 20 | moltype = AA  length = 14 |
| FEATURE | Location/Qualifiers |
| REGION | 1..14<br>note = Synthetic |
| source | 1..14<br>mol_type = protein<br>organism = synthetic construct |

SEQUENCE: 20
FNINDRIKEL GTLI                                                              14

| | |
|---|---|
| SEQ ID NO: 21 | moltype = AA  length = 42 |
| FEATURE | Location/Qualifiers |
| REGION | 1..42<br>note = Synthetic |
| source | 1..42 |

```
                            mol_type = protein
                            organism = synthetic construct
SEQUENCE: 21
DHIKDSFHSL RDSVPSLQGE KASRAQILDK ATEYIQYNLR RK                        42

SEQ ID NO: 22               moltype = AA   length = 36
FEATURE                     Location/Qualifiers
REGION                      1..36
                            note = Synthetic
source                      1..36
                            mol_type = protein
                            organism = synthetic construct
SEQUENCE: 22
EYIQYNLRKN HTHQQDIDDL KRQNALLEQQ VRALGG                               36

SEQ ID NO: 23               moltype = AA   length = 16
FEATURE                     Location/Qualifiers
REGION                      1..16
                            note = Synthetic
source                      1..16
                            mol_type = protein
                            organism = synthetic construct
SEQUENCE: 23
SSLFERFYNL VTPAGG                                                     16

SEQ ID NO: 24               moltype = AA   length = 16
FEATURE                     Location/Qualifiers
REGION                      1..16
                            note = Synthetic
source                      1..16
                            mol_type = protein
                            organism = synthetic construct
SEQUENCE: 24
NSSFADFFHT VPYNLL                                                     16

SEQ ID NO: 25               moltype = AA   length = 14
FEATURE                     Location/Qualifiers
REGION                      1..14
                            note = Synthetic
SITE                        8
                            note = misc_feature - Xaa is S5, a-methyl, a-alkenylglycine
                             with 5 carbon chain
SITE                        12
                            note = misc_feature - Xaa is S5, a-methyl, a-alkenylglycine
                             with 5 carbon chain
source                      1..14
                            mol_type = protein
                            organism = synthetic construct
SEQUENCE: 25
TRQARRNXRR RXRR                                                       14

SEQ ID NO: 26               moltype = AA   length = 19
FEATURE                     Location/Qualifiers
REGION                      1..19
                            note = Synthetic
SITE                        10
                            note = misc_feature - Xaa is S5, a-methyl, a-alkenylglycine
                             with 5 carbon chain
SITE                        14
                            note = misc_feature - Xaa is S5, a-methyl, a-alkenylglycine
                             with 5 carbon chain
source                      1..19
                            mol_type = protein
                            organism = synthetic construct
SEQUENCE: 26
RRGSRPSGAX RRRXRAAAA                                                  19

SEQ ID NO: 27               moltype = AA   length = 15
FEATURE                     Location/Qualifiers
REGION                      1..15
                            note = Synthetic
SITE                        1
                            note = misc_feature - Xaa is S5, a-methyl, a-alkenylglycine
                             with 5 carbon chain
SITE                        5
                            note = misc_feature - Xaa is S5, a-methyl, a-alkenylglycine
                             with 5 carbon chain
source                      1..15
                            mol_type = protein
```

```
                          organism = synthetic construct
SEQUENCE: 27
XRRQXRRDRQ RRRRR                                                            15

SEQ ID NO: 28             moltype = AA   length = 17
FEATURE                   Location/Qualifiers
REGION                    1..17
                          note = Synthetic
SITE                      4
                          note = misc_feature - Xaa is S5, a-methyl, a-alkenylglycine
                            with 5 carbon chain
SITE                      8
                          note = misc_feature - Xaa is S5, a-methyl, a-alkenylglycine
                            with 5 carbon chain
source                    1..17
                          mol_type = protein
                          organism = synthetic construct
SEQUENCE: 28
TRQXRRQXRR RWRERQR                                                          17

SEQ ID NO: 29             moltype = AA   length = 26
FEATURE                   Location/Qualifiers
REGION                    1..26
                          note = Synthetic
SITE                      6
                          note = misc_feature - Xaa is S5, a-methyl, a-alkenylglycine
                            with 5 carbon chain
SITE                      10
                          note = misc_feature - Xaa is S5, a-methyl, a-alkenylglycine
                            with 5 carbon chain
source                    1..26
                          mol_type = protein
                          organism = synthetic construct
SEQUENCE: 29
SEELVXEAHX LCTLLENAIQ DTVREQ                                                26

SEQ ID NO: 30             moltype = AA   length = 26
FEATURE                   Location/Qualifiers
REGION                    1..26
                          note = Synthetic
SITE                      10
                          note = misc_feature - Xaa is S5, a-methyl, a-alkenylglycine
                            with 5 carbon chain
SITE                      14
                          note = misc_feature - Xaa is S5, a-methyl, a-alkenylglycine
                            with 5 carbon chain
source                    1..26
                          mol_type = protein
                          organism = synthetic construct
SEQUENCE: 30
SEELVAEAHX LCTXLENAIQ DTVREQ                                                26

SEQ ID NO: 31             moltype = AA   length = 26
FEATURE                   Location/Qualifiers
REGION                    1..26
                          note = Synthetic
SITE                      17
                          note = misc_feature - Xaa is S5, a-methyl, a-alkenylglycine
                            with 5 carbon chain
SITE                      21
                          note = misc_feature - Xaa is S5, a-methyl, a-alkenylglycine
                            with 5 carbon chain
source                    1..26
                          mol_type = protein
                          organism = synthetic construct
SEQUENCE: 31
SEELVAEAHN LCTLLEXAIQ XTVREQ                                                26

SEQ ID NO: 32             moltype = AA   length = 15
FEATURE                   Location/Qualifiers
REGION                    1..15
                          note = Synthetic
SITE                      8
                          note = misc_feature - Xaa is S5, a-methyl, a-alkenylglycine
                            with 5 carbon chain
SITE                      12
                          note = misc_feature - Xaa is S5, a-methyl, a-alkenylglycine
                            with 5 carbon chain
source                    1..15
```

```
                        mol_type = protein
                        organism = synthetic construct
SEQUENCE: 32
DRRQRRRXRQ RXRRR                                                      15

SEQ ID NO: 33           moltype = AA  length = 15
FEATURE                 Location/Qualifiers
REGION                  1..15
                        note = Synthetic
SITE                    1
                        note = misc_feature - Xaa is S5, a-methyl, a-alkenylglycine
                          with 5 carbon chain
SITE                    5
                        note = misc_feature - Xaa is S5, a-methyl, a-alkenylglycine
                          with 5 carbon chain
source                  1..15
                        mol_type = protein
                        organism = synthetic construct
SEQUENCE: 33
XRRQXRRRRQ RRRRR                                                      15

SEQ ID NO: 34           moltype = AA  length = 26
FEATURE                 Location/Qualifiers
REGION                  1..26
                        note = Synthetic
SITE                    2
                        note = misc_feature - Xaa is S5, a-methyl, a-alkenylglycine
                          with 5 carbon chain
SITE                    6
                        note = misc_feature - Xaa is S5, a-methyl, a-alkenylglycine
                          with 5 carbon chain
source                  1..26
                        mol_type = protein
                        organism = synthetic construct
SEQUENCE: 34
SXELVXEAHN LCTLLENAIQ DTVREQ                                          26

SEQ ID NO: 35           moltype = AA  length = 26
FEATURE                 Location/Qualifiers
REGION                  1..26
                        note = Synthetic
SITE                    9
                        note = misc_feature - Xaa is S5, a-methyl, a-alkenylglycine
                          with 5 carbon chain
SITE                    13
                        note = misc_feature - Xaa is S5, a-methyl, a-alkenylglycine
                          with 5 carbon chain
source                  1..26
                        mol_type = protein
                        organism = synthetic construct
SEQUENCE: 35
SEELVAEAXN LCXLLENAIQ DTVREQ                                          26

SEQ ID NO: 36           moltype = AA  length = 26
FEATURE                 Location/Qualifiers
REGION                  1..26
                        note = Synthetic
SITE                    13
                        note = misc_feature - Xaa is S5, a-methyl, a-alkenylglycine
                          with 5 carbon chain
SITE                    17
                        note = misc_feature - Xaa is S5, a-methyl, a-alkenylglycine
                          with 5 carbon chain
source                  1..26
                        mol_type = protein
                        organism = synthetic construct
SEQUENCE: 36
SEELVAEAHN LCXLLEXAIQ DTVREQ                                          26

SEQ ID NO: 37           moltype = AA  length = 26
FEATURE                 Location/Qualifiers
REGION                  1..26
                        note = Synthetic
SITE                    20
                        note = misc_feature - Xaa is S5, a-methyl, a-alkenylglycine
                          with 5 carbon chain
SITE                    24
                        note = misc_feature - Xaa is S5, a-methyl, a-alkenylglycine
                          with 5 carbon chaind
```

```
source                      1..26
                            mol_type = protein
                            organism = synthetic construct
SEQUENCE: 37
SEELVAEAHN LCTLLENAIX DTVXEQ                                        26

SEQ ID NO: 38               moltype = AA  length = 8
FEATURE                     Location/Qualifiers
REGION                      1..8
                            note = Synthetic
SITE                        3
                            note = misc_feature - Xaa is S5, a-methyl, a-alkenylglycine
                             with 5 carbon chain
SITE                        7
                            note = misc_feature - Xaa is S5, a-methyl, a-alkenylglycine
                             with 5 carbon chain
source                      1..8
                            mol_type = protein
                            organism = synthetic construct
SEQUENCE: 38
FSXLWKXL                                                             8

SEQ ID NO: 39               moltype = AA  length = 8
FEATURE                     Location/Qualifiers
REGION                      1..8
                            note = Synthetic
SITE                        3
                            note = misc_feature - Xaa is S5, a-methyl, a-alkenylglycine
                             with 5 carbon chain
SITE                        7
                            note = misc_feature - Xaa is S5, a-methyl, a-alkenylglycine
                             with 5 carbon chain
source                      1..8
                            mol_type = protein
                            organism = synthetic construct
SEQUENCE: 39
FMXYWKXL                                                             8

SEQ ID NO: 40               moltype = AA  length = 10
FEATURE                     Location/Qualifiers
REGION                      1..10
                            note = Synthetic
SITE                        5
                            note = misc_feature - Xaa is S5, a-methyl, a-alkenylglycine
                             with 5 carbon chain
SITE                        9
                            note = misc_feature - Xaa is S5, a-methyl, a-alkenylglycine
                             with 5 carbon chain
source                      1..10
                            mol_type = protein
                            organism = synthetic construct
SEQUENCE: 40
QTFSXLWKXL                                                          10

SEQ ID NO: 41               moltype = AA  length = 12
FEATURE                     Location/Qualifiers
REGION                      1..12
                            note = Synthetic
SITE                        7
                            note = misc_feature - Xaa is S5, a-methyl, a-alkenylglycine
                             with 5 carbon chain
SITE                        11
                            note = misc_feature - Xaa is S5, a-methyl, a-alkenylglycine
                             with 5 carbon chain
source                      1..12
                            mol_type = protein
                            organism = synthetic construct
SEQUENCE: 41
PPKKFRXLFF XS                                                       12

SEQ ID NO: 42               moltype = AA  length = 10
FEATURE                     Location/Qualifiers
REGION                      1..10
                            note = Synthetic
SITE                        3
                            note = misc_feature - Xaa is pff,
                             pentafluoro-L-phenylalanine
SITE                        5
                            note = misc_feature - Xaa is S5, a-methyl, a-alkenylglycine
```

```
                              with 5 carbon chain
SITE                      9
                          note = misc_feature - Xaa is S5, a-methyl, a-alkenylglycine
                              with 5 carbon chain
source                    1..10
                          mol_type = protein
                          organism = synthetic construct
SEQUENCE: 42
KKFRXLFFXS                                                                  10

SEQ ID NO: 43             moltype = AA  length = 10
FEATURE                   Location/Qualifiers
REGION                    1..10
                          note = Synthetic
SITE                      3
                          note = misc_feature - Xaa is pff,
                              pentafluoro-L-phenylalanine
SITE                      4
                          note = misc_feature - Xaa is S5, a-methyl, a-alkenylglycine
                              with 5 carbon chain
SITE                      8
                          note = misc_feature - Xaa is S5, a-methyl, a-alkenylglycine
                              with 5 carbon chain
source                    1..10
                          mol_type = protein
                          organism = synthetic construct
SEQUENCE: 43
RKFXRLFXSY                                                                  10

SEQ ID NO: 44             moltype = AA  length = 10
FEATURE                   Location/Qualifiers
REGION                    1..10
                          note = Synthetic
SITE                      4
                          note = misc_feature - Xaa is S5, a-methyl, a-alkenylglycine
                              with 5 carbon chain
SITE                      8
                          note = misc_feature - Xaa is S5, a-methyl, a-alkenylglycine
                              with 5 carbon chain
source                    1..10
                          mol_type = protein
                          organism = synthetic construct
SEQUENCE: 44
RKFXRLFXSY                                                                  10

SEQ ID NO: 45             moltype = AA  length = 10
FEATURE                   Location/Qualifiers
REGION                    1..10
                          note = Synthetic
SITE                      2
                          note = misc_feature - Xaa is pff,
                              pentafluoro-L-phenylalanine
SITE                      4
                          note = misc_feature - Xaa is S5, a-methyl, a-alkenylglycine
                              with 5 carbon chain
SITE                      8
                          note = misc_feature - Xaa is S5, a-methyl, a-alkenylglycine
                              with 5 carbon chain
source                    1..10
                          mol_type = protein
                          organism = synthetic construct
SEQUENCE: 45
RFKXRLFXSY                                                                  10

SEQ ID NO: 46             moltype = AA  length = 8
FEATURE                   Location/Qualifiers
REGION                    1..8
                          note = Synthetic
SITE                      3
                          note = misc_feature - Xaa is S5, a-methyl, a-alkenylglycine
                              with 5 carbon chain
SITE                      7
                          note = misc_feature - Xaa is S5, a-methyl, a-alkenylglycine
                              with 5 carbon chain
source                    1..8
                          mol_type = protein
                          organism = synthetic construct
SEQUENCE: 46
AMXYWKXL                                                                     8
```

```
SEQ ID NO: 47          moltype = AA   length = 10
FEATURE                Location/Qualifiers
REGION                 1..10
                       note = Synthetic
SITE                   6
                       note = misc_feature - Xaa is R5, an enantiomer of S5,
                        a-methyl, a-alkenylglycine with 5 carbon chain
SITE                   9
                       note = misc_feature - Xaa is S5, a-methyl, a-alkenylglycine
                        with 5 carbon chain
source                 1..10
                       mol_type = protein
                       organism = synthetic construct
SEQUENCE: 47
QTFSDXWKXL                                                                      10

SEQ ID NO: 48          moltype = AA   length = 10
FEATURE                Location/Qualifiers
REGION                 1..10
                       note = Synthetic 220
SITE                   5
                       note = misc_feature - Xaa is S5, a-methyl, a-alkenylglycine
                        with 5 carbon chain
SITE                   9
                       note = misc_feature - Xaa is S5, a-methyl, a-alkenylglycine
                        with 5 carbon chain
source                 1..10
                       mol_type = protein
                       organism = synthetic construct
SEQUENCE: 48
KKFRXLFFXS                                                                      10

SEQ ID NO: 49          moltype = AA   length = 12
FEATURE                Location/Qualifiers
REGION                 1..12
                       note = Synthetic
SITE                   6
                       note = misc_feature - Xaa is is S5, a-methyl,
                        a-alkenylglycine with 5 carbon chain
SITE                   11
                       note = misc_feature - Xaa is S5, a-methyl, a-alkenylglycine
                        with 5 carbon chain
source                 1..12
                       mol_type = protein
                       organism = synthetic construct
SEQUENCE: 49
RRLFRXNLFL XT                                                                   12

SEQ ID NO: 50          moltype = AA   length = 10
FEATURE                Location/Qualifiers
REGION                 1..10
                       note = Synthetic
SITE                   3
                       note = misc_feature - Xaa is pff,
                        pentafluoro-L-phenylalanine
SITE                   4
                       note = misc_feature - Xaa is S5, a-methyl, a-alkenylglycine
                        with 5 carbon chain
SITE                   8
                       note = misc_feature - Xaa is S5, a-methyl, a-alkenylglycine
                        with 5 carbon chain
source                 1..10
                       mol_type = protein
                       organism = synthetic construct
SEQUENCE: 50
RRFXRLFXSY                                                                      10

SEQ ID NO: 51          moltype = AA   length = 10
FEATURE                Location/Qualifiers
REGION                 1..10
                       note = Synthetic
SITE                   4
                       note = misc_feature - Xaa is S5, a-methyl, a-alkenylglycine
                        with 5 carbon chain
SITE                   8
                       note = misc_feature - Xaa is S5, a-methyl, a-alkenylglycine
                        with 5 carbon chain
source                 1..10
```

```
                        mol_type = protein
                        organism = synthetic construct
SEQUENCE: 51
RKAXRLFXSY                                                              10

SEQ ID NO: 52           moltype = AA   length = 7
FEATURE                 Location/Qualifiers
REGION                  1..7
                        note = Synthetic
SITE                    1
                        note = misc_feature - Xaa is S5, a-methyl, a-alkenylglycine
                         with 5 carbon chain
SITE                    5
                        note = misc_feature - Xaa is S5, a-methyl, a-alkenylglycine
                         with 5 carbon chain
source                  1..7
                        mol_type = protein
                        organism = synthetic construct
SEQUENCE: 52
XRLFXSY                                                                 7

SEQ ID NO: 53           moltype = AA   length = 13
FEATURE                 Location/Qualifiers
REGION                  1..13
                        note = Synthetic
SITE                    8
                        note = misc_feature - Xaa is S5, a-methyl, a-alkenylglycine
                         with 5 carbon chain
SITE                    12
                        note = misc_feature - Xaa is S5, a-methyl, a-alkenylglycine
                         with 5 carbon chain
source                  1..13
                        mol_type = protein
                        organism = synthetic construct
SEQUENCE: 53
KQKRKFSXFF KXL                                                          13

SEQ ID NO: 54           moltype = AA   length = 13
FEATURE                 Location/Qualifiers
REGION                  1..13
                        note = Synthetic
SITE                    6
                        note = misc_feature - Xaa is pff,
                         pentafluoro-L-phenylalanine
SITE                    8
                        note = misc_feature - Xaa is S5, a-methyl, a-alkenylglycine
                         with 5 carbon chain
SITE                    12
                        note = misc_feature - Xaa is S5, a-methyl, a-alkenylglycine
                         with 5 carbon chain
source                  1..13
                        mol_type = protein
                        organism = synthetic construct
SEQUENCE: 54
KQKRKFSXFF KXL                                                          13

SEQ ID NO: 55           moltype = AA   length = 7
FEATURE                 Location/Qualifiers
REGION                  1..7
                        note = Synthetic
SITE                    3
                        note = misc_feature - Xaa is S5, a-methyl, a-alkenylglycine
                         with 5 carbon chain
SITE                    7
                        note = misc_feature - Xaa is S5, a-methyl, a-alkenylglycine
                         with 5 carbon chain
source                  1..7
                        mol_type = protein
                        organism = synthetic construct
SEQUENCE: 55
KFXRLFX                                                                 7

SEQ ID NO: 56           moltype =    length =
SEQUENCE: 56
000

SEQ ID NO: 57           moltype = AA   length = 8
FEATURE                 Location/Qualifiers
REGION                  1..8
```

```
                              note = Synthetic
SITE                          4
                              note = misc_feature - Xaa is S5, a-methyl, a-alkenylglycine
                               with 5 carbon chain
SITE                          8
                              note = misc_feature - Xaa is S5, a-methyl, a-alkenylglycine
                               with 5 carbon chain
source                        1..8
                              mol_type = protein
                              organism = synthetic construct
SEQUENCE: 57
RKFXRLFX                                                                          8

SEQ ID NO: 58                 moltype = AA  length = 14
FEATURE                       Location/Qualifiers
REGION                        1..14
                              note = Synthetic
SITE                          8
                              note = misc_feature - Xaa is S5, a-methyl, a-alkenylglycine
                               with 5 carbon chain
SITE                          12
                              note = misc_feature - Xaa is S5, a-methyl, a-alkenylglycine
                               with 5 carbon chain
source                        1..14
                              mol_type = protein
                              organism = synthetic construct
SEQUENCE: 58
KQKRKFSXFF KXLV                                                                  14

SEQ ID NO: 59                 moltype = AA  length = 13
FEATURE                       Location/Qualifiers
REGION                        1..13
                              note = Synthetic
SITE                          3
                              note = misc_feature - Xaa is pff,
                               pentafluoro-L-phenylalanine
SITE                          8
                              note = misc_feature - Xaa is S5, a-methyl, a-alkenylglycine
                               with 5 carbon chain
SITE                          12
                              note = misc_feature - Xaa is S5, a-methyl, a-alkenylglycine
                               with 5 carbon chain
source                        1..13
                              mol_type = protein
                              organism = synthetic construct
SEQUENCE: 59
KQFRKKSXFF KXL                                                                   13

SEQ ID NO: 60                 moltype = AA  length = 8
FEATURE                       Location/Qualifiers
REGION                        1..8
                              note = Synthetic
SITE                          3
                              note = misc_feature - Xaa is pff,
                               pentafluoro-L-phenylalanine
SITE                          4
                              note = misc_feature - Xaa is S5, a-methyl, a-alkenylglycine
                               with 5 carbon chain
SITE                          8
                              note = misc_feature - Xaa is S5, a-methyl, a-alkenylglycine
                               with 5 carbon chain
source                        1..8
                              mol_type = protein
                              organism = synthetic construct
SEQUENCE: 60
RKFXRLFX                                                                          8

SEQ ID NO: 61                 moltype = AA  length = 6
FEATURE                       Location/Qualifiers
REGION                        1..6
                              note = Synthetic
SITE                          2
                              note = misc_feature - Xaa is S5, a-methyl, a-alkenylglycine
                               with 5 carbon chain
SITE                          6
                              note = misc_feature - Xaa is S5, a-methyl, a-alkenylglycine
                               with 5 carbon chain
source                        1..6
                              mol_type = protein
```

```
SEQUENCE: 61
FXRLFX                                                                  6

SEQ ID NO: 62           moltype = AA   length = 16
FEATURE                 Location/Qualifiers
REGION                  1..16
                        note = Synthetic
SITE                    9
                        note = misc_feature - Xaa is S5, a-methyl, a-alkenylglycine
                         with 5 carbon chain
SITE                    13
                        note = misc_feature - Xaa is S5, a-methyl, a-alkenylglycine
                         with 5 carbon chain
source                  1..16
                        mol_type = protein
                        organism = synthetic construct
SEQUENCE: 62
KTYRGAFQXL FQXVRE                                                       16

SEQ ID NO: 63           moltype = AA   length = 22
FEATURE                 Location/Qualifiers
REGION                  1..22
                        note = Synthetic
SITE                    6
                        note = misc_feature - Xaa is S5, a-methyl, a-alkenylglycine
                         with 5 carbon chain
SITE                    10
                        note = misc_feature - Xaa is S5, a-methyl, a-alkenylglycine
                         with 5 carbon chain
source                  1..22
                        mol_type = protein
                        organism = synthetic construct
SEQUENCE: 63
STALRXLIEX LVNITQNQKA PL                                                22

SEQ ID NO: 64           moltype = AA   length = 22
FEATURE                 Location/Qualifiers
REGION                  1..22
                        note = Synthetic
SITE                    9
                        note = misc_feature - Xaa is S5, a-methyl, a-alkenylglycine
                         with 5 carbon chain
SITE                    13
                        note = misc_feature - Xaa is S5, a-methyl, a-alkenylglycine
                         with 5 carbon chain
source                  1..22
                        mol_type = protein
                        organism = synthetic construct
SEQUENCE: 64
STALRELIXE LVXITQNQKA PL                                                22

SEQ ID NO: 65           moltype = AA   length = 22
FEATURE                 Location/Qualifiers
REGION                  1..22
                        note = Synthetic
SITE                    12
                        note = misc_feature - Xaa is S5, a-methyl, a-alkenylglycine
                         with 5 carbon chain
SITE                    16
                        note = misc_feature - Xaa is S5, a-methyl, a-alkenylglycine
                         with 5 carbon chain
source                  1..22
                        mol_type = protein
                        organism = synthetic construct
SEQUENCE: 65
STALRELIEE LXNITXNQKA PL                                                22

SEQ ID NO: 66           moltype = AA   length = 24
FEATURE                 Location/Qualifiers
REGION                  1..24
                        note = Synthetic
SITE                    5
                        note = misc_feature - Xaa is S5, a-methyl, a-alkenylglycine
                         with 5 carbon chain
SITE                    9
                        note = misc_feature - Xaa is S5, a-methyl, a-alkenylglycine
                         with 5 carbon chain
source                  1..24
```

```
                              mol_type = protein
                              organism = synthetic construct
SEQUENCE: 66
NELKXSFFXL RDQIPELENN EKAP                                            24

SEQ ID NO: 67              moltype = AA   length = 16
FEATURE                    Location/Qualifiers
REGION                     1..16
                              note = Synthetic
SITE                       6
                              note = misc_feature - Xaa is S5, a-methyl, a-alkenylglycine
                              with 5 carbon chain
SITE                       10
                              note = misc_feature - Xaa is S5, a-methyl, a-alkenylglycine
                              with 5 carbon chain
source                     1..16
                              mol_type = protein
                              organism = synthetic construct
SEQUENCE: 67
LENRQXKLEX ANRHLL                                                     16

SEQ ID NO: 68              moltype = AA   length = 16
FEATURE                    Location/Qualifiers
REGION                     1..16
                              note = Synthetic
SITE                       3
                              note = misc_feature - Xaa is S5, a-methyl, a-alkenylglycine
                              with 5 carbon chain
SITE                       7
                              note = misc_feature - Xaa is S5, a-methyl, a-alkenylglycine
                              with 5 carbon chain
source                     1..16
                              mol_type = protein
                              organism = synthetic construct
SEQUENCE: 68
ILXASVXYIR KLQREQ                                                     16

SEQ ID NO: 69              moltype = AA   length = 14
FEATURE                    Location/Qualifiers
REGION                     1..14
                              note = Synthetic
SITE                       4
                              note = misc_feature - Xaa is S5, a-methyl, a-alkenylglycine
                              with 5 carbon chain
SITE                       8
                              note = misc_feature - Xaa is S5, a-methyl, a-alkenylglycine
                              with 5 carbon chain
source                     1..14
                              mol_type = protein
                              organism = synthetic construct
SEQUENCE: 69
FNIXDRIXEL GTLI                                                       14

SEQ ID NO: 70              moltype = AA   length = 9
FEATURE                    Location/Qualifiers
REGION                     1..9
                              note = Synthetic
SITE                       3
                              note = misc_feature - Xaa is S5, a-methyl, a-alkenylglycine
                              with 5 carbon chain
SITE                       7
                              note = misc_feature - Xaa is S5, a-methyl, a-alkenylglycine
                              with 5 carbon chain
source                     1..9
                              mol_type = protein
                              organism = synthetic construct
SEQUENCE: 70
KNXTHQXDI                                                              9

SEQ ID NO: 71              moltype = AA   length = 22
FEATURE                    Location/Qualifiers
REGION                     1..22
                              note = Synthetic
SITE                       13
                              note = misc_feature - Xaa is S5, a-methyl, a-alkenylglycine
                              with 5 carbon chain
SITE                       17
                              note = misc_feature - Xaa is S5, a-methyl, a-alkenylglycine
                              with 5 carbon chain
```

```
source                  1..22
                        mol_type = protein
                        organism = synthetic construct
SEQUENCE: 71
STALRELIEE LVXITQXQKA PL                                            22

SEQ ID NO: 72           moltype = AA  length = 14
FEATURE                 Location/Qualifiers
REGION                  1..14
                        note = Synthetic
SITE                    5
                        note = misc_feature - Xaa is S5, a-methyl, a-alkenylglycine
                        with 5 carbon chain
SITE                    9
                        note = misc_feature - Xaa is S5, a-methyl, a-alkenylglycine
                        with 5 carbon chain
source                  1..14
                        mol_type = protein
                        organism = synthetic construct
SEQUENCE: 72
NELKXSFFXL RDQI                                                     14

SEQ ID NO: 73           moltype = AA  length = 16
FEATURE                 Location/Qualifiers
REGION                  1..16
                        note = Synthetic
SITE                    10
                        note = misc_feature - Xaa is S5, a-methyl, a-alkenylglycine
                        with 5 carbon chain
SITE                    14
                        note = misc_feature - Xaa is S5, a-methyl, a-alkenylglycine
                        with 5 carbon chain
source                  1..16
                        mol_type = protein
                        organism = synthetic construct
SEQUENCE: 73
LENRQKKLEX ANRXLL                                                   16

SEQ ID NO: 74           moltype = AA  length = 16
FEATURE                 Location/Qualifiers
REGION                  1..16
                        note = Synthetic
SITE                    6
                        note = misc_feature - Xaa is S5, a-methyl, a-alkenylglycine
                        with 5 carbon chain
SITE                    10
                        note = misc_feature - Xaa is S5, a-methyl, a-alkenylglycine
                        with 5 carbon chain
source                  1..16
                        mol_type = protein
                        organism = synthetic construct
SEQUENCE: 74
ILKASXDYIX KLQREQ                                                   16

SEQ ID NO: 75           moltype = AA  length = 14
FEATURE                 Location/Qualifiers
REGION                  1..14
                        note = Synthetic
SITE                    5
                        note = misc_feature - Xaa is S5, a-methyl, a-alkenylglycine
                        with 5 carbon chain
SITE                    9
                        note = misc_feature - Xaa is S5, a-methyl, a-alkenylglycine
                        with 5 carbon chain
source                  1..14
                        mol_type = protein
                        organism = synthetic construct
SEQUENCE: 75
DHIKXSFHXL RDSV                                                     14

SEQ ID NO: 76           moltype = AA  length = 14
FEATURE                 Location/Qualifiers
REGION                  1..14
                        note = Synthetic
SITE                    8
                        note = misc_feature - Xaa is S5, a-methyl, a-alkenylglycine
                        with 5 carbon chain
SITE                    12
                        note = misc_feature - Xaa is S5, a-methyl, a-alkenylglycine
```

```
                                with 5 carbon chain
source                      1..14
                            mol_type = protein
                            organism = synthetic construct
SEQUENCE: 76
DHIKDSFXSL RXSV                                                              14

SEQ ID NO: 77               moltype = AA  length = 38
FEATURE                     Location/Qualifiers
REGION                      1..38
                            note = Synthetic
SITE                        1
                            note = misc_feature - Xaa is S5, a-methyl, a-alkenylglycine
                                with 5 carbon chain
SITE                        5
                            note = misc_feature - Xaa is S5, a-methyl, a-alkenylglycine
                                with 5 carbon chain
source                      1..38
                            mol_type = protein
                            organism = synthetic construct
SEQUENCE: 77
XYIQXNLRRK NHTHQQDIDD LLKRQNALLE QQVRALGG                                     38

SEQ ID NO: 78               moltype = AA  length = 16
FEATURE                     Location/Qualifiers
REGION                      1..16
                            note = Synthetic
SITE                        8
                            note = misc_feature - Xaa is S5, a-methyl, a-alkenylglycine
                                with 5 carbon chain
SITE                        12
                            note = misc_feature - Xaa is S5, a-methyl, a-alkenylglycine
                                with 5 carbon chain
source                      1..16
                            mol_type = protein
                            organism = synthetic construct
SEQUENCE: 78
TYRGAAQXAA QXVREV                                                            16

SEQ ID NO: 79               moltype = AA  length = 16
FEATURE                     Location/Qualifiers
REGION                      1..16
                            note = Synthetic
SITE                        3
                            note = misc_feature - Xaa is S5, a-methyl, a-alkenylglycine
                                with 5 carbon chain
SITE                        7
                            note = misc_feature - Xaa is S5, a-methyl, a-alkenylglycine
                                with 5 carbon chain
source                      1..16
                            mol_type = protein
                            organism = synthetic construct
SEQUENCE: 79
TYXGAFXNLF QSVREV                                                            16

SEQ ID NO: 80               moltype = AA  length = 17
FEATURE                     Location/Qualifiers
REGION                      1..17
                            note = Synthetic
SITE                        2
                            note = misc_feature - Xaa is S5, a-methyl, a-alkenylglycine
                                with 5 carbon chain
SITE                        6
                            note = misc_feature - Xaa is S5, a-methyl, a-alkenylglycine
                                with 5 carbon chain
source                      1..17
                            mol_type = protein
                            organism = synthetic construct
SEQUENCE: 80
AXSVFXNYFH SVPYFEL                                                           17

SEQ ID NO: 81               moltype = AA  length = 10
FEATURE                     Location/Qualifiers
REGION                      1..10
                            note = Synthetic
SITE                        4
                            note = misc_feature - Xaa is S5, a-methyl, a-alkenylglycine
                                with 5 carbon chain
SITE                        8
```

```
                        note = misc_feature - Xaa is S5, a-methyl, a-alkenylglycine
                            with 5 carbon chain
source                  1..10
                        mol_type = protein
                        organism = synthetic construct
SEQUENCE: 81
GAFXNLFXSV                                                                        10

SEQ ID NO: 82           moltype = AA  length = 11
FEATURE                 Location/Qualifiers
REGION                  1..11
                        note = Synthetic
SITE                    1
                        note = misc_feature - Xaa is S5, a-methyl, a-alkenylglycine
                            with 5 carbon chain
SITE                    5
                        note = misc_feature - Xaa is S5, a-methyl, a-alkenylglycine
                            with 5 carbon chain
SITE                    9
                        note = misc_feature - Xaa is R5, an enantiomer of S5,
                            a-methyl, a-alkenylglycine with 5 carbon chain
source                  1..11
                        mol_type = protein
                        organism = synthetic construct
SEQUENCE: 82
XGAFXNLFXS V                                                                      11

SEQ ID NO: 83           moltype = AA  length = 16
FEATURE                 Location/Qualifiers
REGION                  1..16
                        note = Synthetic
SITE                    8
                        note = misc_feature - Xaa is S5, a-methyl, a-alkenylglycine
                            with 5 carbon chain
SITE                    12
                        note = misc_feature - Xaa is S5, a-methyl, a-alkenylglycine
                            with 5 carbon chain
source                  1..16
                        mol_type = protein
                        organism = synthetic construct
SEQUENCE: 83
SYRGAFQXLF QXVREV                                                                 16

SEQ ID NO: 84           moltype = AA  length = 16
FEATURE                 Location/Qualifiers
REGION                  1..16
                        note = Synthetic
SITE                    6
                        note = misc_feature - Xaa is S5, a-methyl, a-alkenylglycine
                            with 5 carbon chain
SITE                    10
                        note = misc_feature - Xaa is S5, a-methyl, a-alkenylglycine
                            with 5 carbon chain
source                  1..16
                        mol_type = protein
                        organism = synthetic construct
SEQUENCE: 84
SSVFYXYFHX VPYFEL                                                                 16

SEQ ID NO: 85           moltype = AA  length = 15
FEATURE                 Location/Qualifiers
REGION                  1..15
                        note = Synthetic
SITE                    2
                        note = misc_feature - Xaa is S5, a-methyl, a-alkenylglycine
                            with 5 carbon chain
SITE                    6
                        note = misc_feature - Xaa is S5, a-methyl, a-alkenylglycine
                            with 5 carbon chain
source                  1..15
                        mol_type = protein
                        organism = synthetic construct
SEQUENCE: 85
AXTLFXTFYL GGLLG                                                                  15

SEQ ID NO: 86           moltype = AA  length = 11
FEATURE                 Location/Qualifiers
REGION                  1..11
                        note = Synthetic
```

```
SITE                      1
                          note = misc_feature - Xaa can be any naturally occurring
                           amino acid
SITE                      2
                          note = misc_feature - Xaa is S5, a-methyl, a-alkenylglycine
                           with 5 carbon chain
SITE                      5
                          note = misc_feature - Xaa can be any naturally occurring
                           amino acid
SITE                      6
                          note = misc_feature - Xaa is S5, a-methyl, a-alkenylglycine
                           with 5 carbon chain
source                    1..11
                          mol_type = protein
                          organism = synthetic construct
SEQUENCE: 86
XGAFXNLFQS V                                                              11

SEQ ID NO: 87             moltype = AA  length = 17
FEATURE                   Location/Qualifiers
REGION                    1..17
                          note = Synthetic
SITE                      2
                          note = misc_feature - Xaa is S5, a-methyl, a-alkenylglycine
                           with 5 carbon chain
SITE                      6
                          note = misc_feature - Xaa is S5, a-methyl, a-alkenylglycine
                           with 5 carbon chain
source                    1..17
                          mol_type = protein
                          organism = synthetic construct
SEQUENCE: 87
AXSSFXDFFH TVPYNLL                                                        17

SEQ ID NO: 88             moltype = AA  length = 16
FEATURE                   Location/Qualifiers
REGION                    1..16
                          note = Synthetic
SITE                      8
                          note = misc_feature - Xaa is S5, a-methyl, a-alkenylglycine
                           with 5 carbon chain
SITE                      12
                          note = misc_feature - Xaa is S5, a-methyl, a-alkenylglycine
                           with 5 carbon chain
source                    1..16
                          mol_type = protein
                          organism = synthetic construct
SEQUENCE: 88
ERLRRRIXLC RXHHST                                                         16

SEQ ID NO: 89             moltype = AA  length = 17
FEATURE                   Location/Qualifiers
REGION                    1..17
                          note = Synthetic
SITE                      8
                          note = misc_feature - Xaa is S5, a-methyl, a-alkenylglycine
                           with 5 carbon chain
SITE                      13
                          note = misc_feature - Xaa is S5, a-methyl, a-alkenylglycine
                           with 5 carbon chain
source                    1..17
                          mol_type = protein
                          organism = synthetic construct
SEQUENCE: 89
ERLRRRIXNL CRXHHST                                                        17

SEQ ID NO: 90             moltype = AA  length = 16
FEATURE                   Location/Qualifiers
REGION                    1..16
                          note = Synthetic
SITE                      8
                          note = misc_feature - Xaa is S5, a-methyl, a-alkenylglycine
                           with 5 carbon chain
SITE                      12
                          note = misc_feature - Xaa is S5, a-methyl, a-alkenylglycine
                           with 5 carbon chain
source                    1..16
                          mol_type = protein
                          organism = synthetic construct
```

-continued

```
SEQUENCE: 90
ERLRRRLXLC RXHHST                                                   16

SEQ ID NO: 91           moltype = AA  length = 16
FEATURE                 Location/Qualifiers
REGION                  1..16
                        note = Synthetic
SITE                    8
                        note = misc_feature - Xaa is S5, a-methyl, a-alkenylglycine
                         with 5 carbon chain
SITE                    12
                        note = misc_feature - Xaa is S5, a-methyl, a-alkenylglycine
                         with 5 carbon chain
source                  1..16
                        mol_type = protein
                        organism = synthetic construct
SEQUENCE: 91
ERLRRRFXLC RXHHST                                                   16

SEQ ID NO: 92           moltype = AA  length = 16
FEATURE                 Location/Qualifiers
REGION                  1..16
                        note = Synthetic
SITE                    8
                        note = misc_feature - Xaa is S5, a-methyl, a-alkenylglycine
                         with 5 carbon chain
SITE                    12
                        note = misc_feature - Xaa is S5, a-methyl, a-alkenylglycine
                         with 5 carbon chain
source                  1..16
                        mol_type = protein
                        organism = synthetic construct
SEQUENCE: 92
ERFRRRIXLC RXHHST                                                   16

SEQ ID NO: 93           moltype = AA  length = 16
FEATURE                 Location/Qualifiers
REGION                  1..16
                        note = Synthetic
SITE                    8
                        note = misc_feature - Xaa is S5, a-methyl, a-alkenylglycine
                         with 5 carbon chain
SITE                    12
                        note = misc_feature - Xaa is S5, a-methyl, a-alkenylglycine
                         with 5 carbon chain
source                  1..16
                        mol_type = protein
                        organism = synthetic construct
SEQUENCE: 93
ERLARRIXLC RXHHST                                                   16

SEQ ID NO: 94           moltype = AA  length = 15
FEATURE                 Location/Qualifiers
REGION                  1..15
                        note = Synthetic
SITE                    9
                        note = misc_feature - Xaa is S5, a-methyl, a-alkenylglycine
                         with 5 carbon chain
SITE                    13
                        note = misc_feature - Xaa is S5, a-methyl, a-alkenylglycine
                         with 5 carbon chain
source                  1..15
                        mol_type = protein
                        organism = synthetic construct
SEQUENCE: 94
ENPESILDXH VQXVM                                                    15

SEQ ID NO: 95           moltype = AA  length = 13
FEATURE                 Location/Qualifiers
REGION                  1..13
                        note = Synthetic
SITE                    3
                        note = misc_feature - Xaa is S5, a-methyl, a-alkenylglycine
                         with 5 carbon chain
SITE                    7
                        note = misc_feature - Xaa is S5, a-methyl, a-alkenylglycine
                         with 5 carbon chain
source                  1..13
                        mol_type = protein
```

-continued

```
SEQUENCE: 95
PEXILDXHVQ RVM                                                          13

SEQ ID NO: 96           moltype = AA   length = 16
FEATURE                 Location/Qualifiers
REGION                  1..16
                        note = Synthetic
SITE                    8
                        note = misc_feature - Xaa is S5, a-methyl, a-alkenylglycine
                          with 5 carbon chain
SITE                    12
                        note = misc_feature - Xaa is S5, a-methyl, a-alkenylglycine
                          with 5 carbon chain
source                  1..16
                        mol_type = protein
                        organism = synthetic construct
SEQUENCE: 96
ERLRRRIXFC RXHHST                                                       16

SEQ ID NO: 97           moltype = AA   length = 17
FEATURE                 Location/Qualifiers
REGION                  1..17
                        note = Synthetic
SITE                    9
                        note = misc_feature - Xaa is S5, a-methyl, a-alkenylglycine
                          with 5 carbon chain
SITE                    13
                        note = misc_feature - Xaa is S5, a-methyl, a-alkenylglycine
                          with 5 carbon chain
source                  1..17
                        mol_type = protein
                        organism = synthetic construct
SEQUENCE: 97
ERLRRRNLXL CRXHHST                                                      17

SEQ ID NO: 98           moltype = AA   length = 17
FEATURE                 Location/Qualifiers
REGION                  1..17
                        note = Synthetic
SITE                    9
                        note = misc_feature - Xaa is S5, a-methyl, a-alkenylglycine
                          with 5 carbon chain
SITE                    13
                        note = misc_feature - Xaa is S5, a-methyl, a-alkenylglycine
                          with 5 carbon chain
source                  1..17
                        mol_type = protein
                        organism = synthetic construct
SEQUENCE: 98
ERNLRRRIXL CRXHHST                                                      17

SEQ ID NO: 99           moltype = AA   length = 16
FEATURE                 Location/Qualifiers
REGION                  1..16
                        note = Synthetic
SITE                    8
                        note = misc_feature - Xaa is S5, a-methyl, a-alkenylglycine
                          with 5 carbon chain
SITE                    12
                        note = misc_feature - Xaa is S5, a-methyl, a-alkenylglycine
                          with 5 carbon chain
source                  1..16
                        mol_type = protein
                        organism = synthetic construct
SEQUENCE: 99
ERWRRRIXLC RXHHST                                                       16

SEQ ID NO: 100          moltype = AA   length = 16
FEATURE                 Location/Qualifiers
REGION                  1..16
                        note = Synthetic
SITE                    8
                        note = misc_feature - Xaa is S5, a-methyl, a-alkenylglycine
                          with 5 carbon chain
SITE                    12
                        note = misc_feature - Xaa is S5, a-methyl, a-alkenylglycine
                          with 5 carbon chain
source                  1..16
```

```
                        mol_type = protein
                        organism = synthetic construct
SEQUENCE: 100
RELRREIXLC RXHHST                                                           16

SEQ ID NO: 101          moltype = AA  length = 15
FEATURE                 Location/Qualifiers
REGION                  1..15
                        note = Synthetic
SITE                    5
                        note = misc_feature - Xaa is S5, a-methyl, a-alkenylglycine
                          with 5 carbon chain
SITE                    9
                        note = misc_feature - Xaa is S5, a-methyl, a-alkenylglycine
                          with 5 carbon chain
source                  1..15
                        mol_type = protein
                        organism = synthetic construct
SEQUENCE: 101
ENPEXILDXH VQRVM                                                            15

SEQ ID NO: 102          moltype = AA  length = 14
FEATURE                 Location/Qualifiers
REGION                  1..14
                        note = Synthetic
SITE                    4
                        note = misc_feature - Xaa is S5, a-methyl, a-alkenylglycine
                          with 5 carbon chain
SITE                    8
                        note = misc_feature - Xaa is S5, a-methyl, a-alkenylglycine
                          with 5 carbon chain
source                  1..14
                        mol_type = protein
                        organism = synthetic construct
SEQUENCE: 102
NPEXILDXHV QRVM                                                             14

SEQ ID NO: 103          moltype = AA  length = 14
FEATURE                 Location/Qualifiers
REGION                  1..14
                        note = Synthetic
SITE                    4
                        note = misc_feature - Xaa is S5, a-methyl, a-alkenylglycine
                          with 5 carbon chain
SITE                    8
                        note = misc_feature - Xaa is S5, a-methyl, a-alkenylglycine
                          with 5 carbon chain
source                  1..14
                        mol_type = protein
                        organism = synthetic construct
SEQUENCE: 103
WPEXILDXHV QRVM                                                             14

SEQ ID NO: 104          moltype = AA  length = 14
FEATURE                 Location/Qualifiers
REGION                  1..14
                        note = Synthetic
SITE                    3
                        note = misc_feature - Xaa is S5, a-methyl, a-alkenylglycine
                          with 5 carbon chain
SITE                    7
                        note = misc_feature - Xaa is S5, a-methyl, a-alkenylglycine
                          with 5 carbon chain
source                  1..14
                        mol_type = protein
                        organism = synthetic construct
SEQUENCE: 104
PEXILDXHVR RVMR                                                             14

SEQ ID NO: 105          moltype = AA  length = 15
FEATURE                 Location/Qualifiers
REGION                  1..15
                        note = Synthetic
SITE                    4
                        note = misc_feature - Xaa is S5, a-methyl, a-alkenylglycine
                          with 5 carbon chain
SITE                    8
                        note = misc_feature - Xaa is S5, a-methyl, a-alkenylglycine
                          with 5 carbon chain
```

```
source                  1..15
                        mol_type = protein
                        organism = synthetic construct
SEQUENCE: 105
RPEXILDXHV RRVMR                                                            15

SEQ ID NO: 106          moltype = AA  length = 14
FEATURE                 Location/Qualifiers
REGION                  1..14
                        note = Synthetic
SITE                    5
                        note = misc_feature - Xaa is R8, an enantiomer of S8,
                         a-methyl, a-alkenylglycine with 8 carbon chain
SITE                    12
                        note = misc_feature - Xaa is S5, a-methyl, a-alkenylglycine
                         with 5 carbon chain
source                  1..14
                        mol_type = protein
                        organism = synthetic construct
SEQUENCE: 106
TRQAXRNRRR RXRR                                                             14

SEQ ID NO: 107          moltype = AA  length = 17
FEATURE                 Location/Qualifiers
REGION                  1..17
                        note = Synthetic
SITE                    10
                        note = misc_feature - Xaa is R8, an enantiomer of S8,
                         a-methyl, a-alkenylglycine with 8 carbon chain
SITE                    17
                        note = misc_feature - Xaa is S5, a-methyl, a-alkenylglycine
                         with 5 carbon chain
source                  1..17
                        mol_type = protein
                        organism = synthetic construct
SEQUENCE: 107
RRGSRPSGAX RRRRRAX                                                          17

SEQ ID NO: 108          moltype = AA  length = 19
FEATURE                 Location/Qualifiers
REGION                  1..19
                        note = Synthetic
SITE                    10
                        note = misc_feature - Xaa is R8, an enantiomer of S8,
                         a-methyl, a-alkenylglycine with 8 carbon chain
SITE                    17
                        note = misc_feature - Xaa is S5, a-methyl, a-alkenylglycine
                         with 5 carbon chain
source                  1..19
                        mol_type = protein
                        organism = synthetic construct
SEQUENCE: 108
RRGSRPSGAX RRRRRAXAA                                                        19

SEQ ID NO: 109          moltype = AA  length = 17
FEATURE                 Location/Qualifiers
REGION                  1..17
                        note = Synthetic
SITE                    8
                        note = misc_feature - Xaa is R8, an enantiomer of S8,
                         a-methyl, a-alkenylglycine with 8 carbon chain
SITE                    15
                        note = misc_feature - Xaa is S5, a-methyl, a-alkenylglycine
                         with 5 carbon chain
source                  1..17
                        mol_type = protein
                        organism = synthetic construct
SEQUENCE: 109
TRQARRNXRR RWREXQR                                                          17

SEQ ID NO: 110          moltype = AA  length = 12
FEATURE                 Location/Qualifiers
REGION                  1..12
                        note = Synthetic
SITE                    5
                        note = misc_feature - Xaa is R5, an enantiomer of S5,
                         a-methyl, a-alkenylglycine with 5 carbon chain
SITE                    12
                        note = misc_feature - Xaa is S8, a-methyl, a-alkenylglycine
```

```
                              with 8 carbon chain
source                  1..12
                        mol_type = protein
                        organism = synthetic construct
SEQUENCE: 110
RRRRXRRRWR RX                                                              12

SEQ ID NO: 111          moltype = AA  length = 14
FEATURE                 Location/Qualifiers
REGION                  1..14
                        note = Synthetic
SITE                    4
                        note = misc_feature - Xaa is S5, a-methyl, a-alkenylglycine
                         with 5 carbon chain
SITE                    8
                        note = misc_feature - Xaa is S5, a-methyl, a-alkenylglycine
                         with 5 carbon chain
source                  1..14
                        mol_type = protein
                        organism = synthetic construct
SEQUENCE: 111
KPEXILDXHV QRVM                                                            14

SEQ ID NO: 112          moltype = AA  length = 15
FEATURE                 Location/Qualifiers
REGION                  1..15
                        note = Synthetic
SITE                    4
                        note = misc_feature - Xaa is S5, a-methyl, a-alkenylglycine
                         with 5 carbon chain
SITE                    8
                        note = misc_feature - Xaa is S5, a-methyl, a-alkenylglycine
                         with 5 carbon chain
source                  1..15
                        mol_type = protein
                        organism = synthetic construct
SEQUENCE: 112
WPEXILDXHV RRVMR                                                           15

SEQ ID NO: 113          moltype = AA  length = 14
FEATURE                 Location/Qualifiers
REGION                  1..14
                        note = Synthetic
SITE                    5
                        note = misc_feature - Xaa is R8, an enantiomer of S8,
                         a-methyl, a-alkenylglycine with 8 carbon chain
SITE                    12
                        note = misc_feature - Xaa is S5, a-methyl, a-alkenylglycine
                         with 5 carbon chain
source                  1..14
                        mol_type = protein
                        organism = synthetic construct
SEQUENCE: 113
RRRRXRQRRR RXRR                                                            14

SEQ ID NO: 114          moltype = AA  length = 17
FEATURE                 Location/Qualifiers
REGION                  1..17
                        note = Synthetic
SITE                    10
                        note = misc_feature - Xaa is R8, an enantiomer of S8,
                         a-methyl, a-alkenylglycine with 8 carbon chain
SITE                    17
                        note = misc_feature - Xaa is S5, a-methyl, a-alkenylglycine
                         with 5 carbon chain
source                  1..17
                        mol_type = protein
                        organism = synthetic construct
SEQUENCE: 114
RRGSRPSGAX RRRRRX                                                          17

SEQ ID NO: 115          moltype = AA  length = 15
FEATURE                 Location/Qualifiers
REGION                  1..15
                        note = Synthetic
SITE                    1
                        note = misc_feature - Xaa is R8, an enantiomer of S8,
                         a-methyl, a-alkenylglycine with 8 carbon chain
SITE                    8
```

-continued

```
                        note = misc_feature - Xaa is S5, a-methyl, a-alkenylglycine
                          with 5 carbon chain
source                  1..15
                        mol_type = protein
                        organism = synthetic construct
SEQUENCE: 115
XRRQRRRXRQ RRRRR                                                             15

SEQ ID NO: 116          moltype = AA  length = 12
FEATURE                 Location/Qualifiers
REGION                  1..12
                        note = Synthetic
SITE                    5
                        note = misc_feature - Xaa is R5, an enantiomer of S5,
                          a-methyl, a-alkenylglycine with 5 carbon chain
SITE                    12
                        note = misc_feature - Xaa is S8, a-methyl, a-alkenylglycine
                          with 8 carbon chain
source                  1..12
                        mol_type = protein
                        organism = synthetic construct
SEQUENCE: 116
RRRRXRRRRR RX                                                                12

SEQ ID NO: 117          moltype = AA  length = 12
FEATURE                 Location/Qualifiers
REGION                  1..12
                        note = Synthetic
SITE                    5
                        note = misc_feature - Xaa is R5, an enantiomer of S5,
                          a-methyl, a-alkenylglycine with 5 carbon chain
SITE                    12
                        note = misc_feature - Xaa is S8, a-methyl, a-alkenylglycine
                          with 8 carbon chain
source                  1..12
                        mol_type = protein
                        organism = synthetic construct
SEQUENCE: 117
YGRKXRRQRR RX                                                                12

SEQ ID NO: 118          moltype = AA  length = 26
FEATURE                 Location/Qualifiers
REGION                  1..26
                        note = Synthetic
SITE                    2
                        note = misc_feature - Xaa is R8, an enantiomer of S8,
                          a-methyl, a-alkenylglycine with 8 carbon chain
SITE                    9
                        note = misc_feature - Xaa is S5, a-methyl, a-alkenylglycine
                          with 5 carbon chain
source                  1..26
                        mol_type = protein
                        organism = synthetic construct
SEQUENCE: 118
SXELVAEAXN LCTLLENAIQ DTVREQ                                                 26

SEQ ID NO: 119          moltype = AA  length = 26
FEATURE                 Location/Qualifiers
REGION                  1..26
                        note = Synthetic
SITE                    10
                        note = misc_feature - Xaa is R8, an enantiomer of S8,
                          a-methyl, a-alkenylglycine with 8 carbon chain
SITE                    17
                        note = misc_feature - Xaa is S5, a-methyl, a-alkenylglycine
                          with 5 carbon chain
source                  1..26
                        mol_type = protein
                        organism = synthetic construct
SEQUENCE: 119
SEELVAEAHX LCTLLEXAIQ DTVREQ                                                 26

SEQ ID NO: 120          moltype = AA  length = 26
FEATURE                 Location/Qualifiers
REGION                  1..26
                        note = Synthetic
SITE                    14
                        note = misc_feature - Xaa is R8, an enantiomer of S8,
                          a-methyl, a-alkenylglycine with 8 carbon chain
```

| | |
|---|---|
| SITE | 21<br>note = misc_feature - Xaa is S5, a-methyl, a-alkenylglycine with 5 carbon chain |
| source | 1..26<br>mol_type = protein<br>organism = synthetic construct |

SEQUENCE: 120
SEELVAEAHN LCTXLENAIQ XTVREQ                                           26

| | |
|---|---|
| SEQ ID NO: 121 | moltype = AA  length = 16 |
| FEATURE | Location/Qualifiers |
| REGION | 1..16<br>note = Synthetic |
| SITE | 7<br>note = misc_feature - Xaa is R5, an enantiomer of S5, a-methyl, a-alkenylglycine with 5 carbon chain |
| SITE | 14<br>note = misc_feature - Xaa is S8, a-methyl, a-alkenylglycine with 8 carbon chain |
| source | 1..16<br>mol_type = protein<br>organism = synthetic construct |

SEQUENCE: 121
RQIKIWXQNR RMKXKK                                                      16

| | |
|---|---|
| SEQ ID NO: 122 | moltype = AA  length = 26 |
| FEATURE | Location/Qualifiers |
| REGION | 1..26<br>note = Synthetic |
| SITE | 3<br>note = misc_feature - Xaa is R8, an enantiomer of S8, a-methyl, a-alkenylglycine with 8 carbon chain |
| SITE | 10<br>note = misc_feature - Xaa is S5, a-methyl, a-alkenylglycine with 5 carbon chain |
| source | 1..26<br>mol_type = protein<br>organism = synthetic construct |

SEQUENCE: 122
SEXLVAEAHX LCTLLENAIQ DTVREQ                                           26

| | |
|---|---|
| SEQ ID NO: 123 | moltype = AA  length = 26 |
| FEATURE | Location/Qualifiers |
| REGION | 1..26<br>note = Synthetic |
| SITE | 13<br>note = misc_feature - Xaa is R8, an enantiomer of S8, a-methyl, a-alkenylglycine with 8 carbon chain |
| SITE | 20<br>note = misc_feature - Xaa is S5, a-methyl, a-alkenylglycine with 5 carbon chain |
| source | 1..26<br>mol_type = protein<br>organism = synthetic construct |

SEQUENCE: 123
SEELVAEAHN LCXLLENAIX DTVREQ                                           26

| | |
|---|---|
| SEQ ID NO: 124 | moltype = AA  length = 26 |
| FEATURE | Location/Qualifiers |
| REGION | 1..26<br>note = Synthetic |
| SITE | 17<br>note = misc_feature - Xaa is R8, an enantiomer of S8, a-methyl, a-alkenylglycine with 8 carbon chain |
| SITE | 24<br>note = misc_feature - Xaa is S5, a-methyl, a-alkenylglycine with 5 carbon chain |
| source | 1..26<br>mol_type = protein<br>organism = synthetic construct |

SEQUENCE: 124
SEELVAEAHN LCTLLEXAIQ DTVXEQ                                           26

| | |
|---|---|
| SEQ ID NO: 125 | moltype = AA  length = 16 |
| FEATURE | Location/Qualifiers |
| REGION | 1..16<br>note = Synthetic |
| SITE | 7<br>note = misc_feature - Xaa is R8, an enantiomer of S8, |

```
                        a-methyl, a-alkenylglycine with 8 carbon chain
SITE                    14
                        note = misc_feature - Xaa is S5, a-methyl, a-alkenylglycine
                         with 5 carbon chain
source                  1..16
                        mol_type = protein
                        organism = synthetic construct
SEQUENCE: 125
LSQETFXDLW KLLXEN                                                              16

SEQ ID NO: 126          moltype = AA  length = 15
FEATURE                 Location/Qualifiers
REGION                  1..15
                        note = Synthetic
SITE                    4
                        note = misc_feature - Xaa is R8, an enantiomer of S8,
                         a-methyl, a-alkenylglycine with 8 carbon chain
SITE                    11
                        note = misc_feature - Xaa is S5, a-methyl, a-alkenylglycine
                         with 5 carbon chain
source                  1..15
                        mol_type = protein
                        organism = synthetic construct
SEQUENCE: 126
ILRXAVSHMK XLRGT                                                               15

SEQ ID NO: 127          moltype = AA  length = 14
FEATURE                 Location/Qualifiers
REGION                  1..14
                        note = Synthetic
SITE                    4
                        note = misc_feature - Xaa is R8, an enantiomer of S8,
                         a-methyl, a-alkenylglycine with 8 carbon chain
SITE                    11
                        note = misc_feature - Xaa is S5, a-methyl, a-alkenylglycine
                         with 5 carbon chain
source                  1..14
                        mol_type = protein
                        organism = synthetic construct
SEQUENCE: 127
NELXRSFRSL XDSI                                                                14

SEQ ID NO: 128          moltype = AA  length = 14
FEATURE                 Location/Qualifiers
REGION                  1..14
                        note = Synthetic
SITE                    4
                        note = misc_feature - Xaa is R8, an enantiomer of S8,
                         a-methyl, a-alkenylglycine with 8 carbon chain
SITE                    11
                        note = misc_feature - Xaa is S5, a-methyl, a-alkenylglycine
                         with 5 carbon chain
source                  1..14
                        mol_type = protein
                        organism = synthetic construct
SEQUENCE: 128
NELXRSFRAL XDQI                                                                14

SEQ ID NO: 129          moltype = AA  length = 14
FEATURE                 Location/Qualifiers
REGION                  1..14
                        note = Synthetic
SITE                    4
                        note = misc_feature - Xaa is R8, an enantiomer of S8,
                         a-methyl, a-alkenylglycine with 8 carbon chain
SITE                    11
                        note = misc_feature - Xaa is S5, a-methyl, a-alkenylglycine
                         with 5 carbon chain
source                  1..14
                        mol_type = protein
                        organism = synthetic construct
SEQUENCE: 129
NELXRSFFAL XDSI                                                                14

SEQ ID NO: 130          moltype = AA  length = 14
FEATURE                 Location/Qualifiers
REGION                  1..14
                        note = Synthetic
SITE                    4
```

```
                        note = misc_feature - Xaa is R8, an enantiomer of S8,
                          a-methyl, a-alkenylglycine with 8 carbon chain
SITE                    11
                        note = misc_feature - Xaa is S5, a-methyl, a-alkenylglycine
                          with 5 carbon chain
source                  1..14
                        mol_type = protein
                        organism = synthetic construct
SEQUENCE: 130
NELXRSFFAL XDQI                                                               14

SEQ ID NO: 131          moltype = AA   length = 15
FEATURE                 Location/Qualifiers
REGION                  1..15
                        note = Synthetic
SITE                    3
                        note = misc_feature - Xaa is R8, an enantiomer of S8,
                          a-methyl, a-alkenylglycine with 8 carbon chain
SITE                    10
                        note = misc_feature - Xaa is S5, a-methyl, a-alkenylglycine
                          with 5 carbon chain
source                  1..15
                        mol_type = protein
                        organism = synthetic construct
SEQUENCE: 131
ILXMAVSHMX SLRGT                                                              15

SEQ ID NO: 132          moltype = AA   length = 14
FEATURE                 Location/Qualifiers
REGION                  1..14
                        note = Synthetic
SITE                    4
                        note = misc_feature - Xaa is R8, an enantiomer of S8,
                          a-methyl, a-alkenylglycine with 8 carbon chain
SITE                    11
                        note = misc_feature - Xaa is S5, a-methyl, a-alkenylglycine
                          with 5 carbon chain
source                  1..14
                        mol_type = protein
                        organism = synthetic construct
SEQUENCE: 132
NELXRSFRAL XDSI                                                               14

SEQ ID NO: 133          moltype = AA   length = 14
FEATURE                 Location/Qualifiers
REGION                  1..14
                        note = Synthetic
SITE                    4
                        note = misc_feature - Xaa is R8, an enantiomer of S8,
                          a-methyl, a-alkenylglycine with 8 carbon chain
SITE                    11
                        note = misc_feature - Xaa is S5, a-methyl, a-alkenylglycine
                          with 5 carbon chain
source                  1..14
                        mol_type = protein
                        organism = synthetic construct
SEQUENCE: 133
NELXRSFFSL XDQI                                                               14

SEQ ID NO: 134          moltype = AA   length = 15
FEATURE                 Location/Qualifiers
REGION                  1..15
                        note = Synthetic
SITE                    5
                        note = misc_feature - Xaa is R8, an enantiomer of S8,
                          a-methyl, a-alkenylglycine with 8 carbon chain
SITE                    12
                        note = misc_feature - Xaa is S5, a-methyl, a-alkenylglycine
                          with 5 carbon chain
source                  1..15
                        mol_type = protein
                        organism = synthetic construct
SEQUENCE: 134
WNELXRSFRS LXDQI                                                              15

SEQ ID NO: 135          moltype = AA   length = 14
FEATURE                 Location/Qualifiers
REGION                  1..14
                        note = Synthetic
```

| | |
|---|---|
| SITE | 4 |
| | note = misc_feature - Xaa is R8, an enantiomer of S8, a-methyl, a-alkenylglycine with 8 carbon chain |
| SITE | 11 |
| | note = misc_feature - Xaa is S5, a-methyl, a-alkenylglycine with 5 carbon chain |
| source | 1..14 |
| | mol_type = protein |
| | organism = synthetic construct |

SEQUENCE: 135
NQRXLSFFAL XDQI                                          14

| | |
|---|---|
| SEQ ID NO: 136 | moltype = AA   length = 14 |
| FEATURE | Location/Qualifiers |
| REGION | 1..14 |
| | note = Synthetic |
| SITE | 4 |
| | note = misc_feature - Xaa is R8, an enantiomer of S8, a-methyl, a-alkenylglycine with 8 carbon chain |
| SITE | 11 |
| | note = misc_feature - Xaa is S5, a-methyl, a-alkenylglycine with 5 carbon chain |
| source | 1..14 |
| | mol_type = protein |
| | organism = synthetic construct |

SEQUENCE: 136
NQLXLSFFAR XDQI                                          14

| | |
|---|---|
| SEQ ID NO: 137 | moltype = AA   length = 14 |
| FEATURE | Location/Qualifiers |
| REGION | 1..14 |
| | note = Synthetic |
| SITE | 4 |
| | note = misc_feature - Xaa is R8, an enantiomer of S8, a-methyl, a-alkenylglycine with 8 carbon chain |
| SITE | 11 |
| | note = misc_feature - Xaa is S5, a-methyl, a-alkenylglycine with 5 carbon chain |
| source | 1..14 |
| | mol_type = protein |
| | organism = synthetic construct |

SEQUENCE: 137
NKLXRSFFAL XDQI                                          14

| | |
|---|---|
| SEQ ID NO: 138 | moltype = AA   length = 24 |
| FEATURE | Location/Qualifiers |
| REGION | 1..24 |
| | note = Synthetic |
| SITE | 5 |
| | note = misc_feature - Xaa is R8, an enantiomer of S8, a-methyl, a-alkenylglycine with 8 carbon chain |
| SITE | 12 |
| | note = misc_feature - Xaa is S5, a-methyl, a-alkenylglycine with 5 carbon chain |
| source | 1..24 |
| | mol_type = protein |
| | organism = synthetic construct |

SEQUENCE: 138
NELKXSFFAL RXQIPELENN EKAP                               24

| | |
|---|---|
| SEQ ID NO: 139 | moltype = AA   length = 14 |
| FEATURE | Location/Qualifiers |
| REGION | 1..14 |
| | note = Synthetic |
| SITE | 4 |
| | note = misc_feature - Xaa is R8, an enantiomer of S8, a-methyl, a-alkenylglycine with 8 carbon chain |
| SITE | 11 |
| | note = misc_feature - Xaa is S5, a-methyl, a-alkenylglycine with 5 carbon chain |
| source | 1..14 |
| | mol_type = protein |
| | organism = synthetic construct |

SEQUENCE: 139
AHLXLCLEKL XGLV                                          14

| | |
|---|---|
| SEQ ID NO: 140 | moltype = AA   length = 14 |
| FEATURE | Location/Qualifiers |
| REGION | 1..14 |

```
                              note = Synthetic
SITE                          4
                              note = misc_feature - Xaa is R8, an enantiomer of S8,
                               a-methyl, a-alkenylglycine with 8 carbon chain
SITE                          11
                              note = misc_feature - Xaa is S5, a-methyl, a-alkenylglycine
                               with 5 carbon chain
source                        1..14
                              mol_type = protein
                              organism = synthetic construct
SEQUENCE: 140
NKLXRSFKAL XKQI                                                              14

SEQ ID NO: 141                moltype = AA   length = 14
FEATURE                       Location/Qualifiers
REGION                        1..14
                              note = Synthetic
SITE                          5
                              note = misc_feature - Xaa is R8, an enantiomer of S8,
                               a-methyl, a-alkenylglycine with 8 carbon chain
SITE                          12
                              note = misc_feature - Xaa is S5, a-methyl, a-alkenylglycine
                               with 5 carbon chain
source                        1..14
                              mol_type = protein
                              organism = synthetic construct
SEQUENCE: 141
NELKXSFFAL RXQI                                                              14

SEQ ID NO: 142                moltype = AA   length = 24
FEATURE                       Location/Qualifiers
REGION                        1..24
                              note = Synthetic
SITE                          4
                              note = misc_feature - Xaa is R8, an enantiomer of S8,
                               a-methyl, a-alkenylglycine with 8 carbon chain
SITE                          11
                              note = misc_feature - Xaa is S5, a-methyl, a-alkenylglycine
                               with 5 carbon chain
source                        1..24
                              mol_type = protein
                              organism = synthetic construct
SEQUENCE: 142
NQLXRSFFAL XDQIPELENN EKAP                                                   24

SEQ ID NO: 143                moltype = AA   length = 14
FEATURE                       Location/Qualifiers
REGION                        1..14
                              note = Synthetic
SITE                          3
                              note = misc_feature - Xaa is R8, an enantiomer of S8,
                               a-methyl, a-alkenylglycine with 8 carbon chain
SITE                          10
                              note = misc_feature - Xaa is S5, a-methyl, a-alkenylglycine
                               with 5 carbon chain
source                        1..14
                              mol_type = protein
                              organism = synthetic construct
SEQUENCE: 143
KVXILKKATX YILS                                                              14

SEQ ID NO: 144                moltype = AA   length = 14
FEATURE                       Location/Qualifiers
REGION                        1..14
                              note = Synthetic
SITE                          1
                              note = misc_feature - Xaa is R8, an enantiomer of S8,
                               a-methyl, a-alkenylglycine with 8 carbon chain
SITE                          8
                              note = misc_feature - Xaa is S5, a-methyl, a-alkenylglycine
                               with 5 carbon chain
source                        1..14
                              mol_type = protein
                              organism = synthetic construct
SEQUENCE: 144
XKRRAHAXAE RARR                                                              14

SEQ ID NO: 145                moltype = AA   length = 17
FEATURE                       Location/Qualifiers
```

```
REGION                    1..17
                          note = Synthetic
SITE                      8
                          note = misc_feature - Xaa is R8, an enantiomer of S8,
                           a-methyl, a-alkenylglycine with 8 carbon chain
SITE                      15
                          note = misc_feature - Xaa is S5, a-methyl, a-alkenylglycine
                           with 5 carbon chain
source                    1..17
                          mol_type = protein
                          organism = synthetic construct
SEQUENCE: 145
EENAKRRXHN ALERXRR                                                         17

SEQ ID NO: 146            moltype = AA  length = 10
FEATURE                   Location/Qualifiers
REGION                    1..10
                          note = Synthetic
SITE                      4
                          note = misc_feature - Xaa is R8, an enantiomer of S8,
                           a-methyl, a-alkenylglycine with 8 carbon chain
SITE                      7
                          note = misc_feature - Xaa is S5, a-methyl, a-alkenylglycine
                           with 5 carbon chain
source                    1..10
                          mol_type = protein
                          organism = synthetic construct
SEQUENCE: 146
NQLXLSXDQI                                                                 10

SEQ ID NO: 147            moltype = AA  length = 10
FEATURE                   Location/Qualifiers
REGION                    1..10
                          note = Synthetic
SITE                      4
                          note = misc_feature - Xaa is R8, an enantiomer of S8,
                           a-methyl, a-alkenylglycine with 8 carbon chain
SITE                      7
                          note = misc_feature - Xaa is S5, a-methyl, a-alkenylglycine
                           with 5 carbon chain
source                    1..10
                          mol_type = protein
                          organism = synthetic construct
SEQUENCE: 147
NQLXFSXDQI                                                                 10

SEQ ID NO: 148            moltype = AA  length = 23
FEATURE                   Location/Qualifiers
REGION                    1..23
                          note = Synthetic
SITE                      14
                          note = misc_feature - Xaa is R8, an enantiomer of S8,
                           a-methyl, a-alkenylglycine with 8 carbon chain
SITE                      21
                          note = misc_feature - Xaa is S5, a-methyl, a-alkenylglycine
                           with 5 carbon chain
source                    1..23
                          mol_type = protein
                          organism = synthetic construct
SEQUENCE: 148
TILKASVDYI RKLXREQQRA XEL                                                  23

SEQ ID NO: 149            moltype = AA  length = 11
FEATURE                   Location/Qualifiers
REGION                    1..11
                          note = Synthetic
SITE                      4
                          note = misc_feature - Xaa is R8, an enantiomer of S8,
                           a-methyl, a-alkenylglycine with 8 carbon chain
SITE                      8
                          note = misc_feature - Xaa is S5, a-methyl, a-alkenylglycine
                           with 5 carbon chain
source                    1..11
                          mol_type = protein
                          organism = synthetic construct
SEQUENCE: 149
FNIXDRIXTL I                                                               11

SEQ ID NO: 150            moltype = AA  length = 11
```

-continued

```
FEATURE                 Location/Qualifiers
REGION                  1..11
                        note = Synthetic
SITE                    4
                        note = misc_feature - Xaa is R8, an enantiomer of S8,
                         a-methyl, a-alkenylglycine with 8 carbon chain
SITE                    8
                        note = misc_feature - Xaa is S5, a-methyl, a-alkenylglycine
                         with 5 carbon chain
source                  1..11
                        mol_type = protein
                        organism = synthetic construct
SEQUENCE: 150
RNIXDRIXTR I                                                             11

SEQ ID NO: 151          moltype = AA  length = 24
FEATURE                 Location/Qualifiers
REGION                  1..24
                        note = Synthetic
SITE                    15
                        note = misc_feature - Xaa is R8, an enantiomer of S8,
                         a-methyl, a-alkenylglycine with 8 carbon chain
SITE                    22
                        note = misc_feature - Xaa is S5, a-methyl, a-alkenylglycine
                         with 5 carbon chain
source                  1..24
                        mol_type = protein
                        organism = synthetic construct
SEQUENCE: 151
KATEYIQYNL RRKNXTHQQD IXDL                                               24

SEQ ID NO: 152          moltype = AA  length = 26
FEATURE                 Location/Qualifiers
REGION                  1..26
                        note = Synthetic
SITE                    4
                        note = misc_feature - Xaa is R8, an enantiomer of S8,
                         a-methyl, a-alkenylglycine with 8 carbon chain
SITE                    11
                        note = misc_feature - Xaa is S5, a-methyl, a-alkenylglycine
                         with 5 carbon chain
source                  1..26
                        mol_type = protein
                        organism = synthetic construct
SEQUENCE: 152
NELXRSFFAL XDQIDQIPAA KRVKLD                                             26

SEQ ID NO: 153          moltype = AA  length = 14
FEATURE                 Location/Qualifiers
REGION                  1..14
                        note = Synthetic
SITE                    4
                        note = misc_feature - Xaa is R8, an enantiomer of S8,
                         a-methyl, a-alkenylglycine with 8 carbon chain
SITE                    11
                        note = misc_feature - Xaa is S5, a-methyl, a-alkenylglycine
                         with 5 carbon chain
source                  1..14
                        mol_type = protein
                        organism = synthetic construct
SEQUENCE: 153
RNIXDRIKEL XTLI                                                          14

SEQ ID NO: 154          moltype = AA  length = 14
FEATURE                 Location/Qualifiers
REGION                  1..14
                        note = Synthetic
SITE                    5
                        note = misc_feature - Xaa is R8, an enantiomer of S8,
                         a-methyl, a-alkenylglycine with 8 carbon chain
SITE                    12
                        note = misc_feature - Xaa is S5, a-methyl, a-alkenylglycine
                         with 5 carbon chain
source                  1..14
                        mol_type = protein
                        organism = synthetic construct
SEQUENCE: 154
FNINXRIKEL GXLI                                                          14
```

```
SEQ ID NO: 155          moltype = AA   length = 14
FEATURE                 Location/Qualifiers
REGION                  1..14
                        note = Synthetic
SITE                    4
                        note = misc_feature - Xaa is R8, an enantiomer of S8,
                         a-methyl, a-alkenylglycine with 8 carbon chain
SITE                    11
                        note = misc_feature - Xaa is S5, a-methyl, a-alkenylglycine
                         with 5 carbon chain
source                  1..14
                        mol_type = protein
                        organism = synthetic construct
SEQUENCE: 155
FNIXDRIKEL XTRI                                                            14

SEQ ID NO: 156          moltype = AA   length = 14
FEATURE                 Location/Qualifiers
REGION                  1..14
                        note = Synthetic
SITE                    4
                        note = misc_feature - Xaa is R8, an enantiomer of S8,
                         a-methyl, a-alkenylglycine with 8 carbon chain
SITE                    11
                        note = misc_feature - Xaa is S5, a-methyl, a-alkenylglycine
                         with 5 carbon chain
source                  1..14
                        mol_type = protein
                        organism = synthetic construct
SEQUENCE: 156
NQLXRSFRAL XDQI                                                            14

SEQ ID NO: 157          moltype = AA   length = 24
FEATURE                 Location/Qualifiers
REGION                  1..24
                        note = Synthetic
SITE                    4
                        note = misc_feature - Xaa is R8, an enantiomer of S8,
                         a-methyl, a-alkenylglycine with 8 carbon chain
SITE                    11
                        note = misc_feature - Xaa is S5, a-methyl, a-alkenylglycine
                         with 5 carbon chain
source                  1..24
                        mol_type = protein
                        organism = synthetic construct
SEQUENCE: 157
NELXRSFFAL XDQIDQIPKK KRKV                                                 24

SEQ ID NO: 158          moltype = AA   length = 15
FEATURE                 Location/Qualifiers
REGION                  1..15
                        note = Synthetic
SITE                    5
                        note = misc_feature - Xaa is R8, an enantiomer of S8,
                         a-methyl, a-alkenylglycine with 8 carbon chain
SITE                    12
                        note = misc_feature - Xaa is S5, a-methyl, a-alkenylglycine
                         with 5 carbon chain
source                  1..15
                        mol_type = protein
                        organism = synthetic construct
SEQUENCE: 158
ENPEXILDEH VXRVM                                                           15

SEQ ID NO: 159          moltype = AA   length = 17
FEATURE                 Location/Qualifiers
REGION                  1..17
                        note = Synthetic
SITE                    4
                        note = misc_feature - Xaa is S5, a-methyl, a-alkenylglycine
                         with 5 carbon chain
SITE                    8
                        note = misc_feature - Xaa is B5, a-methyl, a-alkenylglycine
                         with two 5 carbon chain
SITE                    15
                        note = misc_feature - Xaa is S8, a-methyl, a-alkenylglycine
                         with 8 carbon chain
source                  1..17
                        mol_type = protein
```

```
                            organism = synthetic construct
SEQUENCE: 159
TRQXRRAXRR RWREXQR                                                      17

SEQ ID NO: 160          moltype = AA  length = 12
FEATURE                 Location/Qualifiers
REGION                  1..12
                        note = Synthetic
SITE                    1
                        note = misc_feature - Xaa is S5, a-methyl, a-alkenylglycine
                          with 5 carbon chain
SITE                    5
                        note = misc_feature - Xaa is B5, a-methyl, a-alkenylglycine
                          with two 5 carbon chain
SITE                    12
                        note = misc_feature - Xaa is S8, a-methyl, a-alkenylglycine
                          with 8 carbon chain
source                  1..12
                        mol_type = protein
                        organism = synthetic construct
SEQUENCE: 160
XRRNXRRRWR EX                                                           12

SEQ ID NO: 161          moltype = AA  length = 37
FEATURE                 Location/Qualifiers
REGION                  1..37
                        note = Synthetic
SITE                    5
                        note = misc_feature - Xaa is R5, an enantiomer of S5,
                          a-methyl, a-alkenylglycine with 5 carbon chain
SITE                    13
                        note = misc_feature - Xaa is S8, a-methyl, a-alkenylglycine
                          with 8 carbon chain
source                  1..37
                        mol_type = protein
                        organism = synthetic construct
SEQUENCE: 161
EYIQXNLRRK NHXHQQDIDD LKRQNALLEQ QVRALGG                                 37

SEQ ID NO: 162          moltype = AA  length = 15
FEATURE                 Location/Qualifiers
REGION                  1..15
                        note = Synthetic
SITE                    4
                        note = misc_feature - Xaa is S5, a-methyl, a-alkenylglycine
                          with 5 carbon chain
SITE                    6
                        note = misc_feature - Xaa is B5, a-methyl, a-alkenylglycine
                          with two 5 carbon chain
SITE                    13
                        note = misc_feature - Xaa is S8, a-methyl, a-alkenylglycine
                          with 8 carbon chain
source                  1..15
                        mol_type = protein
                        organism = synthetic construct
SEQUENCE: 162
TRQXQXRRRW REXQR                                                        15

SEQ ID NO: 163          moltype = AA  length = 17
FEATURE                 Location/Qualifiers
REGION                  1..17
                        note = Synthetic
SITE                    4
                        note = misc_feature - Xaa is S5, a-methyl, a-alkenylglycine
                          with 5 carbon chain
SITE                    8
                        note = misc_feature - Xaa is B5, a-methyl, a-alkenylglycine
                          with two 5 carbon chain
SITE                    15
                        note = misc_feature - Xaa is S8, a-methyl, a-alkenylglycine
                          with 8 carbon chain
source                  1..17
                        mol_type = protein
                        organism = synthetic construct
SEQUENCE: 163
TRQXRRNXRR RWREXQR                                                      17

SEQ ID NO: 164          moltype = AA  length = 17
FEATURE                 Location/Qualifiers
```

```
REGION                  1..17
                        note = Synthetic
SITE                    1
                        note = misc_feature - Xaa is R8, an enantiomer of S8,
                         a-methyl, a-alkenylglycine with 8 carbon chain
SITE                    8
                        note = misc_feature - Xaa is B5, a-methyl, a-alkenylglycine
                         with two 5 carbon chain
SITE                    15
                        note = misc_feature - Xaa is S8, a-methyl, a-alkenylglycine
                         with 8 carbon chain
source                  1..17
                        mol_type = protein
                        organism = synthetic construct
SEQUENCE: 164
XRQARRNXRR RWREXQR                                                          17

SEQ ID NO: 165          moltype = AA  length = 17
FEATURE                 Location/Qualifiers
REGION                  1..17
                        note = Synthetic
SITE                    1
                        note = misc_feature - Xaa is is R8, an enantiomer of S8,
                         a-methyl, a-alkenylglycine with 8 carbon chain
SITE                    8
                        note = misc_feature - Xaa is B5, a-methyl, a-alkenylglycine
                         with two 5 carbon chain
SITE                    15
                        note = misc_feature - Xaa is S8, a-methyl, a-alkenylglycine
                         with 8 carbon chain
source                  1..17
                        mol_type = protein
                        organism = synthetic construct
SEQUENCE: 165
XRQARRQXRR RWREXQR                                                          17

SEQ ID NO: 166          moltype = AA  length = 12
FEATURE                 Location/Qualifiers
REGION                  1..12
                        note = Synthetic
SITE                    1
                        note = misc_feature - Xaa is S5, a-methyl, a-alkenylglycine
                         with 5 carbon chain
SITE                    5
                        note = misc_feature - Xaa is B5, a-methyl, a-alkenylglycine
                         with two 5 carbon chain
SITE                    12
                        note = misc_feature - Xaa is S8, a-methyl, a-alkenylglycine
                         with 8 carbon chain
source                  1..12
                        mol_type = protein
                        organism = synthetic construct
SEQUENCE: 166
XRRNXRRRWR RX                                                               12

SEQ ID NO: 167          moltype = AA  length = 11
FEATURE                 Location/Qualifiers
REGION                  1..11
                        note = Synthetic
SITE                    4
                        note = misc_feature - Xaa is B5, a-methyl, a-alkenylglycine
                         with two 5 carbon chain
SITE                    11
                        note = misc_feature - Xaa is S8, a-methyl, a-alkenylglycine
                         with 8 carbon chain
source                  1..11
                        mol_type = protein
                        organism = synthetic construct
SEQUENCE: 167
RRAXRRRWRR X                                                                11

SEQ ID NO: 168          moltype = AA  length = 13
FEATURE                 Location/Qualifiers
REGION                  1..13
                        note = Synthetic
SITE                    1
                        note = misc_feature - Xaa is S5, a-methyl, a-alkenylglycine
                         with 5 carbon chain
SITE                    5
```

| | | |
|---|---|---|
| SITE | 12 | note = misc_feature - Xaa is B5, a-methyl, a-alkenylglycine with two 5 carbon chain |
| | | note = misc_feature - Xaa is S8, a-methyl, a-alkenylglycine with 8 carbon chain |
| SITE | 13 | note = misc_feature - Xaa can be any naturally occurring amino acid |
| source | 1..13 | mol_type = protein<br>organism = synthetic construct |

SEQUENCE: 168
XKIWXQNRRN LKX                                                                     13

| | | |
|---|---|---|
| SEQ ID NO: 169<br>FEATURE<br>REGION | moltype = AA   length = 12<br>Location/Qualifiers<br>1..12 | note = Synthetic |
| SITE | 1 | note = misc_feature - Xaa is S5, a-methyl, a-alkenylglycine with 5 carbon chain |
| SITE | 5 | note = misc_feature - Xaa is B5, a-methyl, a-alkenylglycine with two 5 carbon chain |
| SITE | 12 | note = misc_feature - Xaa is S8, a-methyl, a-alkenylglycine with 8 carbon chain |
| source | 1..12 | mol_type = protein<br>organism = synthetic construct |

SEQUENCE: 169
XRRRXRRRRR RX                                                                      12

| | | |
|---|---|---|
| SEQ ID NO: 170<br>FEATURE<br>REGION | moltype = AA   length = 12<br>Location/Qualifiers<br>1..12 | note = Synthetic |
| SITE | 1 | note = misc_feature - Xaa is S5, a-methyl, a-alkenylglycine with 5 carbon chain |
| SITE | 5 | note = misc_feature - Xaa is B5, a-methyl, a-alkenylglycine with two 5 carbon chain |
| SITE | 12 | note = misc_feature - Xaa is S8, a-methyl, a-alkenylglycine with 8 carbon chain |
| source | 1..12 | mol_type = protein<br>organism = synthetic construct |

SEQUENCE: 170
XGRKXRRQRR RX                                                                      12

| | | |
|---|---|---|
| SEQ ID NO: 171<br>FEATURE<br>REGION | moltype = AA   length = 12<br>Location/Qualifiers<br>1..12 | note = Synthetic |
| SITE | 1 | note = misc_feature - Xaa is S5, a-methyl, a-alkenylglycine with 5 carbon chain |
| SITE | 5 | note = misc_feature - Xaa is B5, a-methyl, a-alkenylglycine with two 5 carbon chain |
| SITE | 12 | note = misc_feature - Xaa is S8, a-methyl, a-alkenylglycine with 8 carbon chain |
| source | 1..12 | mol_type = protein<br>organism = synthetic construct |

SEQUENCE: 171
XRRQXRRRWR RX                                                                      12

| | | |
|---|---|---|
| SEQ ID NO: 172<br>FEATURE<br>REGION | moltype = AA   length = 16<br>Location/Qualifiers<br>1..16 | note = Synthetic |
| SITE | 3 | note = misc_feature - Xaa is S5, a-methyl, a-alkenylglycine with 5 carbon chain |
| SITE | 7 | |

-continued

```
                           note = misc_feature - Xaa is B5, a-methyl, a-alkenylglycine
                             with two 5 carbon chain
SITE                       14
                           note = misc_feature - Xaa is S8, a-methyl, a-alkenylglycine
                             with 8 carbon chain
source                     1..16
                           mol_type = protein
                           organism = synthetic construct
SEQUENCE: 172
RQXKIWXQNR RMKXKK                                                              16

SEQ ID NO: 173             moltype = AA  length = 12
FEATURE                    Location/Qualifiers
REGION                     1..12
                           note = Synthetic
SITE                       1
                           note = misc_feature - Xaa is S5, a-methyl, a-alkenylglycine
                             with 5 carbon chain
SITE                       5
                           note = misc_feature - Xaa is B5, a-methyl, a-alkenylglycine
                             with two 5 carbon chain
SITE                       12
                           note = misc_feature - Xaa is S8, a-methyl, a-alkenylglycine
                             with 8 carbon chain
source                     1..12
                           mol_type = protein
                           organism = synthetic construct
SEQUENCE: 173
XKIWXQNRRA KX                                                                  12

SEQ ID NO: 174             moltype = AA  length = 12
FEATURE                    Location/Qualifiers
REGION                     1..12
                           note = Synthetic
SITE                       1
                           note = misc_feature - Xaa is S5, a-methyl, a-alkenylglycine
                             with 5 carbon chain
SITE                       5
                           note = misc_feature - Xaa is B5, a-methyl, a-alkenylglycine
                             with two 5 carbon chain
SITE                       12
                           note = misc_feature - Xaa is S8, a-methyl, a-alkenylglycine
                             with 8 carbon chain
source                     1..12
                           mol_type = protein
                           organism = synthetic construct
SEQUENCE: 174
XRRRXRRRWR RX                                                                  12

SEQ ID NO: 175             moltype = AA  length = 21
FEATURE                    Location/Qualifiers
REGION                     1..21
                           note = Synthetic
SITE                       2
                           note = misc_feature - Xaa is S5, a-methyl, a-alkenylglycine
                             with 5 carbon chain
SITE                       6
                           note = misc_feature - Xaa is B5, a-methyl, a-alkenylglycine
                             with two 5 carbon chain
SITE                       13
                           note = misc_feature - Xaa is S8, a-methyl, a-alkenylglycine
                             with 8 carbon chain
source                     1..21
                           mol_type = protein
                           organism = synthetic construct
SEQUENCE: 175
LXILQXAVQV ILXLEQQVRE R                                                        21

SEQ ID NO: 176             moltype = AA  length = 21
FEATURE                    Location/Qualifiers
REGION                     1..21
                           note = Synthetic
SITE                       9
                           note = misc_feature - Xaa is S5, a-methyl, a-alkenylglycine
                             with 5 carbon chain
SITE                       13
                           note = misc_feature - Xaa is B5, a-methyl, a-alkenylglycine
                             with two 5 carbon chain
SITE                       20
```

-continued

```
                               note = misc_feature - Xaa is S8, a-methyl, a-alkenylglycine
                                  with 8 carbon chain
source                         1..21
                               mol_type = protein
                               organism = synthetic construct
SEQUENCE: 176
LLILQQAVXV ILXLEQQVRX R                                                    21

SEQ ID NO: 177              moltype = AA  length = 16
FEATURE                     Location/Qualifiers
REGION                      1..16
                               note = Synthetic
SITE                        3
                               note = misc_feature - Xaa is S5, a-methyl, a-alkenylglycine
                                  with 5 carbon chain
SITE                        7
                               note = misc_feature - Xaa is B8, a-methyl, a-alkenylglycine
                                  with two 8 carbon chain
SITE                        14
                               note = misc_feature - Xaa is S8, a-methyl, a-alkenylglycine
                                  with 8 carbon chain
source                         1..16
                               mol_type = protein
                               organism = synthetic construct
SEQUENCE: 177
LSXETFXDLW KLLXEN                                                          16

SEQ ID NO: 178              moltype = AA  length = 16
FEATURE                     Location/Qualifiers
REGION                      1..16
                               note = Synthetic
SITE                        4
                               note = misc_feature - Xaa is S5, a-methyl, a-alkenylglycine
                                  with 5 carbon chain
SITE                        8
                               note = misc_feature - Xaa is B8, a-methyl, a-alkenylglycine
                                  with two 8 carbon chain
SITE                        15
                               note = misc_feature - Xaa is S8, a-methyl, a-alkenylglycine
                                  with 8 carbon chain
source                         1..16
                               mol_type = protein
                               organism = synthetic construct
SEQUENCE: 178
LSQXTFSXLW KLLAXN                                                          16

SEQ ID NO: 179              moltype = AA  length = 21
FEATURE                     Location/Qualifiers
REGION                      1..21
                               note = Synthetic
SITE                        2
                               note = misc_feature - Xaa is S5, a-methyl, a-alkenylglycine
                                  with 5 carbon chain
SITE                        6
                               note = misc_feature - Xaa is B5, a-methyl, a-alkenylglycine
                                  with two 5 carbon chain
SITE                        10
                               note = misc_feature - Xaa is R5, an enantiomer of S5,
                                  a-methyl, a-alkenylglycine with 5 carbon chain
source                         1..21
                               mol_type = protein
                               organism = synthetic construct
SEQUENCE: 179
LXILQXAVQX ILGLEQQVRE R                                                    21

SEQ ID NO: 180              moltype = AA  length = 21
FEATURE                     Location/Qualifiers
REGION                      1..21
                               note = Synthetic
SITE                        9
                               note = misc_feature - Xaa is S5, a-methyl, a-alkenylglycine
                                  with 5 carbon chain
SITE                        13
                               note = misc_feature - Xaa is B5, a-methyl, a-alkenylglycine
                                  with two 5 carbon chain
SITE                        17
                               note = misc_feature - Xaa is R5, an enantiomer of S5,
                                  a-methyl, a-alkenylglycine with 5 carbon chain
source                         1..21
```

```
                        mol_type = protein
                        organism = synthetic construct
SEQUENCE: 180
LLILQQAVXV ILXLEQXVRE R                                               21

SEQ ID NO: 181          moltype = AA  length = 21
FEATURE                 Location/Qualifiers
REGION                  1..21
                        note = Synthetic
SITE                    5
                        note = misc_feature - Xaa is S5, a-methyl, a-alkenylglycine
                         with 5 carbon chain
SITE                    9
                        note = misc_feature - Xaa is B5, a-methyl, a-alkenylglycine
                         with two 5 carbon chain
SITE                    13
                        note = misc_feature - Xaa is R5, an enantiomer of S5,
                         a-methyl, a-alkenylglycine with 5 carbon chain
source                  1..21
                        mol_type = protein
                        organism = synthetic construct
SEQUENCE: 181
LLILXQAVXV ILXLEQQVRE R                                               21

SEQ ID NO: 182          moltype = AA  length = 10
FEATURE                 Location/Qualifiers
REGION                  1..10
                        note = Synthetic
SITE                    1
                        note = misc_feature - Xaa is R5, an enantiomer of S5,
                         a-methyl, a-alkenylglycine with 5 carbon chain
SITE                    5
                        note = misc_feature - Xaa is B5, a-methyl, a-alkenylglycine
                         with two 5 carbon chain
SITE                    9
                        note = misc_feature - Xaa is S5, a-methyl, a-alkenylglycine
                         with 5 carbon chain
source                  1..10
                        mol_type = protein
                        organism = synthetic construct
SEQUENCE: 182
XDFSXYWKXL                                                            10

SEQ ID NO: 183          moltype = AA  length = 16
FEATURE                 Location/Qualifiers
REGION                  1..16
                        note = Synthetic
SITE                    3
                        note = misc_feature - Xaa is S5, a-methyl, a-alkenylglycine
                         with 5 carbon chain
SITE                    7
                        note = misc_feature - Xaa is B8, a-methyl, a-alkenylglycine
                         with two 8 carbon chain
SITE                    14
                        note = misc_feature - Xaa is S8, a-methyl, a-alkenylglycine
                         with 8 carbon chain
source                  1..16
                        mol_type = protein
                        organism = synthetic construct
SEQUENCE: 183
LSXETAXDLW KLLXEN                                                     16

SEQ ID NO: 184          moltype = AA  length = 23
FEATURE                 Location/Qualifiers
REGION                  1..23
                        note = Synthetic
SITE                    9
                        note = misc_feature - Xaa is S5, a-methyl, a-alkenylglycine
                         with 5 carbon chain
SITE                    13
                        note = misc_feature - Xaa is B5, a-methyl, a-alkenylglycine
                         with two 5 carbon chain
SITE                    21
                        note = misc_feature - Xaa is S8, a-methyl, a-alkenylglycine
                         with 8 carbon chain
source                  1..23
                        mol_type = protein
                        organism = synthetic construct
SEQUENCE: 184
```

EDIIRNIAXH LAXVGDWNLD XSI                                                                 23

SEQ ID NO: 185           moltype = AA  length = 18
FEATURE                  Location/Qualifiers
REGION                   1..18
                         note = Synthetic
SITE                     4
                         note = misc_feature - Xaa is S5, a-methyl, a-alkenylglycine
                         with 5 carbon chain
SITE                     8
                         note = misc_feature - Xaa is B5, a-methyl, a-alkenylglycine
                         with two 5 carbon chain
SITE                     16
                         note = misc_feature - Xaa is S8, a-methyl, a-alkenylglycine
                         with 8 carbon chain
source                   1..18
                         mol_type = protein
                         organism = synthetic construct
SEQUENCE: 185
NIAXHLAXVG DWNLDXSI                                                                       18

SEQ ID NO: 186           moltype = AA  length = 13
FEATURE                  Location/Qualifiers
REGION                   1..13
                         note = Synthetic
SITE                     1
                         note = misc_feature - Xaa is S5, a-methyl, a-alkenylglycine
                         with 5 carbon chain
SITE                     5
                         note = misc_feature - Xaa is B5, a-methyl, a-alkenylglycine
                         with two 5 carbon chain
SITE                     13
                         note = misc_feature - Xaa is S8, a-methyl, a-alkenylglycine
                         with 8 carbon chain
source                   1..13
                         mol_type = protein
                         organism = synthetic construct
SEQUENCE: 186
XHLAXVGDWN LDX                                                                            13

SEQ ID NO: 187           moltype = AA  length = 29
FEATURE                  Location/Qualifiers
REGION                   1..29
                         note = Synthetic
SITE                     6
                         note = misc_feature - Xaa is R8, an enantiomer of S8,
                         a-methyl, a-alkenylglycine with 8 carbon chain
SITE                     13
                         note = misc_feature - Xaa is S5, a-methyl, a-alkenylglycine
                         with 5 carbon chain
SITE                     19
                         note = misc_feature - Xaa is R8, an enantiomer of S8,
                         a-methyl, a-alkenylglycine with 8 carbon chain
SITE                     26
                         note = misc_feature - Xaa is S5, a-methyl, a-alkenylglycine
                         with 5 carbon chain
source                   1..29
                         mol_type = protein
                         organism = synthetic construct
SEQUENCE: 187
NVKRRXHNVL ERXRRNELXR SFFALXDQI                                                           29

SEQ ID NO: 188           moltype = AA  length = 38
FEATURE                  Location/Qualifiers
REGION                   1..38
                         note = Synthetic
SITE                     1
                         note = misc_feature - Xaa is S5, a-methyl, a-alkenylglycine
                         with 5 carbon chain
SITE                     5
                         note = misc_feature - Xaa is B5, a-methyl, a-alkenylglycine
                         with two 5 carbon chain
SITE                     13
                         note = misc_feature - Xaa is S8, a-methyl, a-alkenylglycine
                         with 8 carbon chain
source                   1..38
                         mol_type = protein
                         organism = synthetic construct
SEQUENCE: 188

-continued

```
XYIQXNLRRK NHXHQQDIDD LLKRQNALLE QQVRALGG                              38

SEQ ID NO: 189          moltype = AA   length = 16
FEATURE                 Location/Qualifiers
REGION                  1..16
                        note = Synthetic
SITE                    4
                        note = misc_feature - Xaa is S5, a-methyl, a-alkenylglycine
                         with 5 carbon chain
SITE                    8
                        note = misc_feature - Xaa is B5, a-methyl, a-alkenylglycine
                         with two 5 carbon chain
SITE                    16
                        note = misc_feature - Xaa is S8, a-methyl, a-alkenylglycine
                         with 8 carbon chain
source                  1..16
                        mol_type = protein
                        organism = synthetic construct
SEQUENCE: 189
NIAXHLAXVG DWNLDX                                                      16

SEQ ID NO: 190          moltype = AA   length = 37
FEATURE                 Location/Qualifiers
REGION                  1..37
                        note = Synthetic
SITE                    9
                        note = misc_feature - Xaa is S5, a-methyl, a-alkenylglycine
                         with 5 carbon chain
SITE                    13
                        note = misc_feature - Xaa is B5, a-methyl, a-alkenylglycine
                         with two 5 carbon chain
SITE                    20
                        note = misc_feature - Xaa is S8, a-methyl, a-alkenylglycine
                         with 8 carbon chain
source                  1..37
                        mol_type = protein
                        organism = synthetic construct
SEQUENCE: 190
EYIQYNLRXK NHXHQQDIDX LKRQNALLEQ QVRALGG                               37

SEQ ID NO: 191          moltype = AA   length = 14
FEATURE                 Location/Qualifiers
REGION                  1..14
                        note = Synthetic
SITE                    4
                        note = misc_feature - Xaa is S5, a-methyl, a-alkenylglycine
                         with 5 carbon chain
SITE                    11
                        note = misc_feature - Xaa is R8, an enantiomer of S8,
                         a-methyl, a-alkenylglycine with 8 carbon chain
source                  1..14
                        mol_type = protein
                        organism = synthetic construct
SITE                    1
                        note = D-Isoleucine
SITE                    2
                        note = D-Glutamine
SITE                    3
                        note = D-Aspartic acid
SITE                    5
                        note = D-Leucine
SITE                    6
                        note = D-Alanine
SITE                    7
                        note = D-Phenylalanine
SITE                    8
                        note = D-Phenylalanine
SITE                    9
                        note = D-Serine
SITE                    10
                        note = D-Arginine
SITE                    12
                        note = D-Leucine
SITE                    13
                        note = D-Glutamine
SITE                    14
                        note = D-Asparagine
SEQUENCE: 191
IQDXLAFFSR XLQN                                                        14
```

```
SEQ ID NO: 192            moltype = AA  length = 15
FEATURE                   Location/Qualifiers
REGION                    1..15
                          note = Synthetic
SITE                      4
                          note = misc_feature - Xaa is R8, an enantiomer of S8,
                           a-methyl, a-alkenylglycine with 8 carbon chain
SITE                      11
                          note = misc_feature - Xaa is S5, a-methyl, a-alkenylglycine
                           with 5 carbon chain
source                    1..15
                          mol_type = protein
                          organism = synthetic construct
SEQUENCE: 192
AHLXLCLEKL XGLVK                                                            15

SEQ ID NO: 193            moltype = AA  length = 14
FEATURE                   Location/Qualifiers
REGION                    1..14
                          note = Synthetic
SITE                      4
                          note = misc_feature - Xaa is R8, an enantiomer of S8,
                           a-methyl, a-alkenylglycine with 8 carbon chain
SITE                      11
                          note = misc_feature - Xaa is S5, a-methyl, a-alkenylglycine
                           with 5 carbon chain
source                    1..14
                          mol_type = protein
                          organism = synthetic construct
SITE                      1
                          note = D-Asparagine
SITE                      2
                          note = D-Glutamine
SITE                      3
                          note = D-Leucine
SITE                      5
                          note = D-Phenylalanine
SITE                      6
                          note = D-Serine
SITE                      7
                          note = D-Arginine
SITE                      8
                          note = D-Phenylalanine
SITE                      9
                          note = D-Alanine
SITE                      10
                          note = D-Leucine
SITE                      12
                          note = D-Aspartic acid
SITE                      13
                          note = D-Glutamine
SITE                      14
                          note = D-Isoleucine
SEQUENCE: 193
NQLXFSRFAL XDQI                                                             14

SEQ ID NO: 194            moltype = AA  length = 14
FEATURE                   Location/Qualifiers
source                    1..14
                          mol_type = protein
                          organism = synthetic construct
SITE                      4
                          note = misc_feature - Xaa is R8, an enantiomer of S8,
                           S-octenylalanine
SITE                      11
                          note = misc_feature - Xaa is S5, a-methyl, a-alkenylglycine
                           with 5 carbon chain
REGION                    1..14
                          note = Synthetic
SITE                      1
                          note = D-Asparagine
SITE                      2
                          note = D-Glutamine
SITE                      3
                          note = D-Leucine
SITE                      5
                          note = D-Arginine
SITE                      6
```

```
                    note = D-Serine
SITE            7
                    note = D-Phenylalanine
SITE            8
                    note = D-Phenylalanine
SITE            9
                    note = D=Alanine
SITE            10
                    note = D-Alanine
SITE            12
                    note = D-Aspartic acid
SITE            13
                    note = D-Glutamine
SITE            14
                    note = D-Isoleucine
SEQUENCE: 194
NQLXRSFFAL XDQI                                              14
```